US012752033B2

(12) United States Patent
Baarman et al.

(10) Patent No.: US 12,752,033 B2
(45) Date of Patent: Oct. 6, 2026

(54) SYSTEM AND METHOD OF DISINFECTION

(71) Applicant: UV Partners, Inc., Grand Haven, MI (US)

(72) Inventors: David W Baarman, Fennville, MI (US); Colin J. Moore, Grand Rapids, MI (US); Ryan D. Schamper, Grand Haven, MI (US)

(73) Assignee: UV Partners, Inc., Holland, MI (US)

( * ) Notice: Subject to any disclaimer, the term of this patent is extended or adjusted under 35 U.S.C. 154(b) by 961 days.

(21) Appl. No.: 17/789,929

(22) PCT Filed: Jan. 2, 2021

(86) PCT No.: PCT/US2021/012013
§ 371 (c)(1),
(2) Date: Jun. 29, 2022

(87) PCT Pub. No.: WO2021/138645
PCT Pub. Date: Jul. 8, 2021

(65) Prior Publication Data

US 2023/0039310 A1 Feb. 9, 2023

Related U.S. Application Data

(60) Provisional application No. 62/956,816, filed on Jan. 3, 2020.

(51) Int. Cl.
*A61L 9/20* (2006.01)

(52) U.S. Cl.
CPC ............ *A61L 9/20* (2013.01); *A61L 2209/111* (2013.01); *A61L 2209/12* (2013.01); *A61L 2209/14* (2013.01); *A61L 2209/15* (2013.01)

(58) Field of Classification Search
CPC .. A61L 9/20; A61L 2209/111; A61L 2209/12; A61L 2209/14; A61L 2209/15;
(Continued)

(56) References Cited

U.S. PATENT DOCUMENTS 2,359,021 A 9/1944 Campbell et al.
3,486,308 A 12/1969 Burt
(Continued)

FOREIGN PATENT DOCUMENTS

AU 2010250125 B2 11/2010
BR PI1010895 B1 1/2020
(Continued)

OTHER PUBLICATIONS

"Light Guide Techniques Using LED Lamps", Application Brief I-0003, Agilent Technologies, copyright 2001, downloaded as of Jan. 3, 2020, at http://www-eng.lbl.gov/~shuman/XENON/REFERENCES&OTHER_MISC/Lightpipe%20design.pdf, p. 1-22.
(Continued)

*Primary Examiner* — Xiuyu Tai
(74) *Attorney, Agent, or Firm* — Warner Norcross + Judd LLP

(57) ABSTRACT

A light fixture is provided to be disposed within a room and operable to provide visible light for the room and air disinfection via application of UV light to air flowing through an air treatment chamber. In one embodiment, one or more baffles may be disposed within the air chamber to substantially prevent UV light from leaking past the one or more baffles into the room. In one embodiment, a UV light regulator may be provided to selectively control an amount of UV light directed into the room.

10 Claims, 35 Drawing Sheets

(58) Field of Classification Search
CPC .. A61L 9/22; A61L 2209/212; A61L 2202/11; A61N 5/0618; A61N 2005/0663; A61N 2005/0652; A61N 2005/0661; A61M 21/00; A61M 2205/6054; A61M 2205/3592; A61M 2205/3313; A61M 2205/3553; A61M 2206/14; A61M 21/02; A61M 2205/3368; A61M 2205/3673; A61M 2205/7509; A61M 2205/7518; A61M 2205/16; A61M 2205/3561; A61M 2021/0044; A61M 16/1055; A61M 2205/8206; A61M 16/0066; A61M 6/1075; F21S 9/022; F21Y 2115/10; H05B 47/19; F21V 23/0435; F21V 29/673; F21V 23/003; F24F 13/078; F24F 8/20; F24F 8/22
See application file for complete search history.

(56) References Cited

U.S. PATENT DOCUMENTS

| | | | |
|---|---|---|---|
| 4,042,004 | A | 8/1977 | Kwan |
| 4,730,551 | A | 3/1988 | Peludat |
| 5,884,500 | A | 3/1999 | Wetzel |
| 5,891,399 | A | 4/1999 | Owesen |
| 6,497,840 | B1 | 12/2002 | Palestro et al. |
| 6,869,468 | B2 | 3/2005 | Gibson |
| 6,869,498 | B1 | 3/2005 | Tsai et al. |
| 6,878,195 | B2 | 4/2005 | Gibson |
| 7,166,259 | B2 | 1/2007 | Beam et al. |
| 7,332,006 | B2 | 2/2008 | Kim et al. |
| 7,582,256 | B1 | 9/2009 | Geron et al. |
| 7,763,212 | B2 | 7/2010 | McEllen |
| 7,922,351 | B2 | 4/2011 | Welker |
| 8,080,203 | B2 | 12/2011 | First et al. |
| 8,350,228 | B2 | 1/2013 | Welker |
| 8,439,517 | B2 | 5/2013 | Welker |
| 8,911,114 | B2 | 12/2014 | Tokarz et al. |
| 9,308,289 | B2 | 4/2016 | Graff et al. |
| 9,534,740 | B2 | 1/2017 | Tokarz et al. |
| 9,664,354 | B1 | 5/2017 | Dellock et al. |
| 9,707,310 | B2 | 7/2017 | Watanabe et al. |
| 10,006,619 | B1 | 6/2018 | Niemiec et al. |
| 10,221,857 | B2 | 3/2019 | Niemiec et al. |
| 10,247,191 | B2 | 4/2019 | Niemiec et al. |
| 10,316,141 | B2 | 6/2019 | Niemiec et al. |
| 10,337,716 | B2 | 7/2019 | Niemiec et al. |
| 10,393,357 | B2 | 8/2019 | Niemiec et al. |
| 10,670,026 | B2 | 6/2020 | Niemiec et al. |
| 10,753,626 | B2 | 8/2020 | Skelton |
| 10,808,964 | B2 | 10/2020 | Polidoro |
| 10,960,098 | B2 | 3/2021 | Zarcone et al. |
| 11,028,223 | B2 | 6/2021 | Niemiec et al. |
| 11,060,712 | B2 | 7/2021 | Niemiec et al. |
| 11,137,134 | B2 | 10/2021 | Niemiec et al. |
| 11,255,336 | B2 | 2/2022 | Niemiec et al. |
| 11,291,743 | B2 | 4/2022 | Polidoro |
| 11,293,665 | B2 | 4/2022 | Polidoro |
| 11,332,573 | B2 | 5/2022 | Niemiec et al. |
| 11,578,726 | B2 | 2/2023 | Niemiec et al. |
| 11,608,411 | B2 | 3/2023 | Niemiec et al. |
| 11,608,974 | B2 | 3/2023 | Niemiec et al. |
| 11,660,368 | B2 | 5/2023 | Polidoro |
| 11,859,624 | B2 | 1/2024 | Niemiec et al. |
| 11,993,677 | B2 | 5/2024 | Niemiec et al. |
| 12,016,983 | B2 | 6/2024 | Polidoro |
| 12,111,045 | B2 | 10/2024 | Niemiec et al. |
| 12,152,596 | B2 | 11/2024 | Niemiec et al. |
| 12,281,785 | B2 | 4/2025 | Niemiec et al. |
| 12,357,721 | B1 | 7/2025 | Niemiec et al. |
| 12,529,473 | B2 | 1/2026 | Niemiec et al. |
| 2002/0031460 | A1 | 3/2002 | Kulp |
| 2002/0155805 | A1 | 10/2002 | Paschke |
| 2004/0190281 | A1 | 9/2004 | Williams et al. |
| 2005/0099824 | A1 | 5/2005 | Dowling et al. |
| 2006/0000360 | A1 | 1/2006 | Shou |
| 2006/0086252 | A1 | 4/2006 | Huang |
| 2006/0152921 | A1 | 7/2006 | Welker |
| 2006/0177356 | A1 | 8/2006 | Miller |
| 2007/0253205 | A1 | 11/2007 | Welker |
| 2009/0049985 | A1 | 2/2009 | Leroux et al. |
| 2009/0129974 | A1 | 5/2009 | McEllen |
| 2009/0294688 | A1 | 12/2009 | Evans |
| 2010/0202932 | A1 | 8/2010 | Daville |
| 2011/0001060 | A1 | 1/2011 | Welker |
| 2011/0317407 | A1 | 12/2011 | Welker |
| 2012/0118150 | A1 | 5/2012 | Brizes et al. |
| 2013/0170215 | A1 | 7/2013 | Tokarz et al. |
| 2013/0256560 | A1 | 10/2013 | Yerby |
| 2013/0291735 | A1 | 11/2013 | Livchak et al. |
| 2014/0131595 | A1 | 5/2014 | Nathan et al. |
| 2015/0025300 | A1 | 1/2015 | Hill et al. |
| 2015/0062893 | A1 | 3/2015 | Lynn et al. |
| 2016/0033087 | A1 | 2/2016 | Tokarz et al. |
| 2017/0080373 | A1* | 3/2017 | Engelhard ............ B01D 46/448 |
| 2017/0321877 | A1 | 11/2017 | Polidoro |
| 2018/0296711 | A1 | 10/2018 | Brais et al. |
| 2020/0009286 | A1* | 1/2020 | Zarcone ............... A61N 5/0618 |
| 2020/0038542 | A1 | 2/2020 | Franklin et al. |
| 2020/0197550 | A1* | 6/2020 | Barron ............... H05K 7/20154 |
| 2020/0289698 | A1 | 9/2020 | Polidoro |
| 2021/0015959 | A1* | 1/2021 | Goseki ...................... A61L 9/20 |
| 2023/0039310 | A1 | 2/2023 | Baarman et al. |
| 2023/0293761 | A1 | 9/2023 | Polidoro |
| 2025/0312507 | A1 | 10/2025 | Niemiec et al. |

FOREIGN PATENT DOCUMENTS

| | | | |
|---|---|---|---|
| CA | 2762905 | A1 | 11/2010 |
| CA | 2898900 | A1 | 1/2016 |
| CA | 2762905 | C | 3/2018 |
| CA | 3163464 | | 7/2021 |
| CN | 1475285 | | 2/2004 |
| CN | 201437947 | U | 4/2010 |
| CN | 102483214 | | 5/2012 |
| CN | 103962346 | | 8/2014 |
| CN | 204943799 | U | 1/2016 |
| CN | 204951721 | | 1/2016 |
| CN | 102483214 | B | 2/2016 |
| CN | 106847663 | | 6/2017 |
| CN | 206434609 | U | 8/2017 |
| CN | 198568626 | A | 4/2019 |
| CN | 209039502 | U | 6/2019 |
| CN | 214415870 | | 10/2021 |
| DE | 10-2013-102121 | A1 | 9/2014 |
| EP | 2433048 | A1 | 3/2012 |
| EP | 2433048 | A4 | 1/2013 |
| EP | 2881126 | A1 | 6/2015 |
| GB | 2468504 | A | 9/2010 |
| GB | 2515842 | A | 1/2015 |
| JP | S63-85245 | | 6/1988 |
| JP | H01-170242 | | 12/1989 |
| JP | H01-170242 | U | 12/1989 |
| JP | H03-18847 | | 2/1991 |
| JP | H09243102 | A | 9/1997 |
| JP | 2004108685 | A | 4/2004 |
| JP | 2012-527302 | | 11/2012 |
| JP | 2014-138869 | | 7/2014 |
| JP | 5921429 | B2 | 5/2016 |
| JP | 2017-098085 | A | 6/2017 |
| JP | 2017-528258 | | 9/2017 |
| JP | 2018-130131 | | 8/2018 |
| KR | 2012-0060944 | A | 6/2012 |
| KR | 2012-0076870 | | 7/2012 |
| KR | 20120074746 | A | 7/2012 |
| KR | 10-10346576 | B1 | 1/2014 |
| KR | 2015-0032344 | A | 3/2015 |
| KR | 10-1533225 | B1 | 7/2015 |
| KR | 10-1586990 | B1 | 1/2016 |
| KR | 20160015084 | A | 2/2016 |
| MX | 2011012415 | A | 4/2012 |
| WO | 2010/093796 | | 8/2010 |
| WO | 2010/134991 | A1 | 11/2010 |

(56) References Cited

FOREIGN PATENT DOCUMENTS

| | | |
|---|---|---|
| WO | 2016/190967 | 10/2019 |
| WO | 2019/190967 | 10/2019 |
| ZA | 201109352 B | 8/2012 |

OTHER PUBLICATIONS

"An Overview of our Light Shaping Diffusers", Luminit Light Shaping Solutions, copyright 2019, downloaded as of Jan. 3, 2020, at https://www.luminitco.com/products/light-shaping-diffusers, pp. 1-3.

Luz Negra Linear lighting specialists, catalog downloaded as of Jan. 3, 2020, at http://thelightinggallery.co.uk/wp-content/uploads/Catalogue/Luznegra/Luznegra.pdf, pp. 1-292.

Neubauer, A. et al., "Simple down conversion nano-crystal coatings for enhancing Silicon-solar cells efficiency", AIMS Materials Science, vol. 3, Issue 3, published Sep. 6, 2016, pp. 1256-1265.

Kumi, D.O. et al., "Ultraviolet to visible down conversion of SiO2—Ce3+, Tb3+ nanospheres-poly-EVA films for solar cell application", Physica B: Condensed Matter, vol. 576, Jan. 1, 2020, downloaded at https://www.sciencedirect.com/science/article/abs/pii/S0921452619306179, Abstract only.

Kim, J., "Converting Visible Light to UVC: Lanthanide Upconversion Nano-Phosphors for Light-Activated Biocidal Surface Development", Georgia Tech Research Corporation, downloaded at https://grantome.com/grant/NSF/CBET-1033866, Abstract only, available at least as of Sep. 9, 2018.

Cates, E.L. et al., "Converting Visible Light into UVC: Microbial Inactivation by Pr3+-Activated Upconversion Materials", Apr. 15, 2011, downloaded at https://pubmed.ncbi.nlm.nih.gov/21428395/, Abstract only.

Invitation to Pay Additional Fees for International Application No. PCT/US2021/012013 mailed Mar. 9, 2021.

International Search Report and the Written Opinion of the International Searching Authority for International Application No. PCT/US2021/012013 mailed May 3, 2021.

International Search Report and the Written Opinion of the International Searching Authority for international application No. PCT/US2023/015449 mailed Aug. 17, 2023.

Vidashield website—Technology—available at https://web.archive.org/web/20160702160712/http:/vidashield.com/technology.html and available at least as of Jul. 2, 2016, pp. 1-2.

Vidashield website—Products—available at https://web.archive.org/web/20160630101504/http://vidashield.com/products.html and available at least as of Jun. 30, 2016, pp. 1-2.

Vidashield—Installation and Operating Manual—available at https://web.archive.org/web/20160717152420/http://vidashield.com/files/vs-installation-operation.pdf and available at least as of Jul. 17, 2016, pp. 1-13.

Vidashield—Product Flyer—available at https://web.archive.org/web/20160717150653/http://vidashield.com/files/VidaShield-2Page.pdf and available at least as of Jul. 17, 2016, pp. 1-2.

Vidashield—Product Brochure—available at https://web.archive.org/web/20160717150658/http://vidashield.com/files/VidaShield-Trifold.pdf and available at least as of Jul. 17, 2016, pp. 1-6.

Vidashield—VS02 Model Spec Sheet—available at https://web.archive.org/web/20160705144713/http://vidashield.com/files/VS02.pdf and available at least as of Jul. 5, 2016, p. 1.

Vidashield—VS03 Model Spec Sheet—available at https://web.archive.org/web/20160804101125/http://vidashield.com/files/VS03.pdf and available at least as of Aug. 4, 2016, p. 1.

Vidashield—Product Performance Report—available at https://web.archive.org/web/20160717152441/http://vidashield.com/files/whitepaper/dr-kowalski-vidashield-final-report.pdf and available at least as of Jul. 16, 2016, pp. 1-22.

Vidashield website—Product Distributors—available at https://web.archive.org/web/20160702175909/http://vidashield.com/about.html#us-distributors and available at least as of Jul. 2, 2016, pp. 1-2.

Vidashield website—Product Video—available at https://www.youtube.com/watch?v=7aY3ez-5Jdg and available at least as of Aug. 16, 2016, pp. 1-11.

HRMS, "A Ceiling Light and Air Disinfection System to Improve Indoor Air Quality Owner's Manual", available at least as of Jan. 3, 2020, pp. 1-36.

Chevrefils, G. et al., "UV Dose Required to Achieve Incremental Log Inactivation of Bacteria, Protozoa and Viruses", International Ultraviolet Association (IUVA) News, Mar. 2006, vol. 8, No. 1, pp. 38-45.

Malayeri, A.H. et al., "Fluence (UV Dose) Required to Achieve Incremental Log Inactivation of Bacteria, Protozoa, Viruses and Algae", Internal Ultraviolet Association (IUVA) News, Sep. 2016, pp. 1-41.

VidaShield Maintenance Video, available at https://www.youtube.com/watch?v=EPdnuNN355s, screen shots at 1:20 and 1:46, Oct. 20, 2016.

VidaShield Installation Video, available at: https://www.youtube.com/watch?v=DmFWq6blgDU, screen shots at 1:16, 1:28, 1:37, 1:47,2:04, 2:05, Oct. 20, 2016.

* cited by examiner

Disinfection Control System

SYSTEM AND METHOD OF DISINFECTION

FIELD OF INVENTION

The present disclosure relates generally to disinfection systems, and more particularly to a lighting fixture for disinfecting air.

BACKGROUND

Infection by a foreign organism, such as bacteria, viruses, fungi, or parasites, can be acquired in a variety of ways. But once acquired, the infection, if harmful, may colonize and result in illness. The immune system of the infected host (e.g., the person) may react to the infection and attempt to kill or neutralize the foreign organism. However, in some cases, the immune system may be insufficient to completely neutralize the infection, and hospitalization may be necessary for survival. For these and other reasons, infectious disease prevention is conventionally preferred over reliance solely on the immune system of the infected host.

Conventional efforts to prevent spread of infectious disease often involve manual disinfection techniques, such as wiping down or washing surfaces that may harbor foreign organisms. Because infectious diseases can be spread in a variety of ways, such as via direct contact from person to person, manual disinfection techniques can be time and labor intensive. For example, indirect contact from an infected person to an environmental feature and then to another person who contacts the contaminated environmental feature is a common mode of infection. Because there are numerous surfaces in the environment, it is considered laborious and time intensive to decontaminate all or substantially all surfaces in the environment, essentially making such decontamination impractical in many cases. As another example, air borne pathogens from an infected person can make their way into areas that are inaccessible to manual disinfection techniques. It is also known that contact pathogens can be airborne on the typical airborne particulates.

The room environments, such as hospital rooms, include air and surfaces that can become contaminated. It can be labor intensive to manually decontaminate such environments due to the volume of air and the number and variety of surfaces (e.g., nooks and crannies created by presence of objects in the room). The HVAC system for a room is particularly labor intensive to decontaminate and is typically mixing and distributing particulates. Additionally, or alternatively, in hospital environments (e.g., a patient room), the number and frequency of visitors and potential pathogens increases the likelihood of air and surface contamination, again increasing the labor and time to effectively decontaminate such surfaces with conventional techniques. For these and other reasons, conventional techniques fail to enable decontamination of room environments in a practical manner.

Conventional disinfection techniques for hospital rooms involve transporting a mobile UV lighting assembly in the room. The mobile UV lighting assembly is positioned within the room and activated for a period of time considered sufficient to disinfect the room. The mobile UV lighting assembly is then removed from the room and transported to storage or to another room for use. This process can be laborious due to the effort to transport and move the assembly and the effort to track a schedule for use of the assembly across several rooms.

SUMMARY

The present disclosure in accordance with one embodiment provides a light fixture that fits within a conventional ceiling opening for tiles and lighting fixtures. The light fixture may include a general lighting fixture combined with a UVC lighting fixture. The UVC lighting may be in a reactor that disinfects the air with the target dosage and provides a precision multi part reflector system that directs the light within a narrow opening to reach out from the primary fixture through an offset opening and provide a UVC dose to the ceiling. This reflector and baffle system may be configured to limit human exposure to provide a thin plane of light to travel along the surface. The air treatment system may contain a separate reactor and lamp from the surface disinfection or may utilize a transparent film to enable one UVC light source to be used for the air disinfection reactor and feed the surface treatment reflector system.

A system and method in accordance with one embodiment may include a light fixture configured to be disposed within a room and operable to provide visible light for the room and air disinfection via application of UV light to air flowing through an air treatment chamber. In one embodiment, one or more baffles may be disposed within the air chamber to substantially prevent UV light from leaking past the one or more baffles into the room. In one embodiment, a UV light regulator may be provided to selectively control an amount of UV light directed into the room.

In one embodiment, a fixture for disinfecting air within a room is provided. The fixture may include a support member operable to facilitate mounting the fixture to a surface, and a germicidal light source operable to generate UV light. The fixture may include a UV treatment chamber having an untreated air inlet and a treated air outlet, and an air treatment region operable to receive air from the untreated air inlet and to direct air to the treated air outlet. The UV light from the germicidal light source may be directed to the air treatment region.

The fixture may include one or more baffles operable to substantially prevent leakage of the UV light from the UV treatment chamber into the room through the untreated air inlet and the treated air outlet. The fixture may include a visible light source operable to generate visible light for illuminating the room.

In one embodiment, the fixture may include a UV light regulator in light communication with the germicidal light source. The UV light regulator may be operable to selectively control an amount of the UV light directed into the room from the germicidal light source.

In one embodiment, a fixture for disinfecting air within a room is provided with a support member operable to facilitate mounting the fixture to a surface and a germicidal light source operable to generate UV light. The fixture may include a UV treatment chamber having an untreated air inlet and a treated air outlet, and an air treatment region operable to receive air from the untreated air inlet and to direct air to the treated air outlet. The UV light from the germicidal light source may be directed to the air treatment region.

The fixture may include a visible light source operable to generate visible light for illuminating the room, and a UV light regulator in light communication with the germicidal light source. The UV light regulator may be operable to selectively control an amount of the UV light directed into the room from the germicidal light source.

In one embodiment, the UV light regulator may include a plurality of effective apertures available for UV light transmission to the room from the germicidal light source, where each of the effective apertures includes a stationary window and a slidable window.

The UV light regulator, in one embodiment, is operable to obtain occupancy information pertaining to whether any occupants are present in the room, where the UV light regulator is operable to selectively provide the UV light into the room based on the occupancy information being indicative that no occupants are present in the room.

A fixture for disinfecting air within a room is provided in accordance with one embodiment. The fixture may include a support member operable to facilitate mounting the fixture to a surface, and a germicidal light source operable to generate UV light. The fixture may include a first reflector configured to direct the UV light within a UV light region to the target surface, the UV light region being defined by the target surface, and an opposing boundary line that is parallel to or converges with the target surface.

In one embodiment, the fixture may include a second reflector configured to direct the UV light toward the first reflector, where the germicidal light source is positioned to direct light toward both a region within the treatment chamber and the second reflector.

In one embodiment, a system is provided to utilize human counting sensors, air disinfection devices, surface disinfection devices, and consolidated controls to compensate for human biological deposits within an environment for active pathogen reduction.

These and other advantages and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

DESCRIPTION

A system and method in accordance with one embodiment may include a light fixture configured to be disposed within a room and operable to provide visible light for the room and air disinfection via application of UV light to air flowing through an air treatment chamber. In one embodiment, one or more baffles may be disposed within the air chamber to substantially prevent UV light from leaking past the one or more baffles into the room. In one embodiment, a UV light regulator may be provided to selectively control an amount of UV light directed into the room.

It is to be understood that, although the illustrated embodiments of the present disclosure focus on the light fixture 100 being attached to a structure of the room, the present disclosure is not limited to this configuration. In one embodiment, the light fixture 100 may not be a fixture that is attached to a structure of the room, and instead may be a light assembly that can be placed within the room. For instance, the light assembly may be a mobile light or a stand-alone light assembly that can be positioned semi-permanently in the room in a manner similar to placement of a house lamp having a base disposed on a floor or object in a room.

I. Overview

Figure 1:
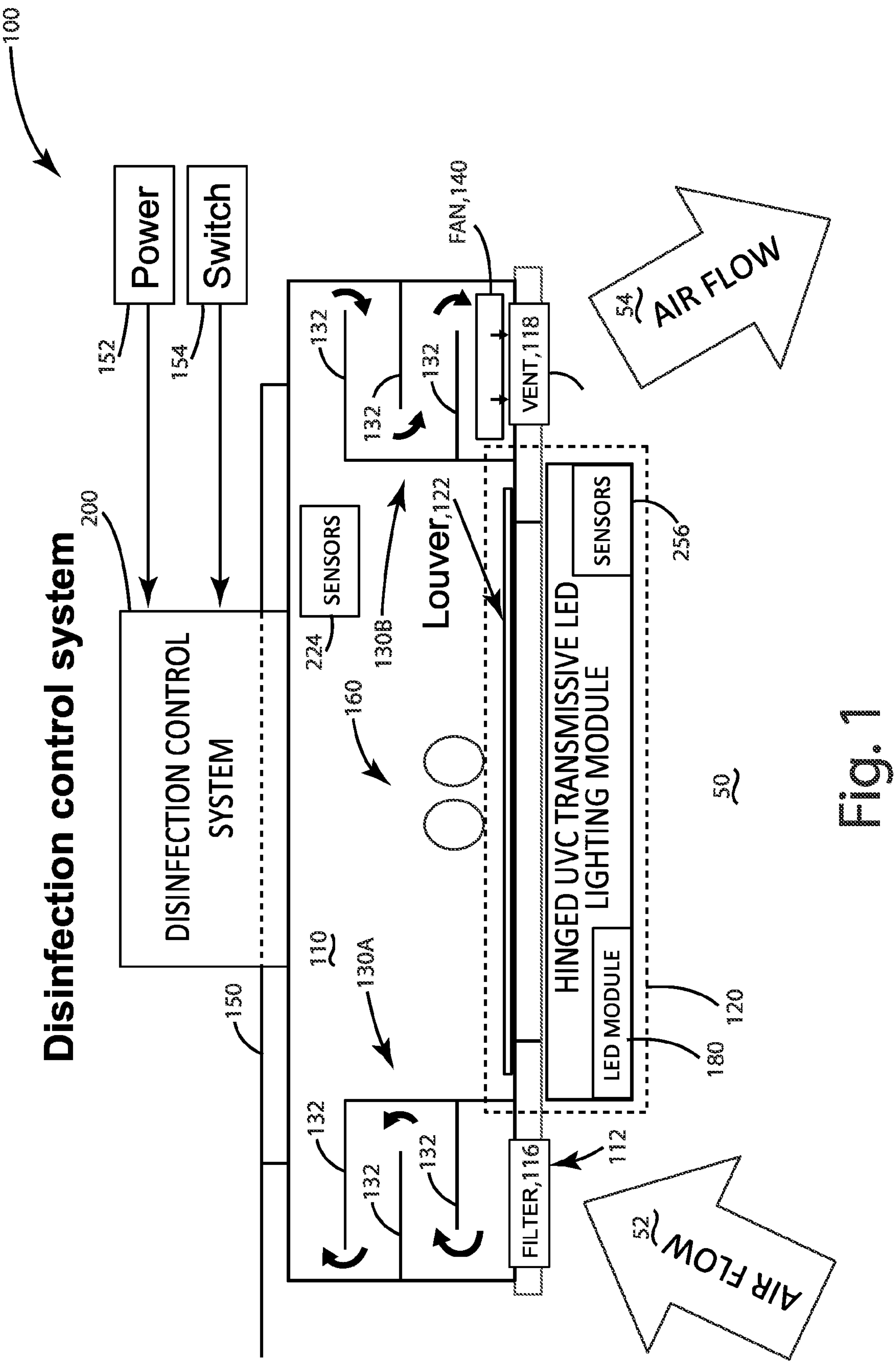
FIG. 1 shows a representative view of a light fixture in accordance with one embodiment of the present disclosure.

A light fixture in accordance with one embodiment of the present disclosure is shown in FIG. 1 and generally designated 100. The light fixture 100 may include a support member 150 operable to facilitate mounting the light fixture 100 to a surface. The surface may be the exposed surface of an interior wall of a room or a surface interior to the wall, such as a wall stud that is hidden from view. The light fixture 100 may receive power from a power source 152, and may be connected to the power source 152 in a variety of ways depending on the application, such as by direct wiring or via connection to an outlet socket. The light fixture 100 in one embodiment may include a control system 200 configured to control operation of the light fixture 100 and components thereof.

The light fixture 100 in one embodiment may include a visible light module 180 operable to supply visible light to a room area 50 of the room. It is noted that the visible light module 180 may be absent in one or more embodiments described herein. It is also noted that, for purposes of disclosure, the light fixture 100 is described in connection with having one or more components in the illustrated embodiment; it is to be understood that one or more components described herein in the light fixture 100 may be absent from the light fixture 100 and that any combination of components described herein may be incorporated into the light fixture 100.

The visible light module 180 may include a plurality of LEDs and an LED driver circuit operable to supply power to the plurality of LEDs for generating visible light sufficient for illuminating the room area 50. The visible light module 180, in the illustrated embodiment of FIG. 1, is shown integral to the UV light regulator 120 (which may form a door or removal access panel to the treatment chamber 110); For instance, the UV light regulator 120 may be a movable panel or door with edge lighting (e.g., lighting, such as one or more LEDs, disposed about at least a portion of the perimeter of the UV light regulator 120 and configured to direct light from the perimeter through the UV light regulator 120). The visible light from the edge lighting may be directed from within the UV light regulator 120 ultimately toward the room area 50. The present disclosure is not limited to the visible light module 180 being integral to the UV light regulator 120. For example, the visible light module 180 may be separate from the UV light regulator 120.

In one embodiment, the light fixture 100 may be controlled by a switch 154, which may be disposed remotely from the light fixture 100. The switch 154 may be operable to control supply of power to a subset of components of the light fixture 100. For instance, the switch 154 may be coupled to a control system 200 of the light fixture 100 that enables or disables activation of a visible light source for the room based on the state of the switch 154. Other circuitry and components of the light fixture 100 may remain active or inactive regardless of the state of the switch 154. Such circuitry or components, for instance, may be coupled to power from the power source 152 separate from the state of the switch 154, or under control from the control system described herein.

Alternatively, the switch 154 may be operable to selectively control supply of all power from the power source 152 to the light fixture 100. For instance, the switch 154 may be operable to disconnect or connect the power source 152 to the light fixture 100. This control may be provided via a wired or wireless interlace, and can be driven thru BACNET, Ethernet or other control systems. Systems coupled to the control system can be configured to allow dimming, zone control and other programmable features based on communications transmitted via one or more digital communications protocols.

The light fixture 100 may include a treatment chamber 110 through which air may be directed and in which the air may be treated with UV light from a UV light source 160. The UV light source 160 may be a germicidal light source operable to generate the UV light in response to being supplied power from the power source 152. For example, the UV light source 160 may be a UV-C source, such as a cold cathode lamp, a low pressure mercury lamp, or UV-C light emitting diodes.

The power applied to the UV light source 160 may be a conditioned form of the power from the power source 152. For instance, the power source 152 may be operable to supply AC power. The light fixture 100 may include circuitry to condition this AC power into DC power sufficient to operate the UV light source 160. The DC power may be constant or pulsed depending on the operating specification and the target parameters for the UV light source 160. In DC pulsed configurations, the power may be variable such as by varying the DC pulse between 90% to 30% to supply power in accordance with a target operating parameter.

In one embodiment, untreated air 52 may enter the treatment chamber 110 via an air inlet 112, and treated air 54 may exit the treatment chamber 110 via an air outlet 114. The air inlet 112 may be in fluid communication with a filter assembly 116, which may be configured to filter particulates from the untreated air 52 prior to being treated by UV light in the treatment chamber 110. Removal and replacement of the filter assembly 116 may be conducted on a periodic basis to prevent substantial clogging of the filter assembly 116.

In one embodiment, the filter assembly 116 may be disposed such that one or both sides of the filter assembly 116 are in a path of light from the UV light source 160. This way, UV light may be directed to the filter assembly 116 to decontaminate all or a portion of the filter assembly 116. The UV light applied to the filter assembly 116 may be selectively applied, or the filter assembly 116 may be disposed to receive light from the UV light source 160 while the UV light source 160 is active.

As discussed herein, treated air 54 may exit the treatment chamber 110 via an air outlet 114. The air outlet 114 may include a vent 118 configured to allow airflow therethrough at a flow rate sufficiently greater than a flow rate of the treated air 54. In other words, the vent 118 may be configured to substantially avoid restricting airflow through the treatment chamber 110. The vent 118 may include a plurality of openings each sized to substantially prevent entry of improper objects (e.g., hands and fingers) into the treatment chamber 110.

The treatment chamber 110 in one embodiment may include a baffle assembly, such as the air inlet baffle assembly 130A and the air outlet baffle assembly 130B, operable to substantially prevent leakage of UV light from the air inlet 112 and air outlet 114 of the treatment chamber 110. Each baffle assembly 130A, 1308 may include a plurality of baffles 132 arranged to allow airflow through the treatment chamber 110 without substantially restricting or affecting the target flow rate of air. For instance, if the light fixture 100 is configured to treat air at a rate of 300 CFM, the baffles 132 of each baffle assembly 130A, 1308 may be arranged to allow airflow at a rate greater than 300 CFM. Using this same target airflow rate of 300 CFM, it is noted that in one embodiment, the treatment chamber 110 may be constructed to allow airflow at a rate greater than the target airflow rate (e.g., greater than 300 CFM). A fan assembly 140, as described herein, may be selected or operated to move air at the target flow rate.

In the illustrated embodiment, the plurality of baffles 132 of each baffle assembly 130A, 1308 may be disposed to allow airflow through each baffle assembly 130A, 130B in a serpentine manner. This configuration may substantially prevent passage of UV light through the baffle assembly 130A, 1308 and out through the respective air inlet 112 or air outlet 114.

The baffles 132, in one embodiment, may facilitate protecting the filter assembly 116 from contact with UV light from the UV light source 160. This configuration may substantially prevent damage or breakdown of the filter assembly 116 due to exposure to UV light, potentially lengthening the viable life of the filter assembly 116.

In one embodiment, one or both of the baffle assemblies 130A, 1308 may be absent from the light fixture 100. One or both of the air inlet 112 and the air outlet 114 may be configured in such embodiments to substantially prevent leakage of UV light from the treatment chamber 110.

As described herein, the light fixture 100 may include a UV light regulator 120 and general lighting lens and system. The baffle assemblies 130A, 130B may form part of the UV light regulator 120 to control transmission of UV light from the treatment chamber 110 into the room area 50. Controlling transmission of UV light may include directing UV light from one or more regions of the light fixture 100 and substantially preventing light transmission or leakage from one or more other regions of the light fixture 100.

The light fixture 100 may include a fan assembly 140 operable to direct air through the treatment chamber 110 from the air inlet 112 to the air outlet 114. In the illustrated embodiment, the fan assembly 140 is disposed proximal to the air outlet 114; however, it is to be understood the present disclosure is not so limited. The fan assembly 140 may be disposed or provided in a different position to direct air through the treatment chamber 110. For instance, the fan assembly 140 may be disposed proximal to the air inlet 112 to direct air through the treatment chamber 110.

The fan assembly 140 may include a fan operable to direct air through the treatment chamber 110 at a target flow rate for disinfection or decontamination of the air via application of UV light within the treatment chamber 110. As an example, the target flow rate may be 50 CFM. In one embodiment, the fan assembly 140 may be variable such that a flow rate of air through the treatment chamber 110 may be increased or decreased under direction of a control system 200 of the light fixture 100. The increase of flow rate may also be digitally driven by environmental or other control factors derived from that environment or interactions thereof.

The light fixture 100 in the illustrated embodiment may include a control system 200 operable to direct operation of the light fixture 100 as described herein. For instance, the control system 200 may be configured to direct supply of power to the UV light source 160 to facilitate treatment of air flowing through the treatment chamber 110. As described herein, the control system 200 may be operably coupled to one or more sensors. The one or more sensors may be configured to sense a variety of information depending on the application. Example types of sensors include a passive infrared sensor (PIR sensor), a motion sensor, a contact center, a capacitive touch sensor, a USB input interlace, an accelerometer, a temperature sensor, an RFID reader, a UV regulator sensor, and a motor sensor. It is noted that some of these examples include overlapping capabilities, such as the PIR sensor and the motion sensor, and in embodiments where such capabilities are described, one or more of such example sensors may be provided for such sensor capabilities.

The control system 200 in the illustrated embodiment may be operable to selectively control application of UV light from the UV light source 160 to a room area 50. The control system 200 may obtain information indicative of whether the room area 50 is occupied by one or more persons, and based on such information being indicative that the room area 50 is unoccupied, the control system 200 may control the UV light regulator 120 to direct UV light from the UV light source 160 to the room area 50.

The control system 200 in the illustrated embodiment may also be operable to direct operation of the visible light module 180. For instance, the control system 200 may incorporate driver circuitry for supplying power to one or more lights (e.g., LEDs) of the visible light module 180. As another example, the control system 200 may include a communication interface (e.g., 120 or SPI) operable to communicate commands to driver circuitry incorporated into the visible light module 180 for controlling supply of power to the one or more lights. In one embodiment, a room with an air treatment and surface disinfection system may modulate the visible light with an ID to communicate this ID to other disinfecting systems and assets within the room.

The control system 200 may include any and all electrical circuitry and components to carry out the functions and algorithms described herein. Generally speaking, the control system 200 may include one or more microcontrollers, microprocessors, and/or other programmable electronics that are programmed to carry out the functions described herein. The control system 200 may additionally or alternatively include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware. Such components can be physically configured in any suitable manner, such as by mounting them to one or more circuit boards, or arranging them in other manners, whether combined into a single unit or distributed across multiple units. Such components may be physically distributed in different positions in the light fixture 100, or they may reside in a common location within the light fixture 100. When physically distributed, the components may communicate using any suitable serial or parallel communication protocol, such as, but not limited to, CAN, LIN, FireWire, I2C, RS-232, RS-485, and Universal Serial Bus (USB). In one embodiment, the control system local to a device (e.g., the light fixture 100) may also interacts with a cloud based control system, which may receive or transmit additional inputs obtained from external systems (e.g., other light fixtures or disinfection systems or environmental systems, or any combination thereof) to provide a greater view and understanding of the overall environment. The cloud based control system can also control a device directly based on additional protocols and information obtained from sensor data and other sources.

In one embodiment, the light fixture 100 may be operable to fit within a present ceiling opening for tiles and lighting fixtures. The light fixture 100 may have a general visible light component and be operable to retrofit in place of an existing conventional light fixture. The light fixture 100 may include a UV lighting aspect (e.g., UVC lighting) as described herein. The UV lighting may be provided in a reactor, such as a treatment chamber, that disinfects air with the target dosage. The UV lighting aspect may include a UV-C reactor vessel and reflectors with UV projection areas. The UV light may be directed, in one embodiment, by a precision multi-part reflector system that directs the UV light within a narrow opening to reach out from the light fixture 100 through an offset opening to provide a UV dose to the ceiling or another target surface. This reflector and baffle system may be configured to limit human exposure to UV light while providing a thin plane of light to travel along the target surface.

In one embodiment, the light fixture 100 may include an air treatment system that includes a reactor and UV light source that are separate from a reactor and UV light source provided for the surface disinfection of the target surface. Alternatively, the light fixture 100 may include a transparent film or light transmissive element that allows passage of light but not air. The light transmissive element may enable a UV light source of the air treatment system or the surface disinfection system to be used for feeding both the air disinfection reactor and feed the surface disinfection system (e.g., a surface treatment reflector system).

In one embodiment, airflow can change with HVAC and doors pressurizing the room. A system in accordance with one embodiment may measure the airflow and adjust UV disinfection intensity related to a table that has a flow vs intensity dosage chart. A control system may adjust for the duration of higher flow rates and also track the flow changes over time and sends that data to an external device. In one embodiment, pressure sensors or information obtained from HVAC sensors, or both, may provide data on flow path and potential contamination times and events. In hospital environments, sensor information, such as pressure sensor information or HVAC sensor information, or both, may enable tracking of door opening times and changes in areas adjacent to sterile zones.

In one embodiment, an air treatment system with surface disinfection and air disinfection may be provided. The system may include a hinged LED light fixture, a lamp or light source, and a reactor system for treating particles with UV light (e.g., UVC light). The air treatment reactor may include a fan, a UVC reactor, and a HEPA filter at the input. The air treatment system may include a particle sensor capable of sensing skin and dust particles. The air treatment system may monitor the life of the lamp(s) and the filter end-of-life timing. The system may be networked and capable of communicating information to external devices, such as end-of-life data and the sensor and room data. This data may include temperature, air pressure, light levels, air flow, filter end-of-life times, lamp end of life times, installed and replaced dates, hours of use total, hours of use since last filter, lamp changes, when the unit is opened for service, and how many times each day and each night the light is used. The light sensor may be used to detect daylight or room light levels. The light levels can be set as a threshold to prevent the disturbance of the patients when the room is dark. The floors may be treated during the lighted portion visits and daylight. Information obtained from one or more daylight sensors can also be used as a basis for energy savings controls, as well as understanding daylight patterns and adjusting operation based on such daylight patterns.

It is noted that, in one embodiment, the light fixture 100 may be opened for service. For instance the visible light module 180 may be pivoted out of the way to gain access to the UV light source 160 and to replace the UV light source 160.

II. Control System

Figure 2:
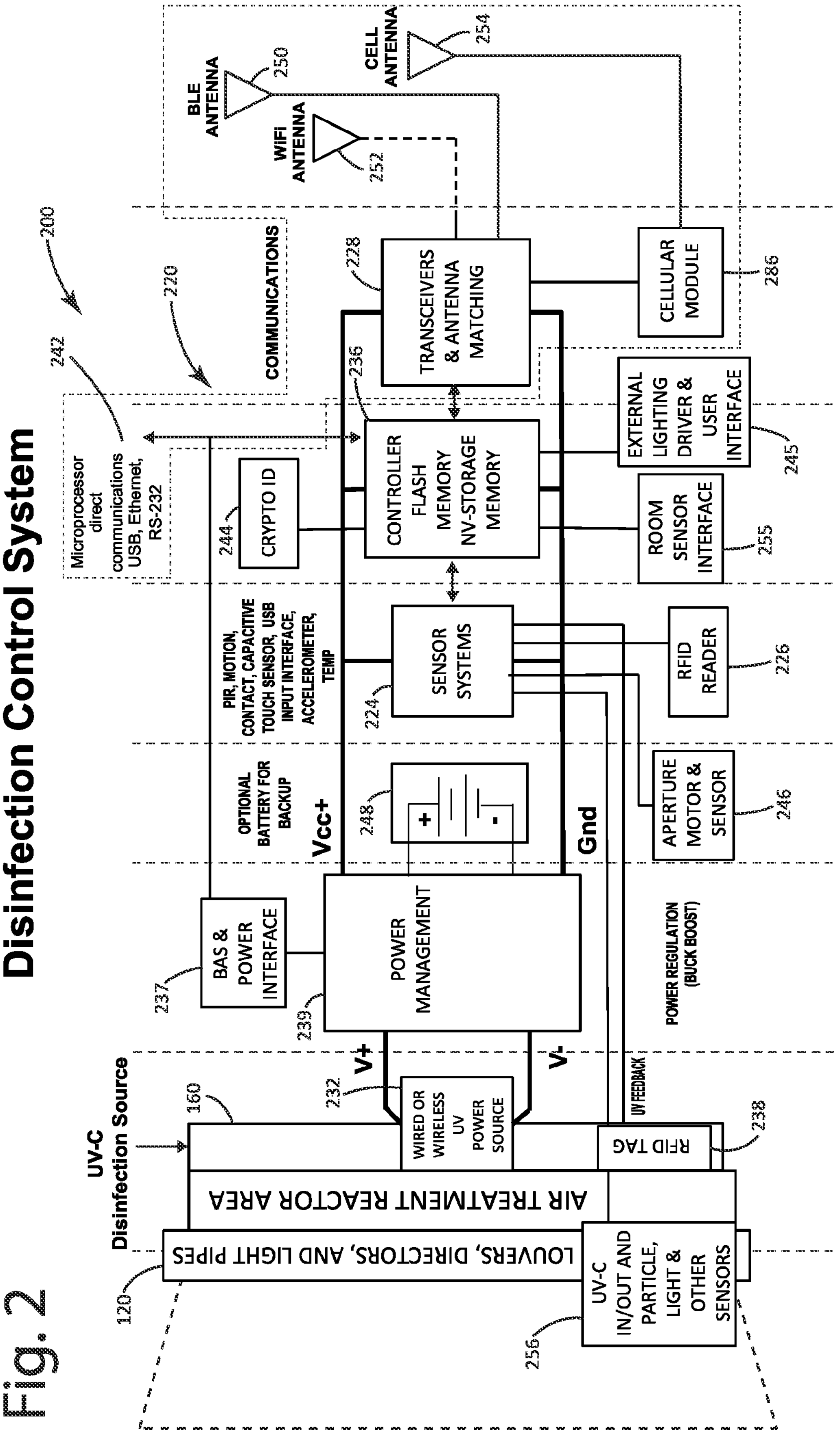
FIG. 2 shows a control system of the light fixture of FIG. 1 in accordance with one embodiment.

As described herein, the light fixture 100 in one embodiment may include a control system 200 configured to control operation of the light fixture 100 and components thereof. A control system 200 in accordance with one embodiment is shown in FIG. 2. In one embodiment, the control system 200 may be configured as an Internet-of Things ("IOT") hub or node within a network, as described herein. The control system 200 in one embodiment may be operable to detect and identify the location for terminal cleaning equipment.

The control system 200 may include power management capabilities and an optional battery management system for safety and emergency purposes. One or more sensors may be provided to detect in room conditions for general data usage and analytics as well as helping to inform the systems control of events and conditions for response. The system may include an industrial automation interlace for control and energy management. The control system may include a UVC sensor to understand dose and time for the air reactor and the surface treatment. Power management may include one or more of the following operations: delayed off, intermittent cycle scheduling, dimming, power monitoring, and accounting, and on/off control.

The control system 200 in the illustrated embodiment includes a UV light power source 232 (e.g., a UV-C power source) that enables UV intensity control and contact time control. The UV light source 160 may be any UV source capable of generating UV light at the target intensities, including UV-C light at the target intensities. The UV light power source 232 may be capable of controlling current and/or voltage supplied to the UV light source 160, and may provide such power in a variety of ways. For instance, the UV light power source 232 may supply power directly via wires to the UV light source 160, or the UV light power source 232 may supply power wirelessly to the UV light source 160. In the wireless configuration, the UV light power source 232 may include a primary capable of transmitting power wirelessly, and the UV light source 160 may include a secondary capable of receiving the wirelessly transmitted power.

The control system 200 of this embodiment may include a controller 236 capable of performing various functions pertaining to operation of the light fixture 100. The controller can be a low current microprocessor configured on a regulated rail. The microprocessor can be configured to monitor temperature (e.g. ambient, source, and local microprocessor temperature), accelerometer values, voltage and current sensors, as well as any other suitable sensors for use in conjunction with a microprocessor, or any combination thereof. The microprocessor module can also allow for external communications and interface.

In the illustrated embodiment, the controller 236 is coupled to a sensor system 224 that provides the control system 200 with various sensor inputs, such as PIR sensors, motion sensors, capacitive touch sensors, accelerometer and temperature sensors, and may provide an interface for RFID reader 226. The data collected by these sensors may assist in controlling operation of the control system 200 and in collecting data that may be relevant to tracking on infection-related events. The touch sensing aspect in accordance with one embodiment enables touch events to be used to trigger UV source activation, to interrupt disinfection cycles, and to provide valuable data in making dynamic adjustments to the UV parameters, such as cycle time and source intensity. The PIR sensor in one embodiment may enable heat and motion tracking. Additionally or alternatively, capacitive touch sensing may enable tracking touches of grab handles and non-switch surfaces.

The sensor system 224 in one embodiment may include a particle sensor capable of sensing information about particles present in the air that is external or internal, or both, with respect to the treatment chamber 110. The control system 200 may vary operation based on the particle information obtained from the particle sensor.

In one embodiment, the control system 200 may be coupled to a cloud system also as described herein as a cloud based control system 3602. The cloud system 3602 may obtain multiple particle sensor readings for an environment, and direct fan speeds and on times to treat a plume of particulates within a larger environment of multiple devices (e.g., multiple air pathogen reduction systems) in a connected pathogen reduction system.

The controller 236 in one embodiment may monitor the current and voltage of power supplied to the UV light source 160, and may determine whether the current and/or voltage are within preset ranges for proper operation and lamp diagnostics. UV light sources 160 can present open circuits, short circuits, or impedance changes causing different operating voltages. The controller 236 may identify such conditions based on the current and/or voltage and send information pertaining to such conditions to a remote network component, such as a network server on the cloud, as a service request. In one embodiment, the UV light power source 232 monitors the current and voltage to the UV light source 160 and feeds that information back to the controller 236. The controller 236 may also include volatile and and/or non-volatile storage memory. For example, the controller 236 may include flash memory.

In one embodiment, the UV light source 160 and control system 200 have integrated RFID capabilities. An RFID tag 238 disposed on the UV light source 160 may allow the controller 236 to uniquely identify the UV light source 160 using an RFID reader 226. This allows the control system 200 to properly validate the UV light source 160 and also allows new thresholds (e.g., operating currents and/or voltages and other operating parameters) to be transferred to the controller 236 for the particular UV light source 160 connected to the light fixture 100. These thresholds may change by manufacturer or lamp time and can also be changed over time as the controller 236 adapts and learns the operating parameters of the UV light source 160.

The UV light power source 232 in one embodiment includes an amplifier circuit, where an amplifier gain can be changed to increase or decrease intensity of the UV light source 160. The amplifier may change the voltage applied to the UV light power source 232 to within allowed thresholds. It is noted that higher thresholds or operating near the upper end of a voltage range of the UV light source 160 may adversely affect the life of the UV light source 160. The operating intensity thresholds, operating ranges, or other operating conditions for the UV light source 160 may also be pushed and saved to the RFID tag 238. For instance, the hours at each intensity level may be helpful to the controller 236 as it may accumulate the time at each intensity for the UV light source 160 to enable total end-of-life calculations. This information may be persistent to the RFID tag 238 of the UV light source 160 so that, if the UV light source 160 to another light fixture 100, that light fixture 100 can be aware of operating parameters and an end of life associated with the UV light source 160.

Figure 14:
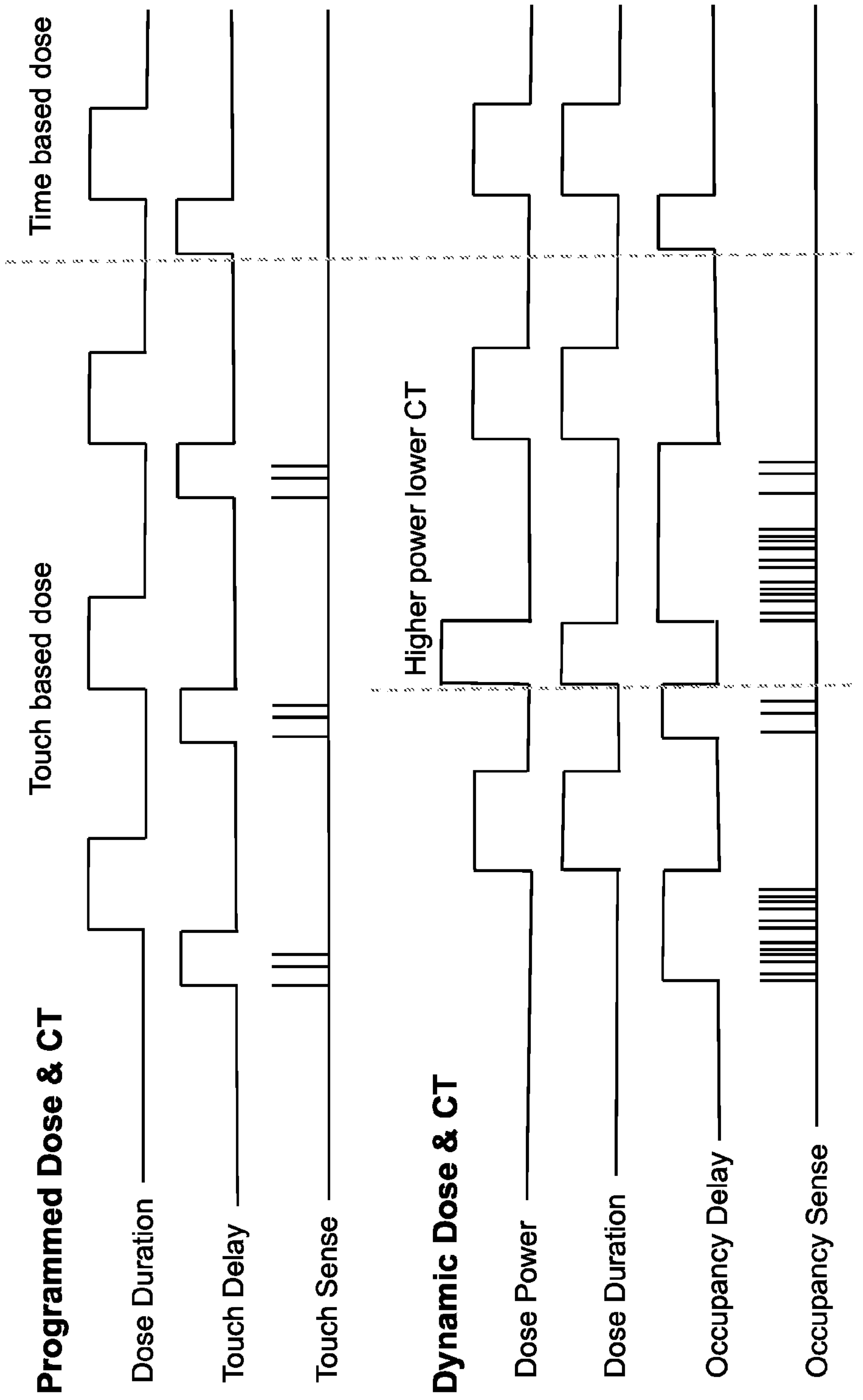
FIG. 14 shows a dosing based on status information (e.g., occupancy or touches) in accordance with one embodiment.
Figure 15:
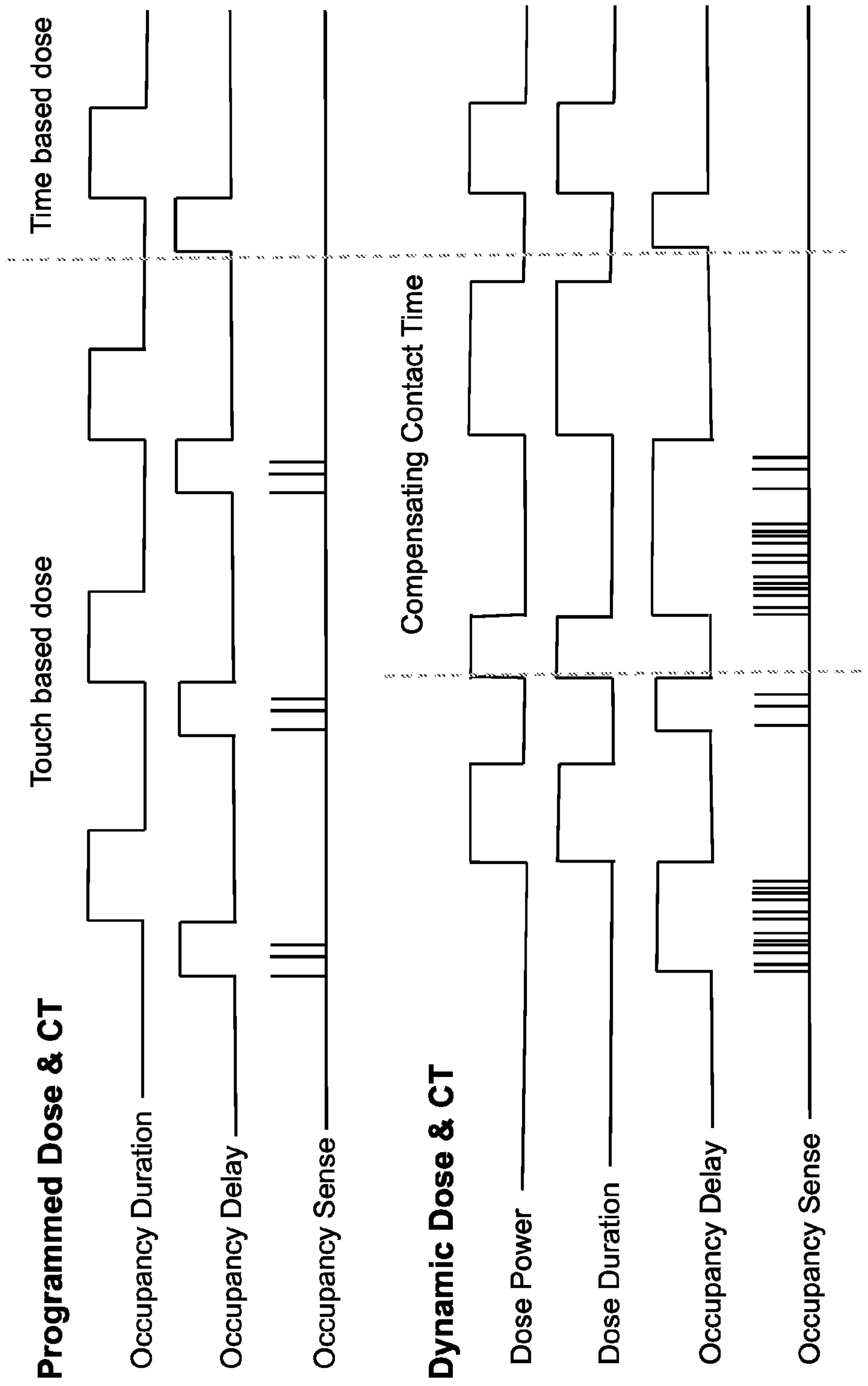
FIG. 15 shows a dosing based on status information (e.g., occupancy or touches) in accordance with one embodiment.
Figure 16:
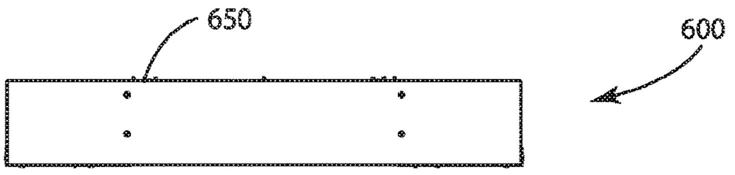
FIG. 16 shows a front view of a light fixture in accordance with one embodiment.
Figure 17:
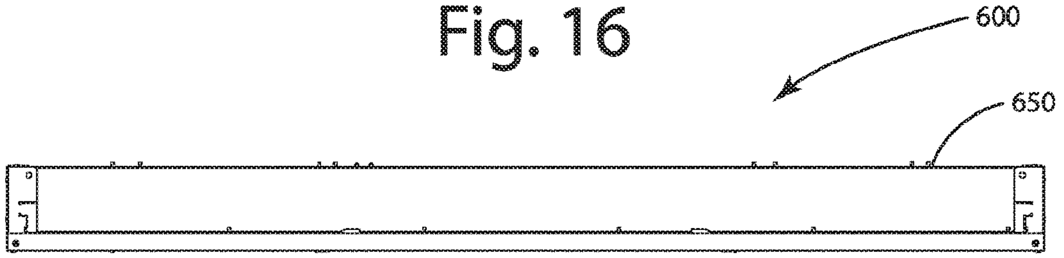
FIG. 17 shows a right side view of the light fixture of FIG. 16.
Figure 18:
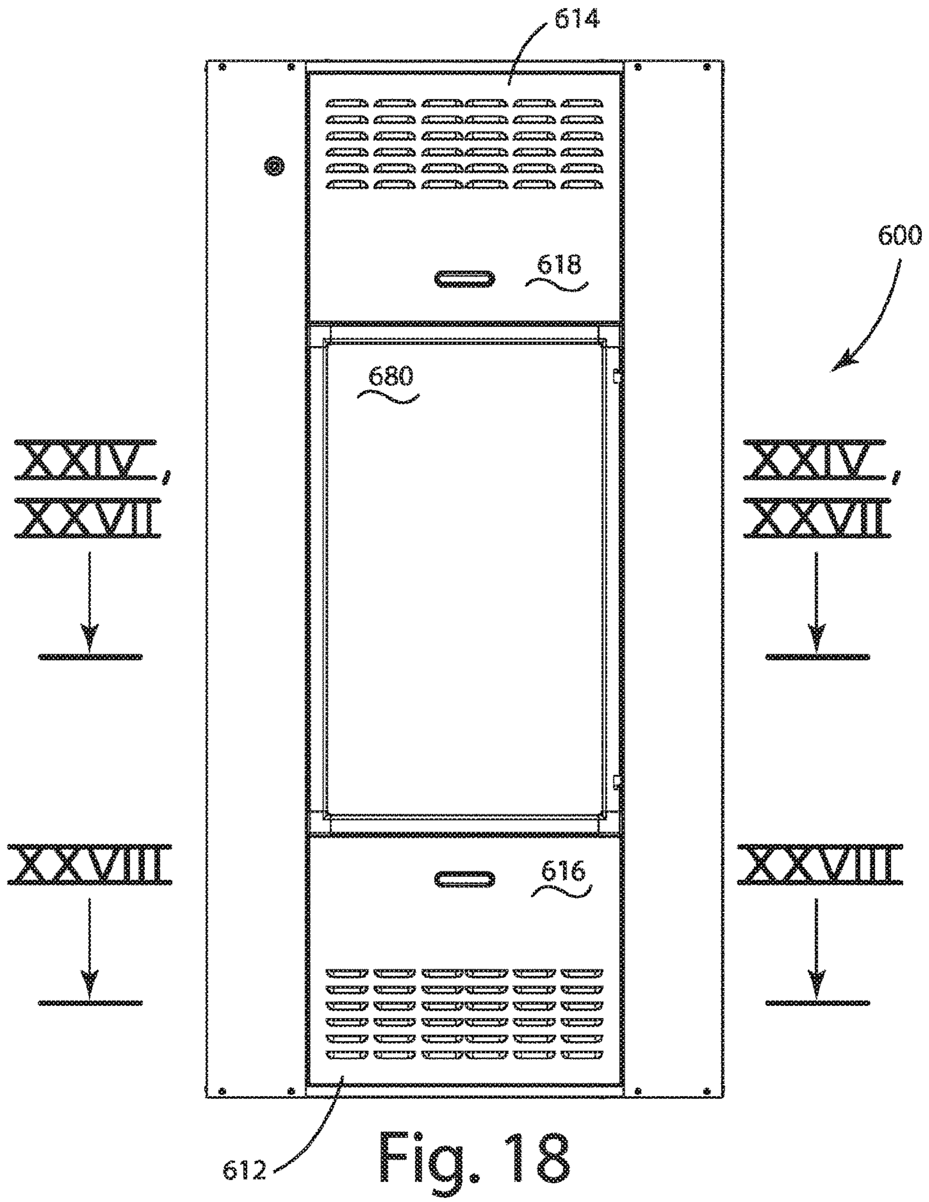
FIG. 18 shows a bottom view of the light fixture of FIG. 16.
Figure 19:
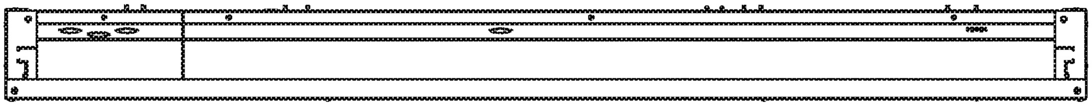
FIG. 19 shows a left side view of the light fixture of FIG. 16.
Figure 20:
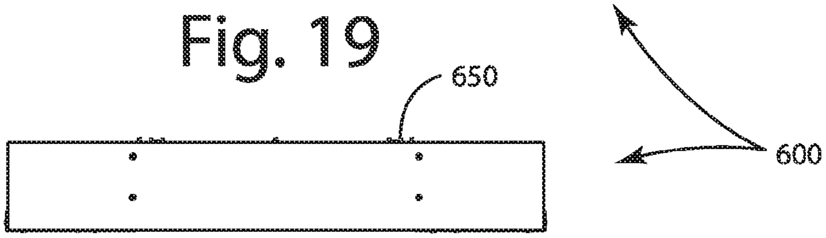
FIG. 20 shows a rear view of the light fixture of FIG. 16.
Figure 21:
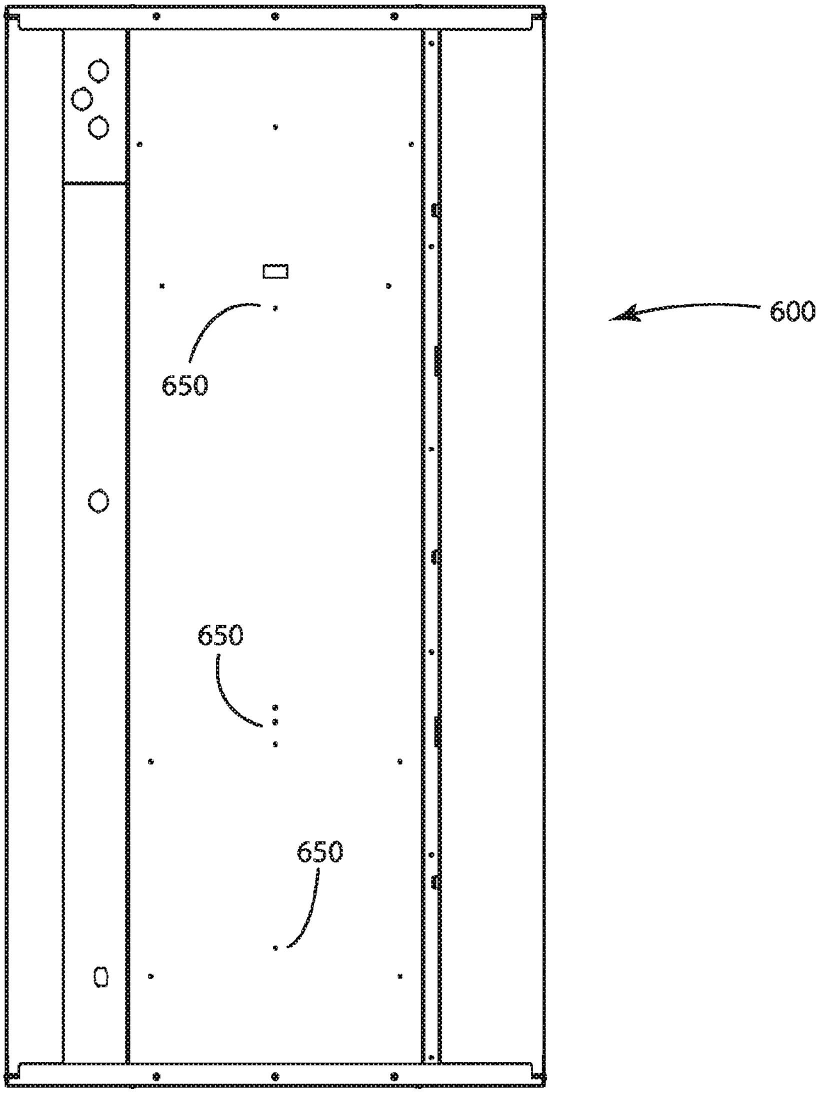
FIG. 21 shows a top view of the light fixture of FIG. 16.
Figure 22:
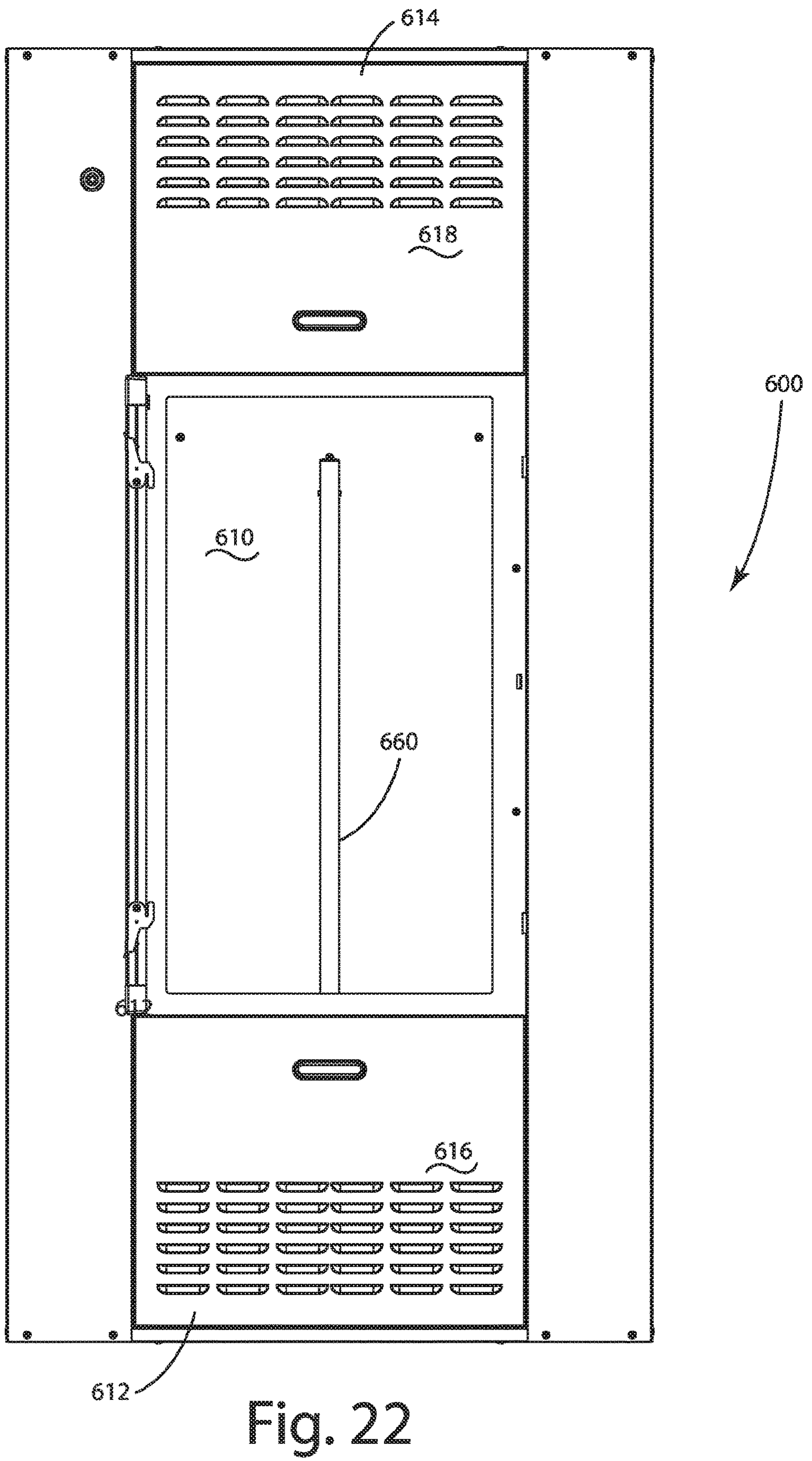
FIG. 22 shows a bottom view of the light fixture of FIG. 16 with a visible light module removed.

Adjusting and applying power to the UV light source 160 at controlled intervals may allow the controller 236 to control the UV power output. This may enable frequent in-and-out occupancy for the room area 50 to be treatment compensated dynamically. It is not often ideal to run at the highest intensity as it impacts the UV light source 160 with shorter life. With a lower intensity operation, longer duration "on" cycle times (or dose times) may be targeted to obtain adequate disinfection as shown in FIGS. 14 and 15.

Dynamic control may be utilized to increase dose momentarily during busy times. A running average of busy times and target dose changes can be preprogrammed and the controller 236 may then modify these dynamically as presence iterations change with respect to the room area 50. This may be directed locally by the control 200 or by a cloud interlace via a communication protocol.

An example of the algorithm involves first having a setting of the target dose. Each light fixture 100 may, for example, store a target dose in the form of intensity level and contact time at a calibrated distance for the room area 50. A communication interlace 220 of the control system 200 may be provided to receive information from and transmit information to external electronic devices. For instance, the communication interlace 220 may include a USB interlace 242 (or other wired communication interface, such as Ethernet or RS-232) or a BTLE interface (or other wireless communication interface) that can be configured to allow external electronic devices, such as a smartphone, tablet computer, or other mobile electronic device to automatically write UV parameters and other relevant values into the control system 200.

Figure 13:
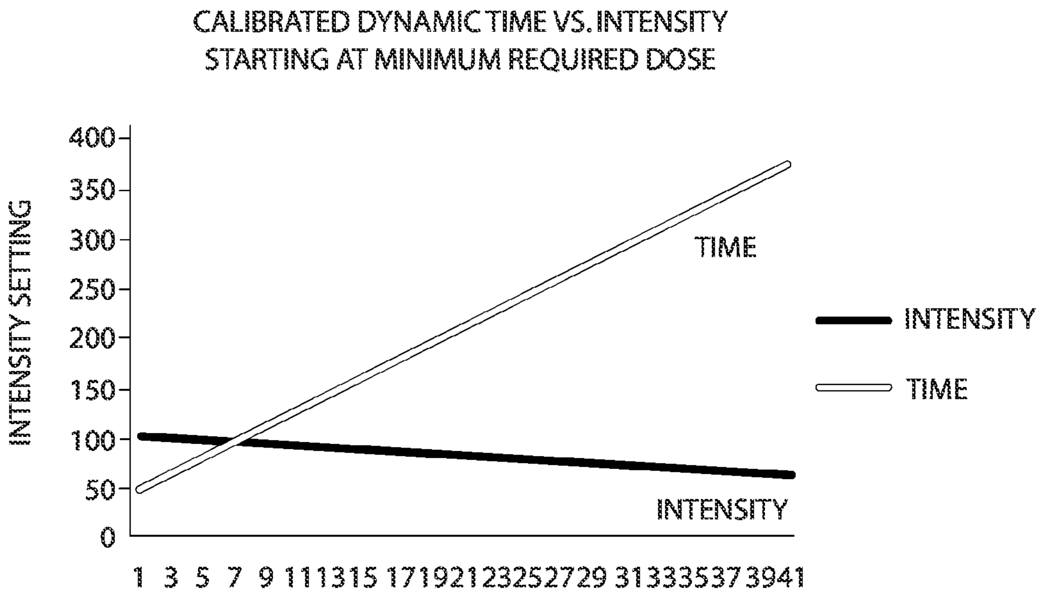
FIG. 13 shows a dynamic dose curve in accordance with one embodiment.

In some applications, the UV light source 160 is fixed at the specific distance from the target disinfection surface and a UV-C intensity meter is used to assure dose for that interval. This can be used to assure that every device has been calibrated to preset standards. Some UV light sources 160 are manufactured in glass rather than quartz and will not emit UV-C. This type of quality and output calibration can be used in the field and in the production facility. The OEMs manufacturing the device can assure proper installation configurations over many mounting options and distances with a go-no-go answer for limits of performance. The expected lamp life also changes dynamically as these minimum intensity expectations are set. An aging percentage may be added to these numbers to account for source degradation over the expected source life. The chart of FIG. 13 shows a typical curve calculated for the dynamic dose curve. The dose data vs. power may be defined and measured in the lab first, stored and averaged over life and then verified at the surface in testing. It is to be noted that the range or intensity span may be set and designed for optimal life for the UV light source 160 and is often over designed. The starting calibration values include the span of intensity. This sets the range of time allowed and may be limited by UV exposure limits, such as eye contact thresholds. In the case shown, the thresholds are set by OSHA standards for UV-C contact and exposure.

Figure 5:
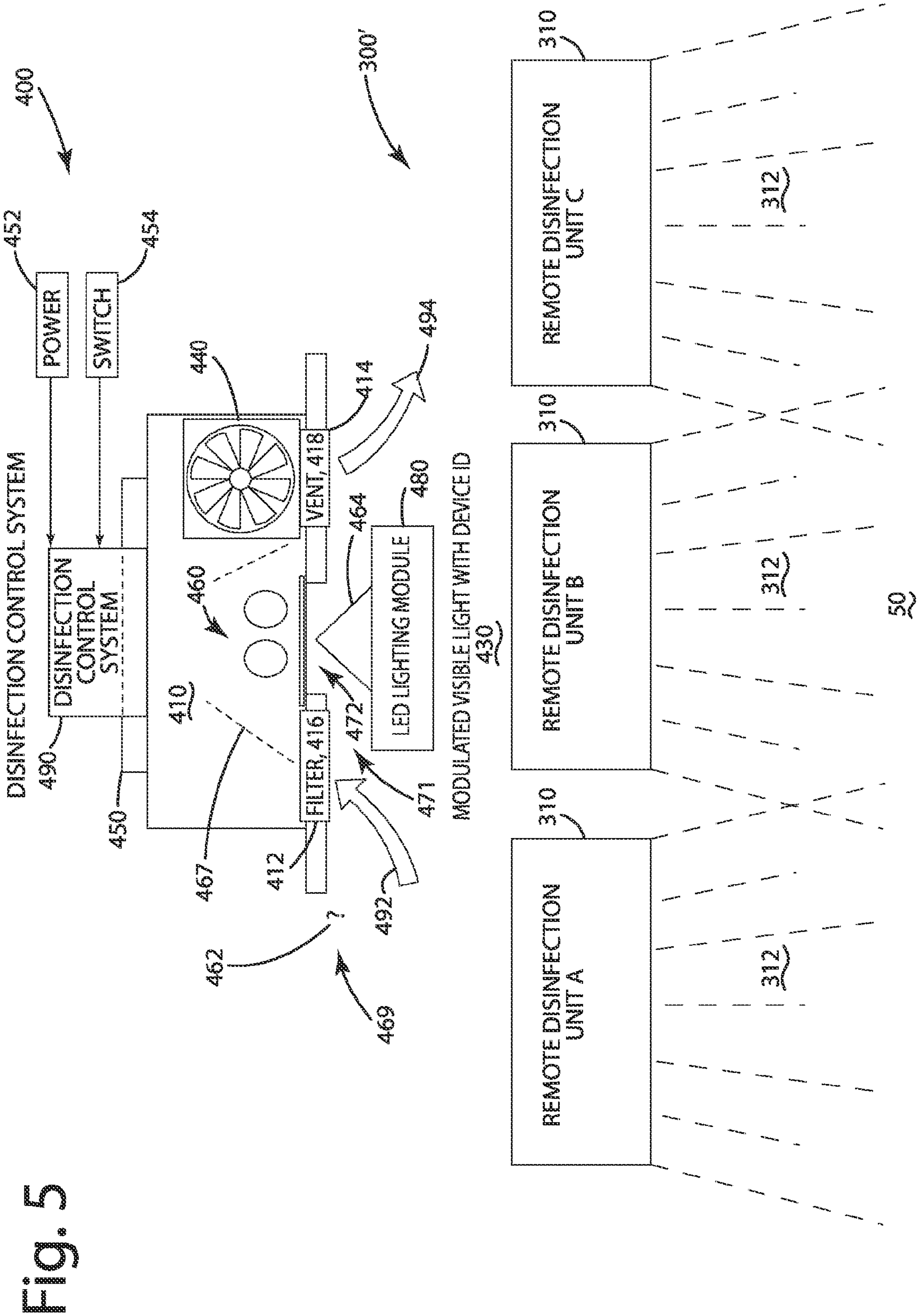
FIG. 5 depicts a light fixture and a disinfection system in accordance with one embodiment of the present disclosure.

In some applications, additional security-related components may be provided in the control system 200. For example, in the embodiment of FIG. 5, a crypto chip 244 is included to provide each unit with a unique ID. Other mechanisms for identifying each light fixture 100 may be provided. The security may also be augmented with a token and SSID for security purposes stored in non-volatile memory set up by installation staff through BTLE or USB program for WiFi interlace. This crypto chip 244 may be provided for an additional security measure and may be configured to create a disinfection and room occupation tracking device that can have the security conditions considered sufficient to write directly into an electronic medical record.

In one embodiment, the communication interlace 220 of the control system 200 has BTLE and/or Mesh capabilities. The mesh network can be Zigbee or BACNet to meet specific regulatory requirements or hospital specifications. In extreme monitoring solutions a cellular module 286 may be used to communicate the data to an external device (e.g., the cloud) as an alternative source of information gathering. As shown, the control system 200 may include transceivers and antenna matching circuitry 228 and a cellular module 286 that are coupled to corresponding antennas 252, 250, 254. The controller 236 may also have ports to allow directed wired connections, for example, using USB, Ethernet and RS-232 protocols.

In some applications, the control system 200 may have the ability to operate on battery power. The battery version may be provided with a battery 248, which may be the power source 152 for the light fixture 100. The battery-based system may be chargeable in a variety of ways, including wired and wireless charging configurations. The power storage may be sized for UV dose and interval, and may be connected to charging equipment or directly chargeable. It may also have various indicators for providing feedback to a user.

As noted above, the UV light source 160 (e.g., UV-C lamp) may have an RFID tag 238 and the control system 200 may have an RFID reader 226 to understand when the UV light source 160 has reached end-of-life to encourage appropriate use and maintenance. UV light sources 160 often have a life based on a number of hours as they self-destruct due to the nature of UV light, including UV-C light. The control system 200, for example, through the controller 236, may keep track of lamp "on time" by reading from and writing to memory resident on the RFID tag 238. The control system 200 may adjust the actual "on time" by a correlation factor to compensate for lamp intensity. For example, the control system 200 may increment the lamp life counter by less than the actual "on time" for operation that occurs when the lamp intensity is reduced and may increase the lamp life counter by more than the actual "on time" for operation when the lamp intensity is increased. The correlation factor (or intensity adjustment factor) may be provided by the lamp manufacturing, may be determined through tests of the UV light source 160, or may be estimated based on past experience.

The communication interlace 220 of the control system 200 may also have USB and Power over Ethernet ("POE") circuitry 237, which may enable usage without additional power cord requirements for this equipment. In one embodiment, the power management circuitry 239 may allow inputs from power generating sources and various voltages enabling flexible power adaptation. For instance, the power management circuitry 239 may allow AC power to pass through so that the host piece of equipment is undisturbed. When the light fixture 100 is integrated into another electronic device, the power management circuitry 239 may allow the light fixture 100 to draw power from the power supply for the host electronic device as the power source 152. A single outlet can be used to avoid potential confusion when plugging in the device. The power management circuitry 239 may be operable to power from a variety of sources, including wireless, USB, DC, and battery sources. In one embodiment the power regulation is done in a buck boost manner to provide an energy harvesting power supply that produces a regulated power source when voltage is produced by various power sources.

The control system 200 in the illustrated embodiment may include regulator circuitry 246 configured to facilitate operation of the UV light regulator 120. The regulator circuitry 246 may include a motor controller and sensor circuitry. The motor controller and sensor circuitry may drive and monitor motor RPM of one or more fans. The motor controller may control the speed of the one or more fans, such as by adjusting a duty cycle of a PWM drive signal supplied to the one or more fans. The sensor circuitry may monitor current against a target and/or range of currents associated with a target RPM of the one or more fans.

The regulator circuitry 246 may also include UV light regulator sensor circuitry 256, which is shown separate from the regulator circuitry 246 in the illustrated embodiment but may be incorporated therein.

The motor controller of the regulator circuitry 246, as discussed herein, may be operable to control an amount of UV light directed into the room area 50 of the room. The motor controller may be a DC motor controller operable to supply power to drive a motor of the UV light regulator 120, which may move a movable component of the UV light regulator 120 to selectively increase or decrease an amount of UV light directed into the room area 50.

The UV light regulator sensor circuitry 256 may be operable to provide feedback indicative of at least one of a position of the movable component and an amount of UV light being directed into the room area 50. For instance, the UV light regulator sensor circuitry 256 may include a UV-C light sensor operable to provide a value indicative of an intensity of UV-C light being directed into the room area 50. The intensity value may aid in determining positioning of the movable component of the UV light regulator 120 to achieve a target level of UV light applied to the room area 50. The UV light regulator sensor circuitry 256, in one embodiment, may include an encoder (e.g., an optical encoder) indicative of a position of a motor shaft or the movable component, thereby being indicative of an amount of UV light being applied to the room area 50.

In one embodiment, as discussed herein, the control system 200 may include a room sensor interface 255 operably coupled to the controller 236. The room sensor interlace 255 may be configured to provide feedback indicative of whether the room area 50 (potentially the entire area of the room) is occupied by one or more persons. The room sensor interlace 255 may be configured to count people or track the number of people within the room area 50. Alternatively, feedback from the room sensor interlace 255 may be used by a controller separate from the room sensor interlace 255 to count people or track the number of people within the room 50.

In the illustrated embodiment, the control system 200 may use feedback from the room sensor interface 255 to determine whether to direct UV light into the room area 50, or to discontinue providing UV light into the room area 50.

It is to be understood that the room sensor interface 255 may be separate from the control system 200 in an external device capable of communicating information indicative of presence of one or more persons in the room. For instance, the room sensor interface 255 may be a motion sensor (e.g., a PIR sensor) capable of sensing the presence of one or more persons in the room or room area 50. This motion sensor may communicate wirelessly with the control system 200 or with an intermediary device capable of relaying occupancy information to the control system 200. Additionally, or alternatively, the room sensor interface 255 may include a switch coupled to a door of the room to indicate a status of the room as being open or closed, using this information as an indicator of whether the UV light source can be activated for disinfection of the room area 50. For instance, if the door is determined to be open, activation of the UV light source 160 may be prevented in order to avoid leakage of UV light outside the room area 50.

The control system 200 may include a visible light driver 245 separate from or provided in the visible light module 180 to facilitate directing operation of a visible light source. The visible light driver 245 in the illustrated embodiment may also include a user interface (e.g., an ON/OFF switch, a brightness adjuster, and a color adjuster) operable to allow a user to control operation of the visible light source. For instance, the user may utilize the user interface to direct the visible light driver 245 to increase or decrease a color temperature of the visible light source. The visible light driver 245 may include a controlled current source and/or a controlled voltage source to supply power to the visible light source in accordance with a target operative mode of the visible light source.

III. UV Light Regulator

Figure 3A:
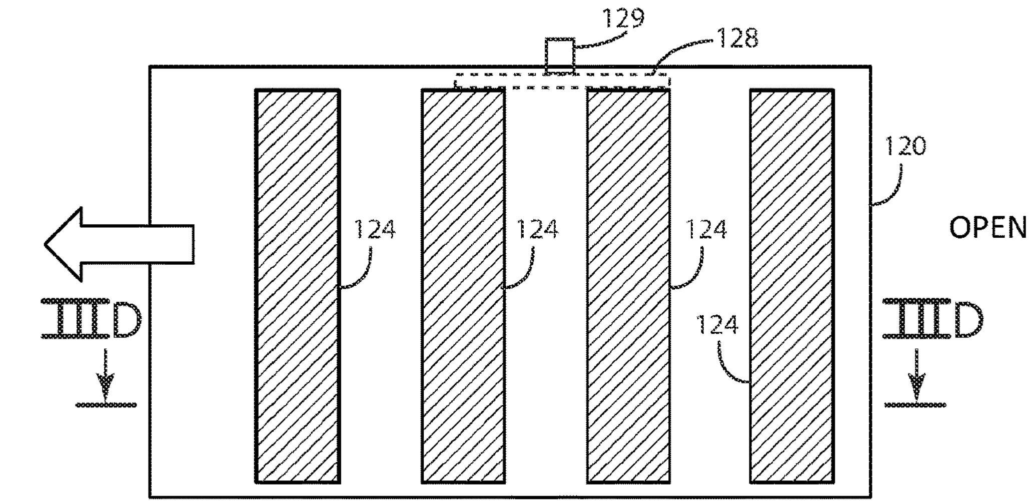
FIGS. 3A-D show a UV light regulator in accordance with one embodiment.
Figure 3B:
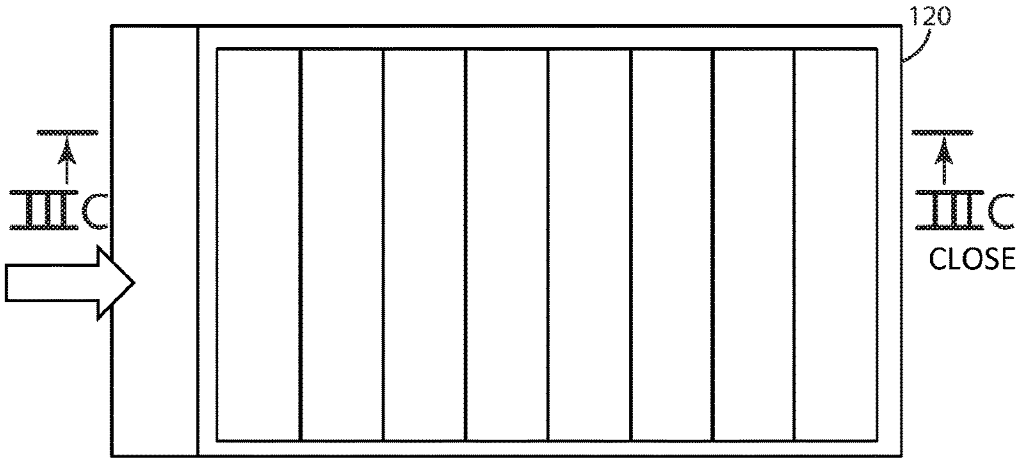

The UV light regulator 120 in accordance with one embodiment is shown in FIGS. 3A-B in a closed position and an open position. The UV light regulator 120 may be operable to selectively control an amount of UV light directed into the room from a germicidal light source, such as the UV light source 160. The UV light regulator 120 may include one or more apertures 124 selectively transmissive with respect to UV light. Each of the one or more apertures 124 may be a window operable that is transmissive to UV light and adjustable in size. The window may allow gas or air to pass through or may include a UV transmissive material (e.g., glass) that allows passage of UV light but not gas or air.

In the illustrated embodiment, the UV light regulator 120 includes a stationary element 121 having a plurality of stationary windows 125 that are UV light transmissive and optionally air transmissive. The UV light regulator 120 may also include a movable element 123 having a plurality of movable windows 127 that are UV light transmissive and optionally air transmissive. Each of the stationary windows 125 may be associated with one of the movable windows 127, together forming an aperture 124 with a variable size window.

Figure 3C:
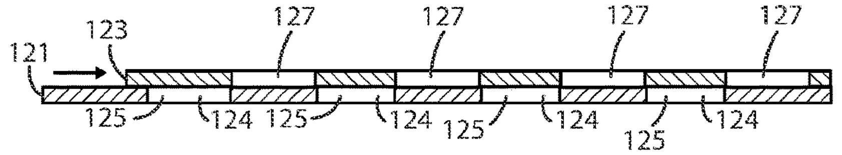
Figure 3D:
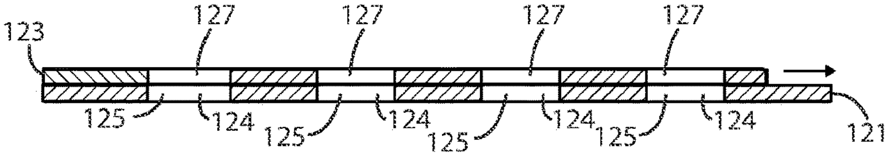

The movable element 123 in one embodiment may slide laterally relative to the stationary element 121 such that the overlap may be varied between each stationary window 125 and associated movable window 127. The degree or amount of overlap may set the size of the aperture 124 (e.g., between fully closed as shown in FIG. 3C and fully open as shown in FIG. 3D).

A motor may be coupled to a pinion gear 129 in the illustrated embodiment that interlaces with a rack gear 128 of the movable element 123 to facilitate lateral movement of the movable element 123. It is to be understood that the present disclosure is not limited to the pinion and rack gear configuration for moving the movable element 123; any type of mechanism may be provided to facilitate movement of the movable element 123.

Figure 8:
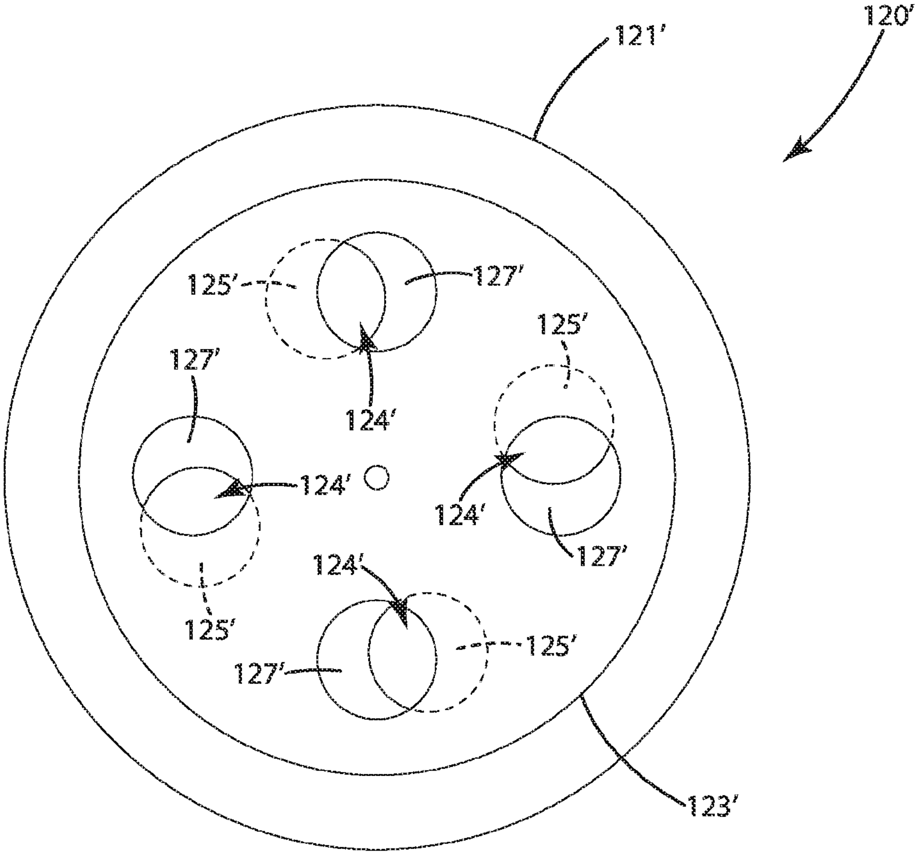
FIG. 8 shows a UV light regulator in accordance with one embodiment.
Figure 9:
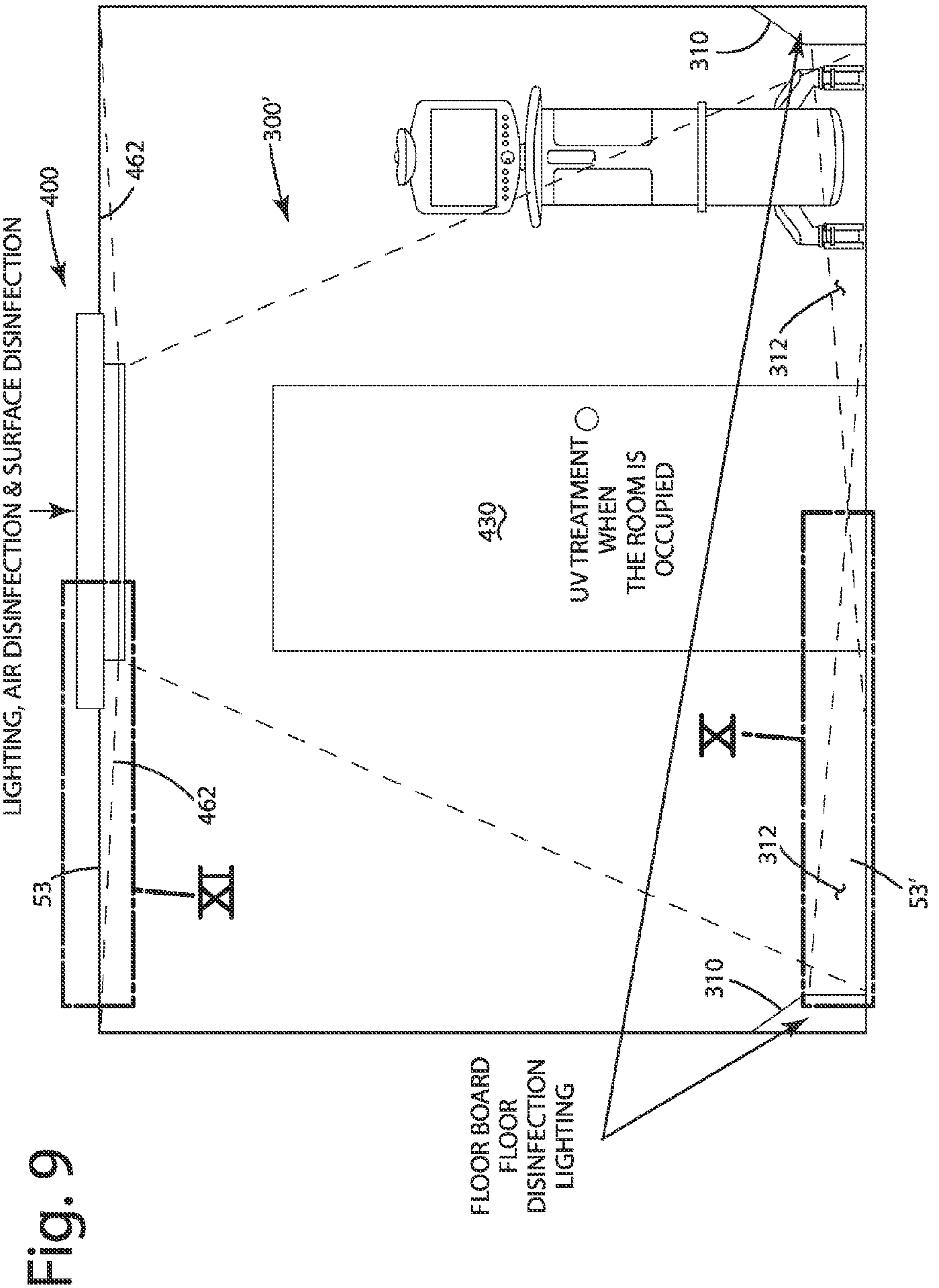
FIG. 9 shows a disinfection system in accordance with one embodiment.

An alternative embodiment of the UV light regulator 120 is shown in FIG. 8 and includes similarly configured components designated with the same reference numbers followed by "'". The UV light regulator 120' includes a stationary element 121' and a movable element 123' in the form of a rotatable disk having a plurality of movable windows 127' that move relative to stationary windows 125' such that an overlap between the movable windows 127' and the stationary windows 125' defines the aperture 124' having a variable size, thereby allowing control over the amount of UV light directed through the UV light regulator 120. The center of the movable element 123' may be coupled to a motor to facilitate rotation of the movable element 123' in response to rotation of the shaft of the motor. The UV light regulator 120' in the illustrated embodiment may rotate continuously without stopping to control an amount of UV light directed through the UV light regulator 120 into the room area 50.

As discussed herein, the light fixture 100 may include UV light sensor circuitry 256. In one embodiment, the UV light sensor circuitry 256 may include a UV sensor that is responsive to UV-C light and capable of providing sensor output indicative of an intensity of UV-C light received by the UV sensor. The UV sensor of the UV light sensor circuitry 256 may be disposed at a downstream position relative to the UV light regulator 120 such that if the UV light regulator 120 is closed, the UV sensor senses substantially no UV-C light from the UV light source 160.

The UV light sensor circuitry 256 may include more than one UV sensor in one embodiment. For instance, a first UV sensor may be disposed downstream of the UV light regulator 120, and a second UV sensor may be disposed upstream of the UV light regulator 120. This way, a measurement of UV light intensity may be obtained from the UV light source 160 without being regulated. In other words, the UV light sensor circuitry 256 may indicate a full amount of light available for regulation by the UV light regulator 120, knowing this full amount may be helpful in diagnostics and in controlling at least one of the UV light source 160 and the UV light regulator 120. For instance, the control system 200 may increase or decrease UV light output from the UV light source 160 based on output from the second UV sensor upstream of the UV light regulator 120.

The control system 200 in one embodiment may compare sensor output from the first and second UV sensors to determine control parameters for the UV light regulator 120. For instance, the control system 200 may adjust at least one of operational parameter of the UV light source 160 (e.g., to increase or decrease output intensity) and an amount of light directed by the UV light regulator 120 from the UV light source 160 to the room 50. The room can be, for example, a room of a house, a car cabin, an elevator, a train compartment, a bathroom, or any other enclosed space.

In one embodiment, the UV light sensor circuitry 256 may include more than one UV sensor disposed at stages of the UV light regulator 120. As discussed herein, the UV light regulator 120 may include more than one stage of UV light control. For instance, the UV light regulator 120 may include a first UV light regulator, such as construction shown in the illustrated embodiment of FIGS. 3A-3D, and a second UV light regulator capable of directing the UV light received from the first light regulator and controlling an amount of the received UV light that is transmitted downstream of the second UV light regulator. For instance, the second UV light regulator may be similar to the construction shown in the illustrated embodiment of FIG. 8, or any type of UV regulator described herein or structure capable of controlling an amount of UV light directed downstream of the structure. UV sensors of the UV light sensor circuitry 256 may be disposed after each stage of the UV light regulator, including downstream of the first UV light regulator and downstream of the second UV light regulator.

Figure 6:
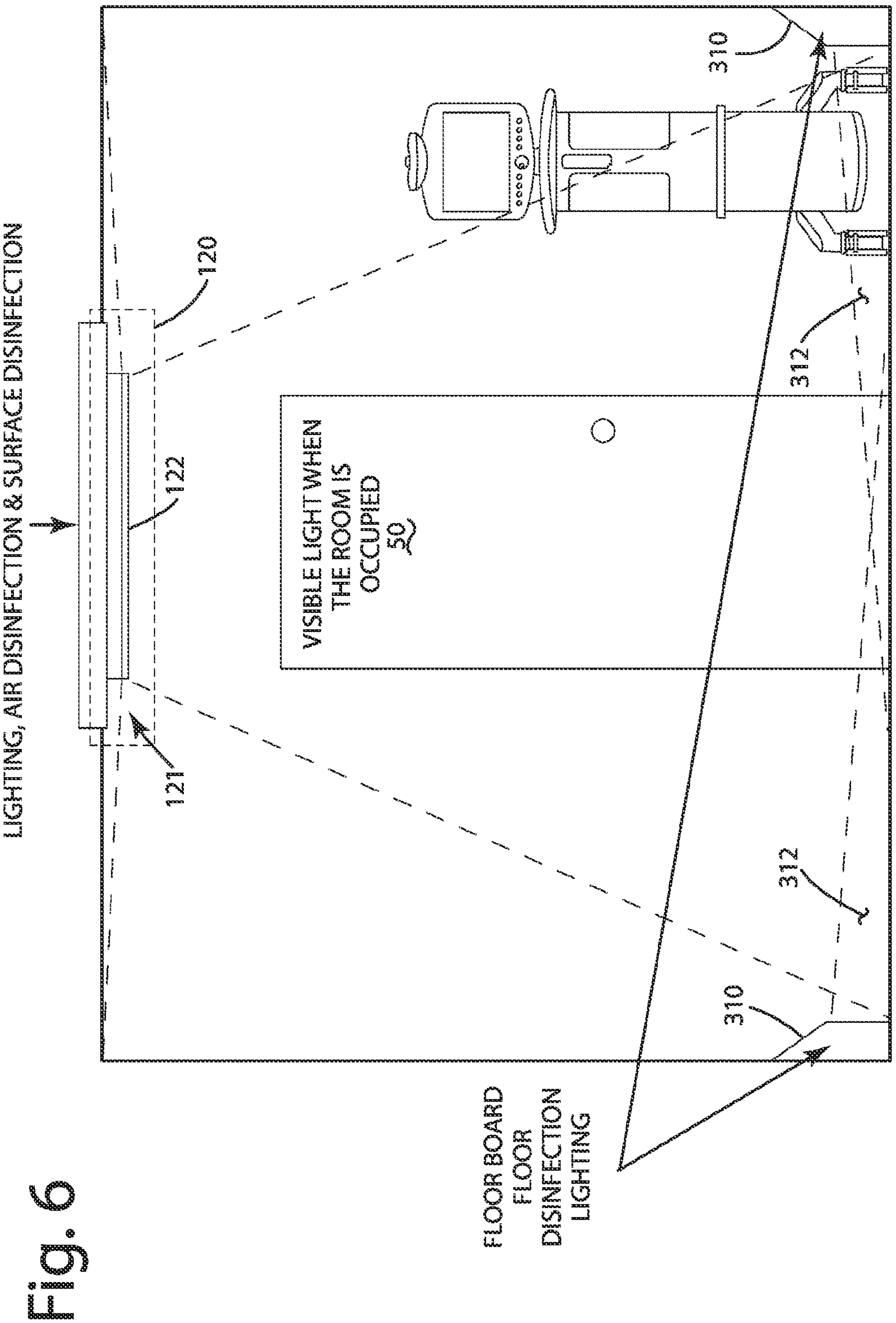
FIG. 6 shows a disinfection system with a plurality of light fixtures in accordance with one embodiment of the present disclosure.
Figure 7:
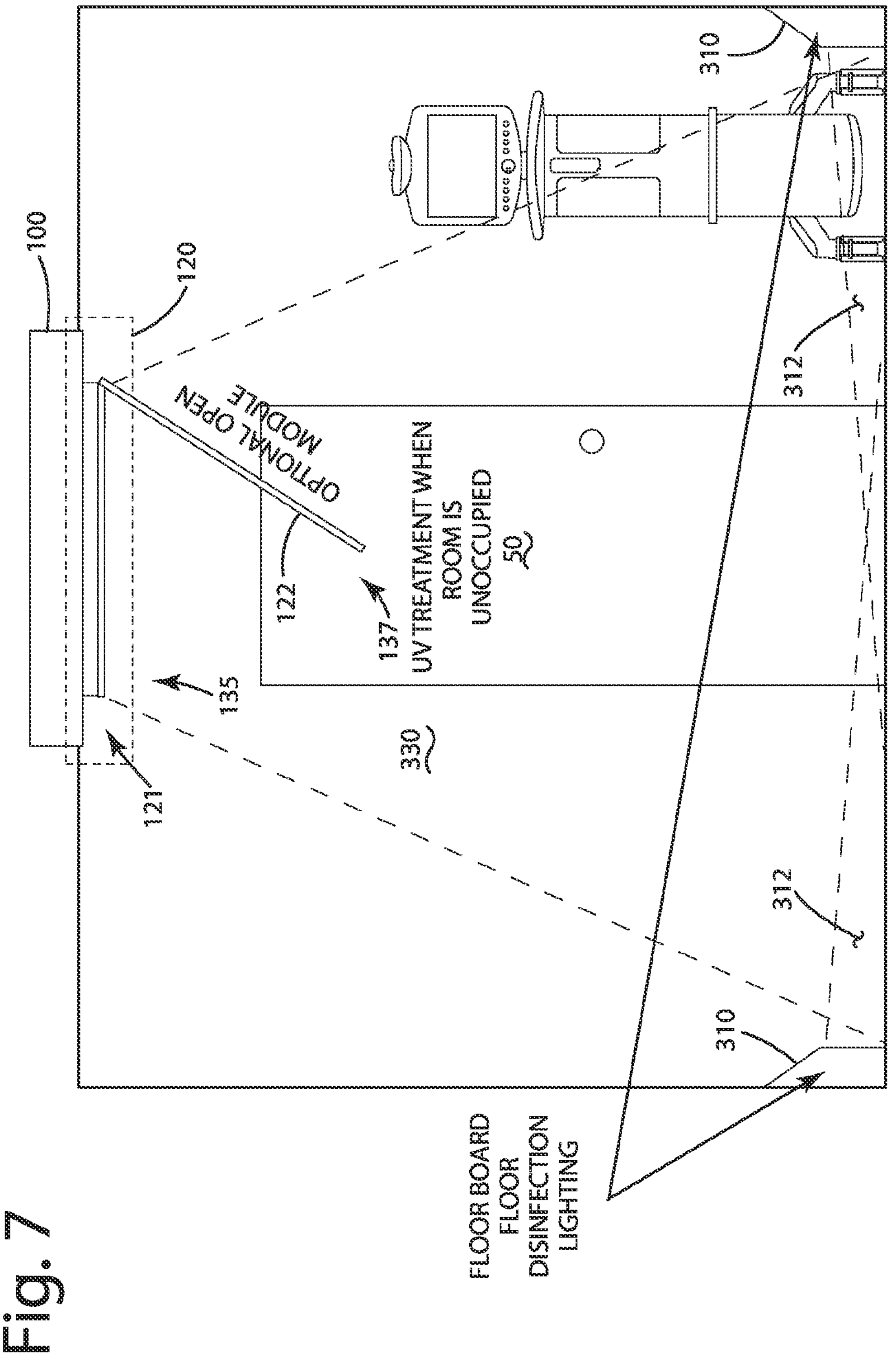
FIG. 7 shows the disinfection system of FIG. 6 with a light fixture supplying UV light to a room area in accordance with one embodiment.

Alternatively, or additionally, the UV light regulator 120 may include a door 122 capable of being pivoted from a closed position 135 to an open position 137. This construction in accordance with one embodiment is shown in FIGS. 6 and 7. In the closed position 135, the door 122 may substantially prevent UV light from the light fixture 100 from being directed into the room area 50. And, in the open position 137, the door 122 may direct UV light from the light fixture 100 into the room area 50. The door 122 in one embodiment may be provided in place of or in addition to the stationary element 121 and movable element 123. For instance, the stationary element 121 and movable element 123 described in connection with the illustrated embodiment of FIGS. 3A-D may be a first UV light regulator, and the door 122 may be a second UV light regulator downstream of the first UV light regulator.

In the illustrated embodiment of FIGS. 6 and 7, and as discussed herein, the UV light regulator 120 may be operable to control transmission of the UV light from the UV light source 160 to block the UV light from being directed into the room area 50 based on a room occupied status in the control system 200 being indicative that the room area 50 is occupied. The UV light regulator 120 may be operable to direct a controlled amount of UV light from the UV light source 160 into the room area 50 based on the room occupied status and the control system 200 being indicative that the room area 50 is unoccupied.

As discussed herein, the light fixture 100 may include a visible light module 180 operable to supply visible light to the room area 50. The visible light module 180 may be operable by the control system 200 to supply visible light based on a visible light directive (e.g., an input from a light switch associated with the room area or based on the room occupied status being indicative that the room is occupied). Additionally, or alternatively, the visible light module 180 may be operable to supply visible light to the room area 50 based on whether the UV light regulator 120 is supplying UV light from the UV light source 160 to the room area 50.

IV. Disinfection System

Figure 4:
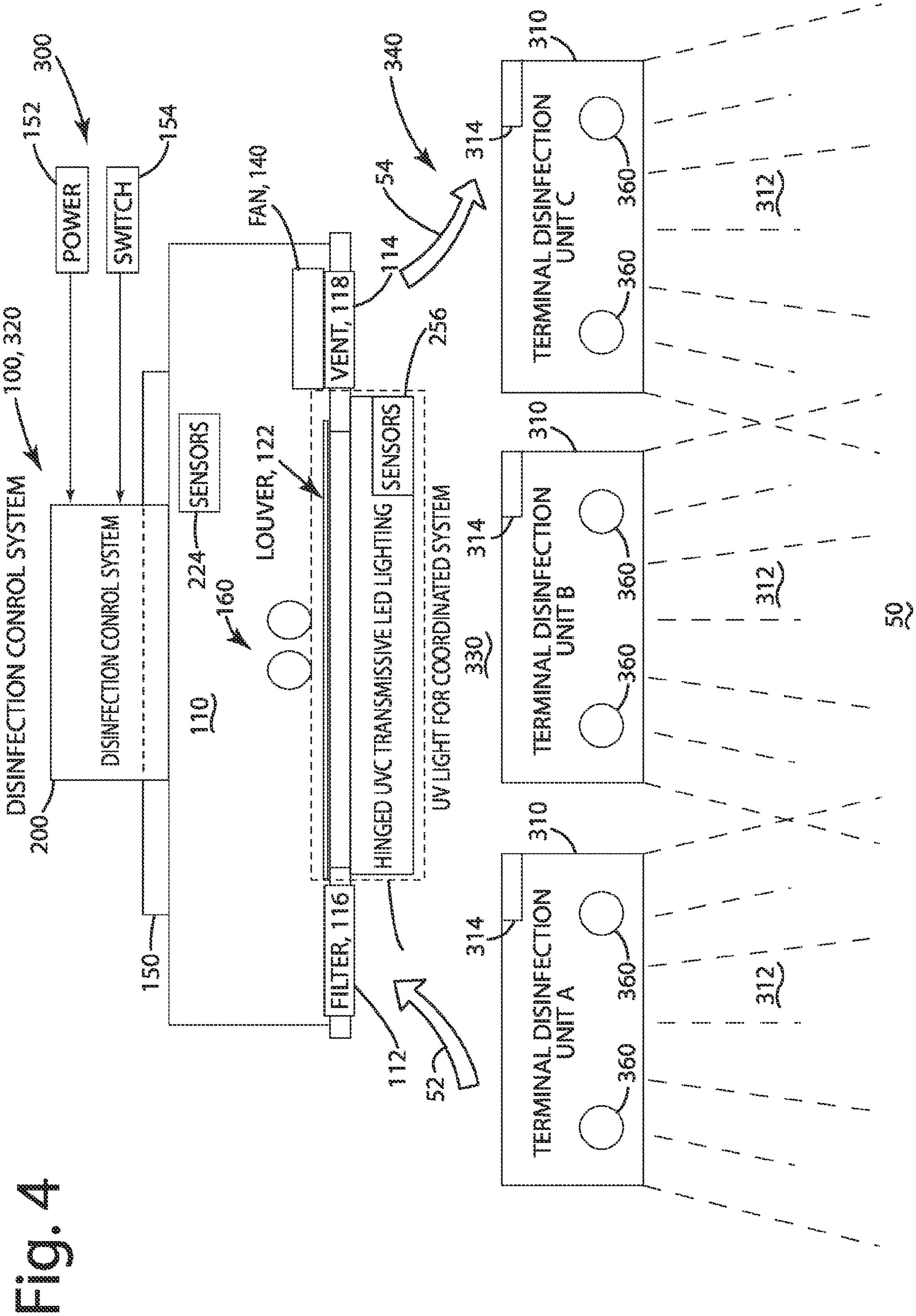
FIG. 4 shows a disinfection system in accordance with one embodiment of the present disclosure.

A disinfection system according to one embodiment is shown in FIG. 4 and generally designated 300. The disinfection system 300 may include a light fixture 100 in accordance with one embodiment described herein and multiple remote disinfection units 310. The light fixture 100 may be a primary unit 320 of the disinfection system 300; however, the present disclosure is not so limited. For instance, the light fixture 100 may be a remote disinfection unit 310 in one embodiment.

The disinfection system 300 may include the light fixture 100 with additional networked disinfection systems that treat other areas of the room and share treatment sequences and data. The light of the room may be modulated to contain the ID of the light fixture 100, which may communicate encrypted information. The other devices in the network, such as keyboards, input devices, surface treatment devices, and floor treatment devices may operate in conjunction with the light fixture 100 to decontaminate the room area 50. This disinfection system 300 may be operable to detect environmental service workers when cleaning and to detect assets, people, and other devices in the room area 50. The ID may allow devices to associate with a device for control, and enable control sequences and protocols for obtaining analytics, and in-room tracking of disinfection within the network and within the local room.

In the illustrated embodiment, the primary unit 320 is operable to control and monitor several remote disinfection units 310. In this embodiment, the disinfection control system 300 includes a primary unit 320 that includes UV light source and control circuitry capable of controlling operation of UV light source in the primary unit 320, as well as the remote disinfection units 310. The primary unit 320 in the illustrated embodiment is the light fixture 100, including a control system 200, a UV light source 160, a UV light regulator 120, a power source 152, a switch 154, an air inlet 112, and an air outlet 114. The light fixture 100 may be configured differently in accordance with one or more embodiments described herein. For instance, the light fixture 100 may include a door 122 operable as the UV light regulator 120 instead of or in addition to the moveable and stationary elements 121, 123.

In the disinfection system 300 in the illustrated embodiment, the remote disinfection units 310 controlled by the primary unit 320 via a communication system 340. The communication system 340 may be a wired or wireless network system, or a combination thereof. For instance, the communication system 340 may include a wired Ethernet communication system and/or a Wi-Fi communication network.

As another example, the communication system 340 may be based on modulated light, including modulated UV light 330 as depicted in the illustrated embodiment. The modulated UV light 330 may include encoded data capable of being extracted and processed by one or more of the remote disinfection units 310. The remote disinfection units 310 may include a UV light sensor capable of detecting the modulated UV light 330 and communication circuitry capable of decoding data from the modulated UV light 330.

In one embodiment, the remote disinfection units 310 may be operable to sense presence or absence of UV light from the primary unit 320. With this configuration, the modulated UV light 330 may be replaced with unmodulated UV light from the primary unit 320. The remote disinfection units 310 may be operable to sense such unmodulated UV light and may be operable, in response to sensing presence of the unmodulated UV light, to generate UV light for disinfection purposes.

In one embodiment, the remote disinfection units 310 are configured in one embodiment to direct UV light 312 into a room area. The remote disinfection units 310 may be in the same or different rooms, and may direct UV light to overlapping areas of a room, or any combination thereof. The remote disinfection units 310 may include one or more UV light sources 360 capable of generating UV light and configured similar to the UV light source 160 described herein in conjunction with the light fixture 100. The remote disinfection units 310 may also include a control system 314 capable of directing operation of the remote disinfection unit 310, such as controlling UV light output from the UV light sources 360. In one embodiment, one or more or all of the remote disinfection units 310 may be a light fixture 100 as described herein. For instance, the remote disinfection units 310 may be capable of treating air via UV light in an air treatment chamber 110. One or more aspects of the light fixture 100 that are described herein may be absent from the remote disinfection units 310. For instance, the remote disinfection unit 310 may not include an air treatment chamber 110, or a UV light regulator 120. As another example, the remote disinfection unit 310 may not include a visible light module 180.

In one embodiment, the remote disinfection units 310 may be powered separately via separate connections to a shared power supply (e.g., building utility power). Additionally or alternatively, one or more of the remote disinfection units 310 may each receive power from separate power sources, such as a battery.

In one embodiment, the remote disinfection units 310 may be powered via a bus or multiple power supply wires provided in a cable harness. Optionally, the cable harness may include communication and/or control wires that form part of the communication system 340.

The remote disinfection units 310 in conjunction with the primary unit 320 may be operable to supply UV light, in one embodiment, to a room area 50 from different angles. This way, complex surfaces provided in the room area 50, such as surfaces provided by furniture, may receive UV light for disinfection purposes. Activation or operation of the UV light sources 160, 360 of the remote disinfection units 310 and the primary unit 320 may facilitate coordinated disinfection of a room area 50. By using multiple heads with one control (e.g., the primary unit 320), costs can be kept down and larger and more complicated surfaces can be disinfected. For example, different UV sources can be directed toward different regions of a complex surface to help ensure that the entire surface is properly disinfected.

It is noted that the remote disinfection units 310 may be disposed in a variety of locations of the room. For instance, the remote disinfection units 310 may be provided as fixtures in the room. Additionally, or alternatively, the remote disinfection units 310 may be provided on one or more objects in the room, such as a vitals monitor, an IV pump, a visible light lamp, or a keyboard. These objects may include remote disinfection units 310 capable of being activated in response to a directive provided by the primary unit 320 via the communication system 340. For instance, in the illustrated embodiment, the primary unit 320 may transmit an encoded signal via the modulated UV light 330 to the remote disinfection units 310 to activate or operate the UV light source 360 to generate UV light 312 for disinfection of the room area 50 or another surface provided in the room (e.g., the inside surface or a concealed surface of a keyboard).

In one embodiment, multiple UV light sources (e.g., a primary unit 320 and one or more remote disinfection units 310) may be used in coordination to clean hard to reach areas. The whole room terminal cleaning systems can use sweeping high intensity UV light to clean a room. The amount of time determined for providing a target dose can be reduced relative to conventional single light source systems. Additionally, or alternatively, the system may utilize UV disinfection for specific areas or devices, such as multiple high touch areas, in conjunction with each other and/or one or more light fixtures 100. Air disinfection may also be provided to achieve even better disinfection impact. In one embodiment, assets may be identified with a room, enabling a determination as to when terminal cleaning is being used, logging cleaning activity via a network for disinfection times for the units being used, and coordinated cleaning with any other devices in the room for a deep cleaning cycle.

In one embodiment, one or more remote disinfection units 310 may be disposed for directing UV light 312 toward a floor of the room in a manner parallel to or converging with the floor of the room. For instance, the remote disinfection unit 310 may be a floorboard disinfection fixture capable of directing light from a wall adjacent to the floor and toward the floor or parallel to the floor. This configuration can be seen in the illustrated embodiment of FIGS. 6 and 7.

In one embodiment, the remote disinfection units 310 may be operable to communicate information to the primary unit 320 and/or another external device via the communication system 340. The information communicated by the remote disinfection units 310 may include status information, such as whether UV light 312 is being supplied from the UV light source 360, the duration and/or intensity of the UV light 312, and the time associated with supply of the UV light 312. This information may enable tracking disinfection status for one or more areas or objects of the room.

For instance, an object may not be permanently disposed in the room, and may be movable to another room. The object may or may not include a remote disinfection unit 310. In one embodiment, the object may include tracking circuitry capable of facilitating the identification of whether the object is within the room, time of entry, and time of exit. This information may enable tracking disinfection dosage for the object (e.g., duration and time of dosage and intensity of dosage). This way, the disinfection system 300 may determine whether the object has been disinfected and is therefore cleared for movement from one room to another. If the object is determined to be insufficiently disinfected, the disinfection system 300 may indicate that the object should not be moved, and potentially, disinfection may be prioritized for the room in which the object is disposed in order to allow movement of the object in response to a request to do so. In one embodiment, if the object is moved, disinfection may be prioritized in the new room to which the object has been moved. The tracking circuitry may include a Bluetooth Low Energy (BTLE) transceiver, capable of communicating with BTLE circuitry disposed in the room, potentially within the primary unit 320.

The object and/or the remote disinfection units 310 may include one or more sensors capable of detecting contact with, or touches from, users or other objects in the room. This information may be communicated to the disinfection system 300 to be used as a basis for determining when and how long to conduct a disinfection process. As an example, if a keyboard indicates a user has touched it within the last hour, and the disinfection system 300 determines no person is occupied in the room, a UV light source 360 of the keyboard and/or one or more other UV light sources 160, 360 in the room may be activated for a disinfection process. Contact between objects may also be identified, such as contact between one or more medical instruments in a room and a surgical tray, and used as a basis for determining whether to schedule a disinfection process for one or both of the objects or the room in which the objects are disposed. In one example, contact between two or more objects may be indicative of an action that occurred in the room (e.g., a surgery) and a disinfection process may be scheduled based on identification of the action as having occurred.

In one embodiment, the system 300 may monitor room activity via sensor feedback or communications from one or more devices. For instance, when the HVAC kicks in, flow changes may occur. These changes may kick up dust and other contaminants. The system 300 may increase air treatment in response to the HVAC turning on to enhance disinfection with respect to the dust and other contaminants. The system 300 may sense air flow, motion, and in room activity to respond to potential contaminants within the room.

In one embodiment, the control system 200 of the light fixture 100 may include driver circuitry for the UV light source 160 or the visible light module 180, or both, under control of the controller 236. The driver circuitry may be a lamp driver driven by a PWM output of the controller 236. The UV light or the visible light, or both, may provide data signaling by producing pulses or gaps in the light that can be sensed by devices within proximity to the light fixture 100. This communication technique can be utilized by the UVC lighting or general visible lighting. Signaling via the UVC light may be utilized to control or coordinate other disinfecting devices (e.g., a remote disinfection unit 310).

The use of driver circuitry or digital ballasts controlled by the controller 236 may allow controlled source intensities to be defined and utilized by a PWM control method. The time for treatment between movement in the room may be tracked. An accumulator may be utilized to track the average time between movement. The treatment in the room among various sensor outputs may provide a profile of movement for each of the various sensors and systems. The room cleaning may be coordinated as triggering the floor, for example, and may allow the ceiling treatment to begin. In one embodiment, the air treatment system of the light fixture 100 may always be running to help the disinfection process by increasing intensity of the reactor and fan speed while disinfecting in deep cycles. When the system 300 detects environmental services (cleaning) or higher movement in the room (e.g., a high needs patient), air flow for air treatment can be increased and reactor intensity can be increased.

In one embodiment, a device ID may be associated with the light fixture 100 as the primary unit 320. This device ID may enable the device to synchronize with the pulses or patterns encoded in the light (e.g., UV light and/or visible light). The association between the device ID and the light fixture 100 can be flagged over a network based communication system (e.g., a cloud messaging system) with which the light fixture 100 and the remote disinfection units 310 may communicate. The remote disinfection units 310 that sense the light pattern from the light fixture 100 may be associated with the light fixture 100 and its device ID. The generation of a specific detectable pattern may be microprocessor controlled and programmable to be enabled by motion, BTLE beacons, WiFi links, remote network sensors, or messages, or a combination thereof.

Figure 12:
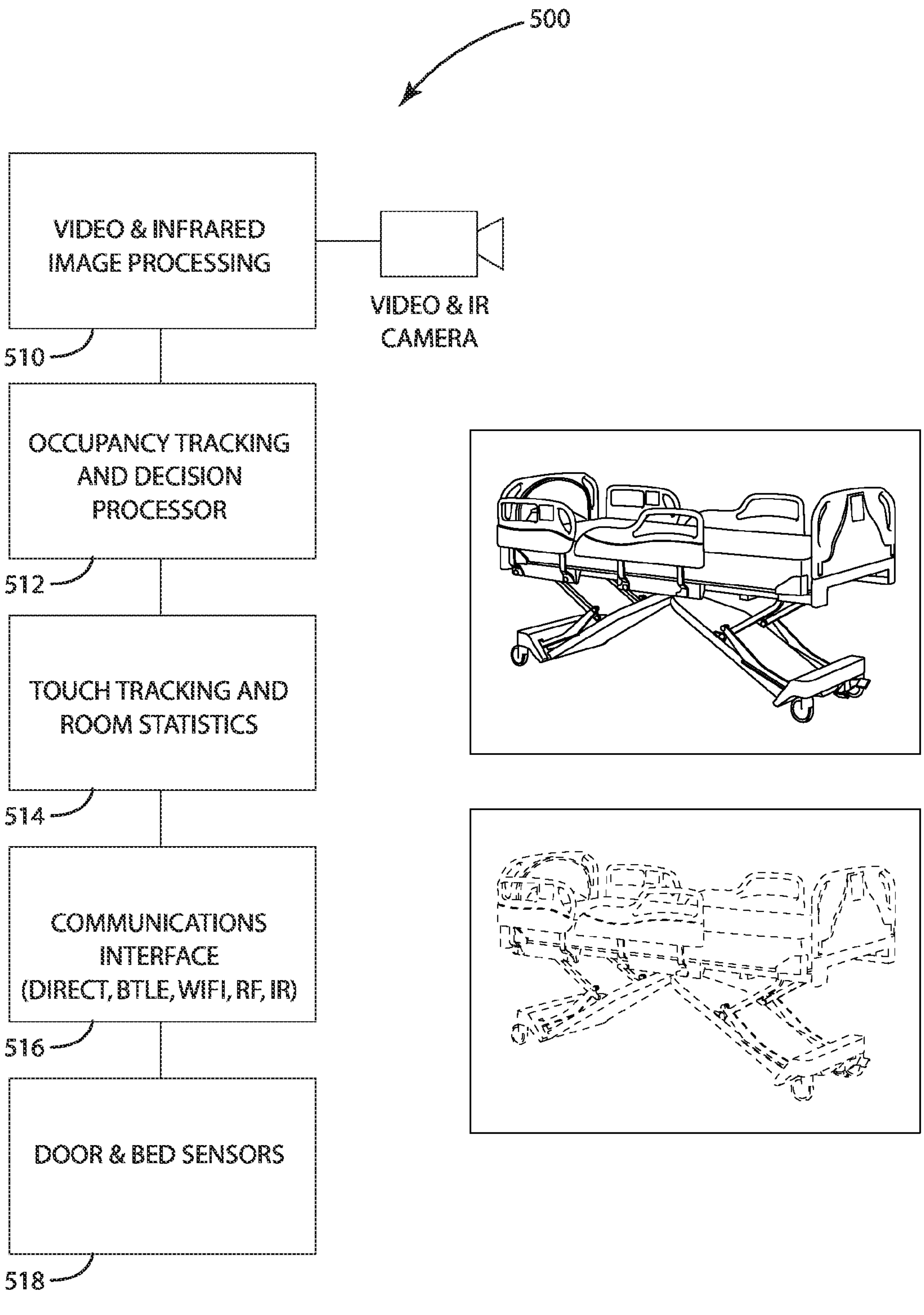
FIG. 12 shows a disinfection system in accordance with one embodiment.

In the illustrated embodiment of FIG. 12, a disinfection system in accordance with one embodiment is provided and generally designated 500. The disinfection system 500 may include video and image processing circuitry 510 operably coupled to occupancy tracking and decision processing circuitry 512. Tracking and room statistic circuitry 514 may provide information to the occupancy tracking and decision processing circuitry 512. A communications interlace 516, such as Ethernet, direct wired control communication BTLE, Wi-Fi, RF, or IR, or a combination thereof, may be operably coupled to one or more sensors 518 (e.g., door or bed sensors) and provide information to the occupancy tracking and decision processing circuitry 512. The communication interlace 516 may couple the disinfection system 500 directly to a room control system or remotely to a separate system, which may be configured to monitor and control a room.

The video imagery of the disinfection system 500 may utilize optics and infrared for tracking body counting, movement and occupancy sensing. The optical processor may identify any body sized image and is calibrated for anything from a baby to an adult as well as body temperatures. The system may also have audio sensors and processor for recognizing events and logging these for statistical analysis as well as occupancy. Bodies are counted for statistical event counting as well as the patient. These images are differentiated by profile and tracking to the bed/bathroom etc.

V. UV Reflector

In one embodiment of the present disclosure, a light fixture is provided for directing light toward a surface of a room. Such a light fixture in accordance with one embodiment is shown in FIGS. 5 and 9-11 and generally designated 400. The light fixture 400 may be incorporated into a disinfection system 300' similar to the disinfection system 300 described herein with the exception that the light fixture 400 may be provided in addition to or in place of the light fixture 100.

It is noted that that the disinfection system 300 includes a communication system 340 that, in one embodiment, utilizes UV light, optionally modulated UV light 330, to communicate with remote disinfection units 310. The communication system 340 may alternatively or additionally communicate with the remote disinfection units 310 using visible light 430 as depicted in the illustrated embodiment of FIG. 5. Communication may be provided via visible light by presence or absence of the visible light 430, or by modulating the visible light 430.

The light fixture 400 in accordance with one embodiment may be similar to the light fixture 100 with several exceptions, including a reflector 464 operable to direct UV light 462 within a light region 469.

Similar to the light fixture 100, the light fixture 400 may include an air inlet 412, an treatment chamber 410, and an air outlet 414, similar respectively to the air inlet 112, the treatment chamber 110, and the air outlet 114. A fan 440, similar to the fan assembly 140, may direct air 492 through the air inlet 412 and through a filter 416 disposed near the air inlet 412. The air may be further directed through the air treatment chamber 410 and treated with UV light from a UV light source 460, which may be similar to the UV light source 160. The fan 440 may facilitate discharge of air 494 through the air outlet 414 via a vent 418 after the air has been treated in the treatment chamber 410. The light fixture 400 may include a support member 450 similar to the support member 150 for supporting the light fixture 400 in the room area 50. The fan may be monitored for current and/or load, and may be controlled by PWM. Based on one or more operating conditions (e.g., the duty cycle of the PWM, the monitored current, or monitored load, or a combination thereof), a change in pressure drop may be determined. Additionally, or alternatively, based on one or more operating conditions, an end of life (EOF) indication may be determined. The system may include multiple fans, enabling a comparison of data between fans to determine if one or more operation conditions are indicative of a fluid problem or a fan issue.

In the illustrated embodiment, the light fixture 400 includes a visible light module 480, which may be similar to the visible light module 180 of the light fixture 100. Likewise, the light fixture 400 may include a control system 490, a power source 452, and a switch 454, similar respectively to the control system 200, the power source 152, and the switch 154.

The reflector 464 in the illustrated embodiment may be operable to direct light from the UV light source 460 to one or more light outlets 471, 472. The light outlets 471, 472 and/or the reflector 464 may be configured to direct the light within a light region 469 and toward a target surface 53, such as the ceiling or floor 55 in the illustrated embodiments of FIGS. 9-11. The light region 469, as described herein, may be defined by a boundary line 461 parallel to the target surface 53 (e.g., parallel to the ceiling) or that converges with the target surface 53. For instance, in the illustrated embodiment of FIG. 11, the boundary line 461 is shown parallel to the target surface 53 such that a distance D, 467 between the boundary line 461 and the target surface 53 is substantially constant.

For purposes of disclosure, the boundary line 461 is shown to have an angle different from the UV light 462 directed toward the reflector 464 to the target surface 53 because the distance D, 467 is provided at a distance such that the light region 469 is outside of a region of space that a head of a person can occupy while standing in the room. For instance, the distance D, 467 may be less than 6 inches with an 8 foot ceiling so that a person standing in the room is unlikely to be able to place their head or eyes directly within the light region 469.

As mentioned, for purposes of disclosure, the boundary line 461 is shown to have an angle different from the UV light 462 in the illustrated embodiment. The boundary line 461 in the illustrated embodiment may be at an angle α, 466 relative to the target surface 53 such that it converges with the target surface 53 from an intersection point provided proximate to the light opening 471. This way, the light region 469 is within distance D, 467 or less of the target surface 53. The reflector 464 may be provided at an angle β, 468 to direct the UV light 462 within the light region 469 defined by the boundary line 461 and the target surface 53.

In one embodiment, UV light 465 may be directed from the UV light source 460 toward the reflector 464 and reflected toward the target surface 53 but within the light region 469. The UV light 465 may be directed through an outlet or opening 472 of the light fixture 400, which may be permanently transmissive with respect to the UV light 465 but non-transmissive with respect to air. Alternatively, a UV light regulator in accordance with one embodiment may control transmission of UV light 465 to the reflector 464. Additionally, or alternatively, one or both of the air inlet 412 and the air outlet 414 may be utilized to direct UV light 465 from the UV light source 460 to the reflector 464.

In one embodiment, the reflectors and/or baffles of the light fixture 400 may be configured to transmit light in a plane parallel with the target surface 53 or that converges with the target surface 53. The light fixture 400 may have a reflector 464 that reflects light from the UV light source 460 within the light region 469, taking the radian points from the lamp surface of the UV light source 460 and reflecting them along the parallel plane from closest to the UV light source 460 to farther away from the UV light source 460. The actual pitch may concentrate the light to the farther reach by virtue of the inverse square law to achieve a target intensity and define a dosage possible at a target distance. The reflector 464 may distribute the light rays by that proportion. Optionally, a chamber reflector 467 may be provided if the reflector 464 uses the output from a second portion of the UV light source 460 to again selectively redistribute that portion energy over the distance by reflecting from the chamber reflector 467 to the reflector 464 and over the plane as provided in an attempt to homogenize the energy as it relates to the inverse square law.

Figure 10:
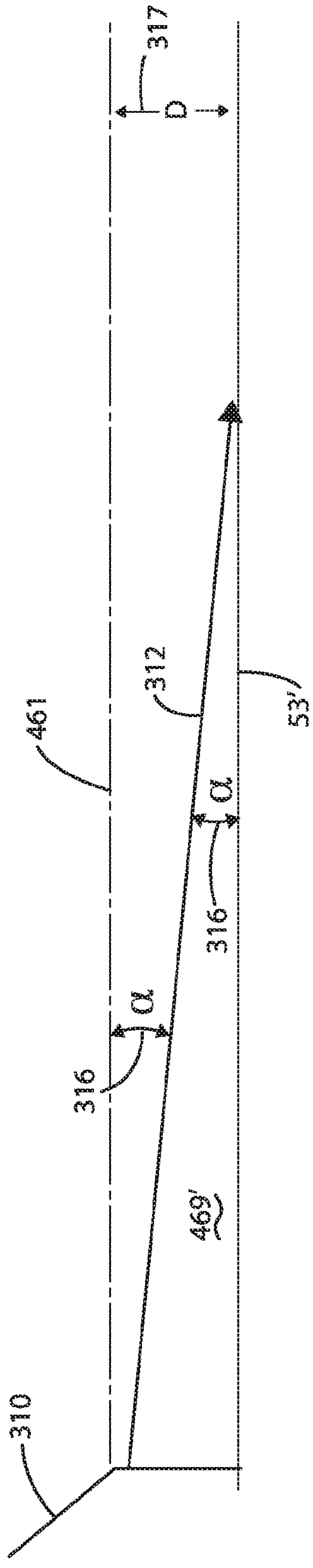
FIG. 10 shows an expanded view of a portion of FIG. 9.
Figure 11:
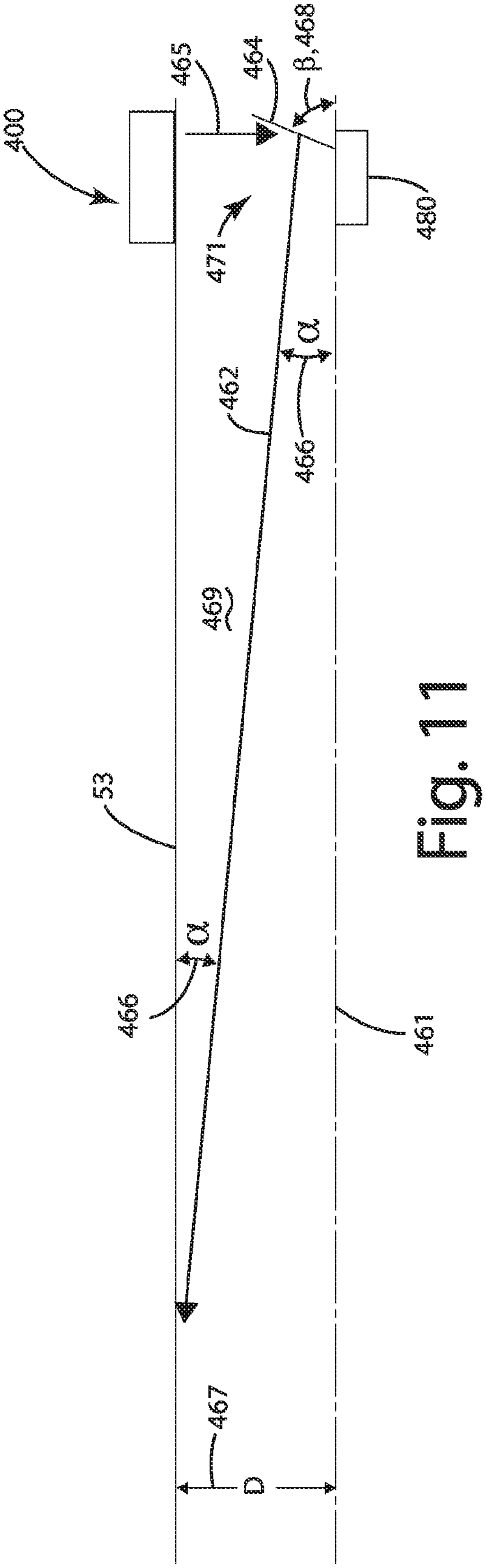
FIG. 11 shows another expanded view of a portion of FIG. 9.

It is noted that the light region 469 may be defined in conjunction with other light sources described herein, including the remote disinfection units 310 as depicted in the illustrated embodiment of FIG. 10. The remote disinfection unit 310 may be configured such that its UV light output is directed within a light region 469' defined by a boundary line 461' that is parallel to or converges with the target surface 53', which is the floor in the illustrated embodiment. The boundary line 461' may be at an angle α, 316 relative to the target surface 53' such that UV light 312 from the remote disinfection unit 310 is confined to the light region 469' and is at distance D, 317 or less with respect to the target surface 53'. This way, it is unlikely that a person occupying the room would position their head and eyes within the light region 469'.

In one embodiment, the parallel plane surface treatment used on the ceiling may be used for disinfecting the floor. By restricting the parallel plane to a specific distance from the target surface 53', an inherent level of human protection can be provided while providing disinfection to hard to reach surfaces. In the illustrated embodiment, a person's eyes would not be exposed to the UV light source unless they put their head on the floor and looked directly into the emitter surface. This set of events is considered unlikely given that this position is unusual for a person to do in most settings, such as in a hospital. To further enhance against accidental exposure to UV light to sensitive tissue, the system in accordance with one embodiment may use motion, sound, and distance sensing, or a combination thereof, in order to detect or hear movement or presence. Upon movement or presence detection, a dirty flag may be set in the system and the UVC output may be disabled.

VI. Alternative Light Fixture

In one embodiment of the present disclosure, a light fixture is provided for directing light toward a surface of a room. Such a light fixture in accordance with one embodiment is shown in FIGS. 16-28 and generally designated 600. The light fixture 600 may be incorporated into a disinfection system similar to the disinfection system 300, 300' described herein with the exception that the light fixture 600 may be provided in addition to or in place of the light fixture 100, 400. It is to be understood that one or more aspects of the light fixture 600 may be incorporated into the light fixture 100, 400, and that one or more aspects of the light fixture 100, 400 may be incorporated into the light fixture 600. It is also to be understood that one or more aspects described in connection with the light fixture 100, 400, 600 may be absent therefrom, such that any subset of features described in conjunction with the light fixtures 100, 400, 600 may be utilized to form a light fixture in accordance with one embodiment of the present disclosure.

The light fixture 600 in accordance with one embodiment may be similar to the light fixture 100 in many respects. Similar to the light fixture 100, the light fixture 600 may include an air inlet 612, an treatment chamber 610, and an air outlet 614, similar respectively to the air inlet 112, the treatment chamber 110, and the air outlet 114. A fan assembly 640, similar to the fan assembly 140, may direct air 652 through the air inlet 612. The air may be directed through the treatment chamber 610 and treated with UV light from a UV light source 660, which may be similar to the UV light source 160. The fan assembly 640 may facilitate intake of air 652 through the air inlet 612 via a vent 616 and facilitate discharge of air 654 through the air outlet 614 via a vent 618, after the air has been treated in the treatment chamber 610. In the illustrated embodiment, the fan assembly 640 includes four fans disposed proximal to each other and near the air outlet 614. The number and positions of the fans may vary depending on the application.

The light fixture 600 may include a support member 650 similar to the support member 150 for supporting the light fixture 600 in a room area 50.

The light fixture 600 in the illustrated embodiment may include one or more baffles 632 disposed proximal to the air inlet 612 and the air outlet 614. The one or more baffles 632 may be similar to the one or more baffles 132 described in connection with the light fixture 100. For example, the one or more baffles 632 may be arranged to substantially prevent leakage of UV light from the treatment chamber 610 through the air inlet 612 and the air outlet 614.

In the illustrated embodiment, the light fixture 600 includes a filter assembly 642 similar to the filter assembly 116 described in conjunction with the light fixture 100 in many respects. The filter assembly 642 of the light fixture 600 may be proximal to the air outlet 614 rather than the air inlet 612. Additionally, or alternatively, a filter assembly similar to the filter assembly 642 may be disposed proximal to the air inlet 612 of the light fixture 600.

The light fixture 600 may include a control system 690 that is similar in many respects to the control system 200 described herein in conjunction with the light fixture 100. The control system 690 may be configured to control operation of the light fixture 600, including operation of the UV light source 660. For instance, the control system 690 may include a UV light power source operable to control the supply of power to the UV light source 660 to generate UV light.

The control system 690 may be operably coupled to a sensor system 624, similar to the sensor system 224 described in conjunction with the light fixture 100. The sensor system 624 may be configured differently from the sensor system 224 such that one or more sensors of the sensor system 224 may be absent and/or the sensor system 624 may include one or more sensors described separately from a sensor system 224 in connection with the light fixture 100.

As an example, the sensor system 624 may include UV light sensor circuitry similar to the UV light sensor circuitry 256. In one embodiment, with the sensor system 624 including a UV light sensor circuitry, the UV light sensor circuitry may be configured to detect UV light within the treatment chamber 610. Such UV light sensor circuitry may be operable to provide a sensor output indicative of a light intensity of the UV light within the treatment chamber 610.

The light fixture 600 in the illustrated embodiment includes a visible light assembly 680 operable to form a portion of the treatment chamber 610. The visible light assembly 680 may be movable to allow at least one of access to the treatment chamber 610 for maintenance and discharge of UV light from the treatment chamber 610 into a room. In instances where the visible light assembly 680 is movable to allow discharge of UV light into the room, the visible light assembly 680 may operate as a UV light regulator similar to the UV light regulator 120 described herein.

Figure 24:
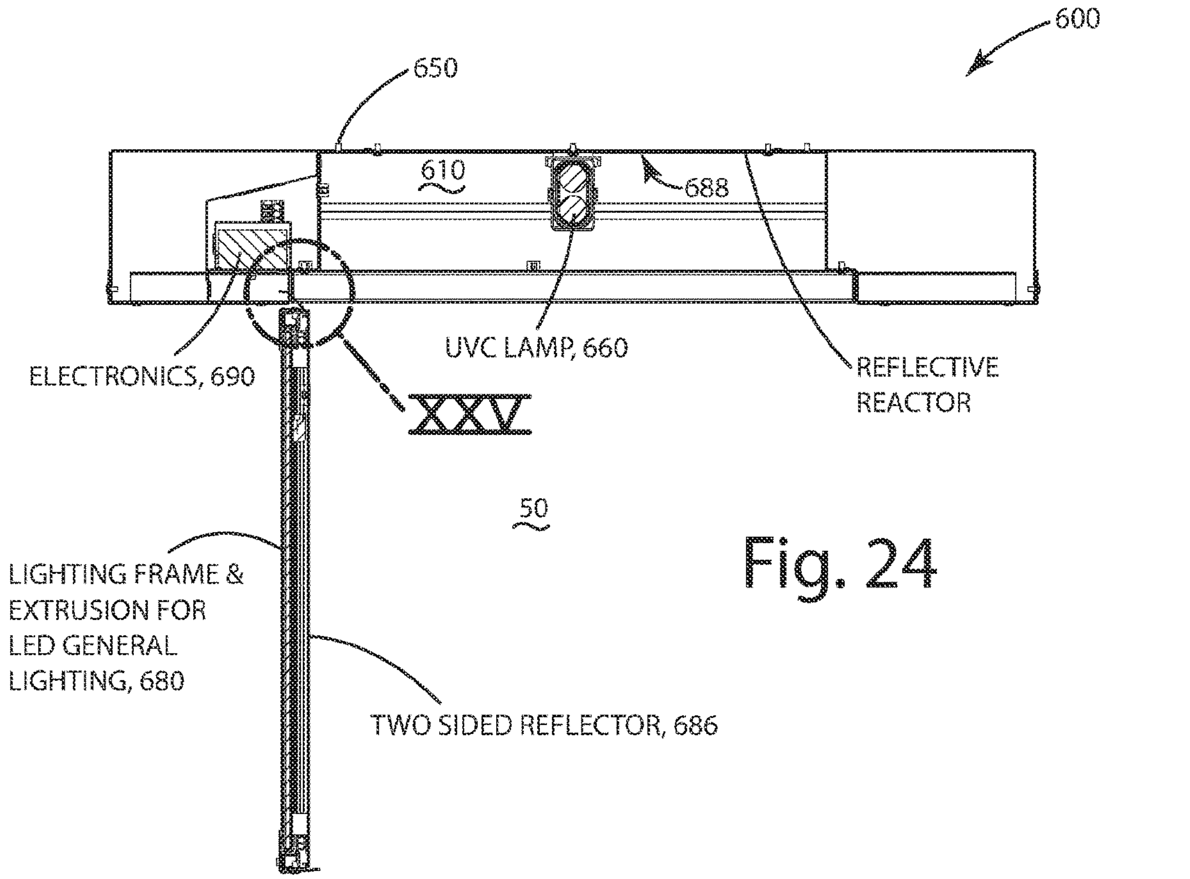
FIG. 24 shows a sectional view of the light fixture of FIG. 16.
Figure 26:
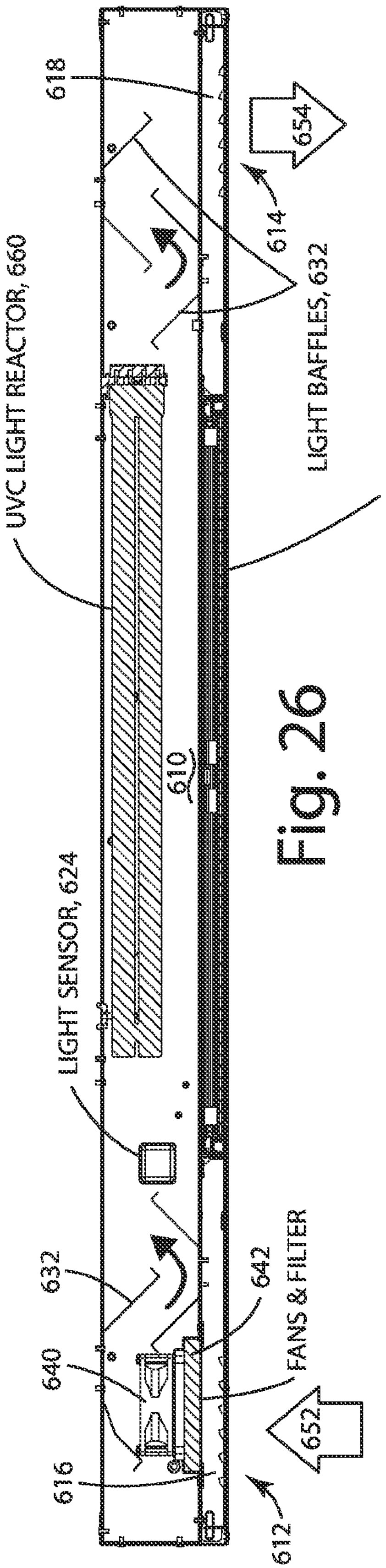
FIG. 26 shows a sectional view of the light fixture of FIG. 16.
Figure 27:
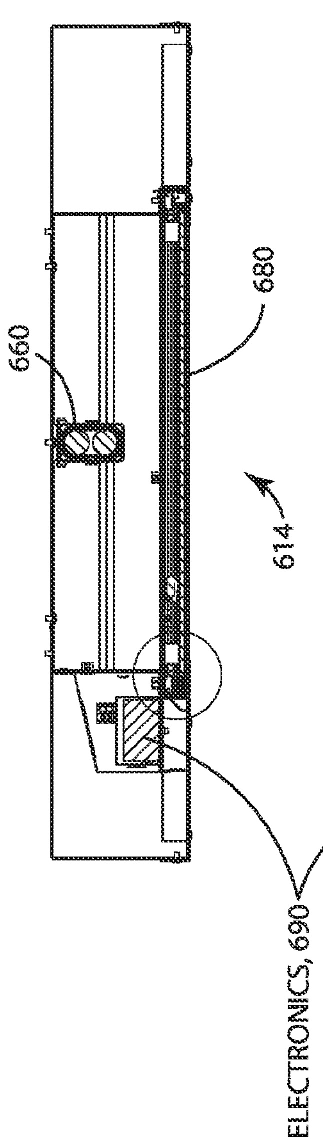
FIG. 27 shows a sectional view of the light fixture of FIG. 16.
Figure 28:
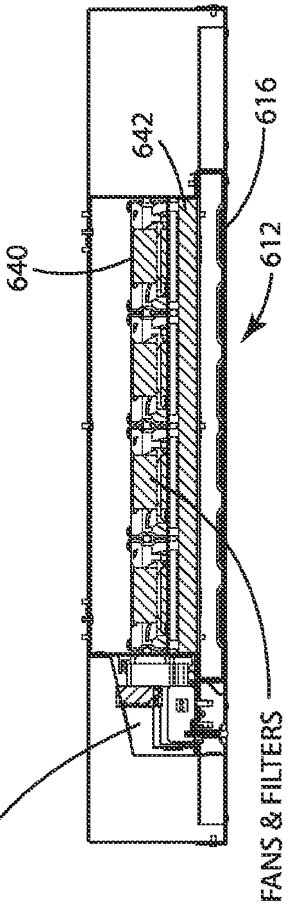
FIG. 28 shows a sectional view of the light fixture of FIG. 16.

The visible light assembly 680 in one embodiment may be movable via manual input from a human between open and closed positions relative to the treatment chamber 610. Additionally, or alternatively, a visible light assembly 680 may be operably coupled to an actuator capable of moving the visible light assembly 680 between the open and closed positions relative to the treatment chamber 610. The illustrated embodiment of FIG. 24 depicts the visible light assembly 680 in an open position, and the illustrated embodiment of FIG. 26 depicts the visible light assembly 680 in a closed position.

Figure 25:
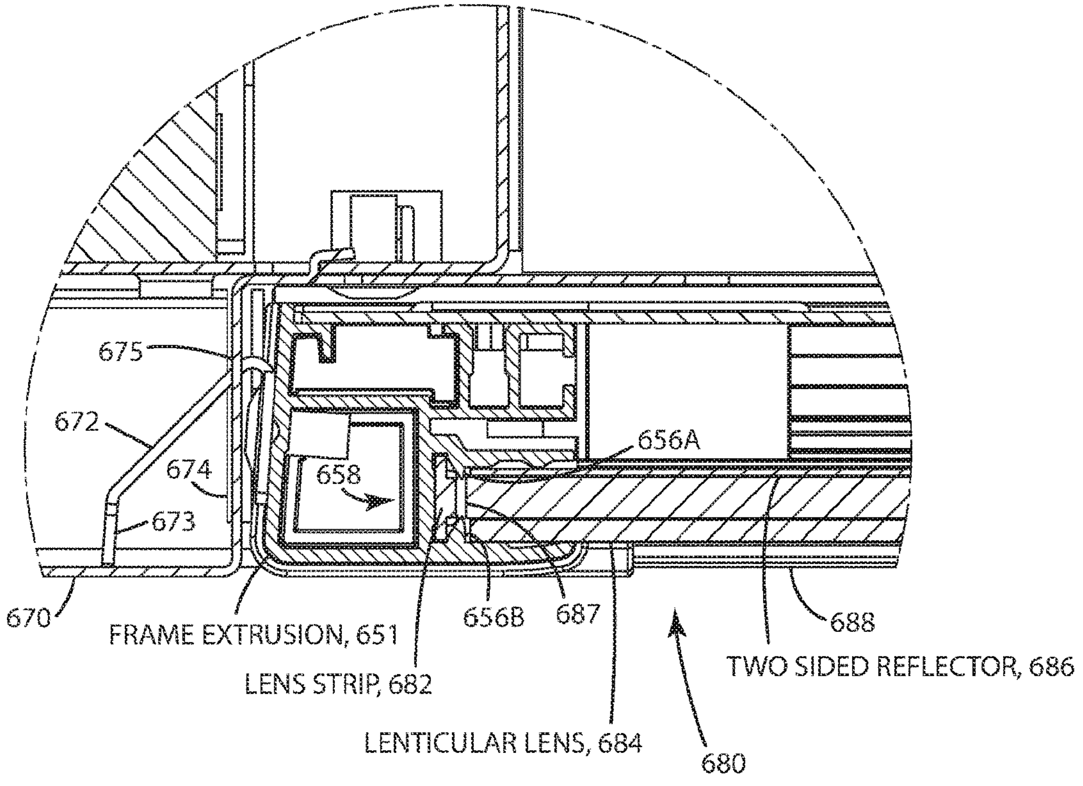
FIG. 25 shows an partial expanded view of FIG. 24.

In the illustrated embodiment of FIG. 25, the visible light assembly 680 can be seen with a hinge 672 operable to allow the visible light assembly 680 to pivot relative to the light fixture 600. The hinge 672 may move within a slot 675 of a frame 670 of the light fixture 600, with an end portion 673 sized larger than the slot 675 to prevent the hinge 672 from allowing movements of the visible light assembly 680 beyond a position defined by engagement of the end portion 673 with the slot 675. The hinge 672 may include an engagement portion 674 attached to the visible light assembly 680 that is operable to couple the hinge 672 to the visible light assembly 680. It is to be understood that the hinge 672 may be configured different from the configuration shown in the illustrated embodiments. It is also to be understood that the visible light assembly 680 may be coupled to the light fixture via more than one hinge 672.

The visible light assembly 680 in the illustrated embodiment may include a reflector 686 operable with the visible light assembly 680 in the closed position to reflect the UV light from the UV light source 660 within the treatment chamber 610. In the illustrated embodiment of FIG. 24 one or more additional surfaces of the treatment chamber 610 may include reflective aspects, such as a reflector 688 provided opposite the reflector 686. The reflectors 686, 688 may cooperate to enhance disinfection of air within the treatment chamber 610.

In one embodiment, the reflector 686 of the visible light assembly 680 may include a visible light reflector operable to reflect visible light received from a visible light source 682 toward an area of the room. In this way, the reflector 686 may be a two-sided reflector operable to reflect UV light within the treatment chamber 610 and to reflect visible light toward the room.

The visible light assembly 680 may include a visible light source 682 configured similar to a light source of the visible light module 180 of the light fixture 100. In the illustrated embodiment of FIG. 25, the visible light source 682 may be disposed to direct light in a generally transverse manner relative to a target direction of visible light for the visible light assembly 680. The visible light source 682 may be disposed within a channel 653 of frame assembly 651 of the visible light assembly 680. The visible light source 682 in one embodiment may be a strip, with a plurality of light sources, that is disposed to engage a base surface 658 of the channel 653 and within the channel 653 along a length of the frame assembly 6510. The visible light source 682 may be captured within the channel 653 by first and second protrusions 656A-B spaced away from the base surface 658 of the channel 653.

A visible light director 684 may be disposed at least partially within the channel 653 as depicted in the illustrated embodiment of FIGS. 16-28. The channel 653 of the frame assembly 651 may support the visible light director 684 such that a portion of a room facing surface 688 of the visible light director 684 is exposed to the room to facilitate directing visible light into the room. The visible light director 684 may include a side surface 687 (e.g., a perimeter surface) operable to receive light from the visible light source 682. In the illustrated embodiment, light received via the side surface 687 may be directed within the visible light director 684 and transverse relative to the side surface 687 toward the room facing surface of the reflector 688.

In the illustrated embodiment, the visible light director 684 is a lenticular lens operable to facilitate directing light received from the visible light source 682 within the channel 653 toward the room facing surface of the reflector 688 and into the room. An example of a lenticular lens is shown in the illustrated embodiment of FIGS. 31A-B and 33A-B. The lenticular lens may include one or more physical aspects (e.g., holes or depressions) that facilitate directing light from within the lenticular lens to an external area. The lenticular lens may be disposed proximal to reflector 686, 688, as discussed herein, and may receive light from one or more light sources 683, which may be disposed at one or more sides of the lenticular lens.

In the illustrated embodiment, the lenticular lens includes depressions 693 (e.g., micro domes) that vary in size along at least one axis 692 of the lenticular lens, and facilitate directing a substantially uniform amount of light from the lenticular lens despite a light source 682 being provided at an edge of the lenticular lens. For instance, the depressions 693 may be shallower in depth 695 closer to the light source 682, and deeper in depth 695 farther away from the light source 682. The shallower depressions 693 may direct, external to the lenticular lens, a smaller portion of more intense light that is closer to the light source 682. And the deeper depressions 693 may direct a larger portion of less intense light that is farther form the light source 682. There may be a type of inverse relationship between depth 695 of the depression and distance from the light source 682 in order to facilitate directing light external to the lenticular lens that is considered generally uniform across a surface 697 of the lenticular lens. The depressions 693 may be formed in a variety of ways, including laser drilling.

The lenticular lens in accordance with one embodiment may enable disposing a light source 682 in proximity to an edge of the lenticular lens, saving space and reducing cost, while being capable of directing light in a transverse manner to the surface 697. The spacing 696 of the depressions 693 may depend on the configuration of the lenticular lens, including an intensity of the light source 682 and the surface area of the surface 697. In one embodiment, the lenticular lens may include first and second light sources 682 disposed at opposite sides of the lenticular lens. In this configuration, the depth 695 may be deeper near the midpoint between the two sides than the depth 695 proximal to each side, as depicted in the illustrated embodiment of FIG. 31B.

The lenticular lens is described herein in conjunction with a light source 683 that generates visible light. It is to be understood that the present disclosure is not so limited, and that the light source 683 may include alternative or additional types of light sources. For instance, the light source 683 may include a UV light source 689 or an IR source 699, or both. Energy from the UV light source 689 and/or the IR source 699 may be directed to one or both of the surfaces 696, 697 of the lenticular lens. For instance, the IR source 699 may be used to direct IR light into the room area 50 in a modulated manner for communication. Such communication by be used for asset tracking conjunction with IR sensors disposed in the room area 50. Energy from the UV light source 689 may be directed into the room area 50 for disinfection purposes, such as when a sensor system indicates there are no people within the room area 50.

In the illustrated embodiment of FIG. 31, an edge lighted lens configuration in accordance with one embodiment of the visible light assembly 680 is depicted. The optics may allow the light guide or lens to have tens of thousands of optical holes that change the direction of the light output from the light source 683 (e.g., from LED lights). The printed circuit board assembly (PCBA) associated with the light source 683 may include LEDs that generate one or more types of energy, such as IR, UV or color and white lights. The IR may be used for asset tracking systems to identify a room. A network and WiFi system may be used with asset tracking sensors to identify a code of IR light within the room or area. The PCBA may be held by an extrusion that serves as a heatsink and a structural frame, and may be driven by a PWM circuit or a general ballast of a driver, depending on the application. The UV light source 689 may generate UV energy that may be mixed with visible lighting and IR for use in time driven by the controller and potentially only when occupancy is proven to be void of people or animals.

In one embodiment, the lenticular lens may also be configured to allow light to pass through from one surface 696 to another surface 697 and external to the lenticular lens. As an example, the lenticular lens may be configured to direct visible light from an edge located light source 683 in a transverse manner to a lower surface 697 of the lenticular lens. Additionally, the lenticular lens may be configured to direct UV light from an upper surface 696 to the lower surface 697 in a substantially straight-through manner.

Figure 32:
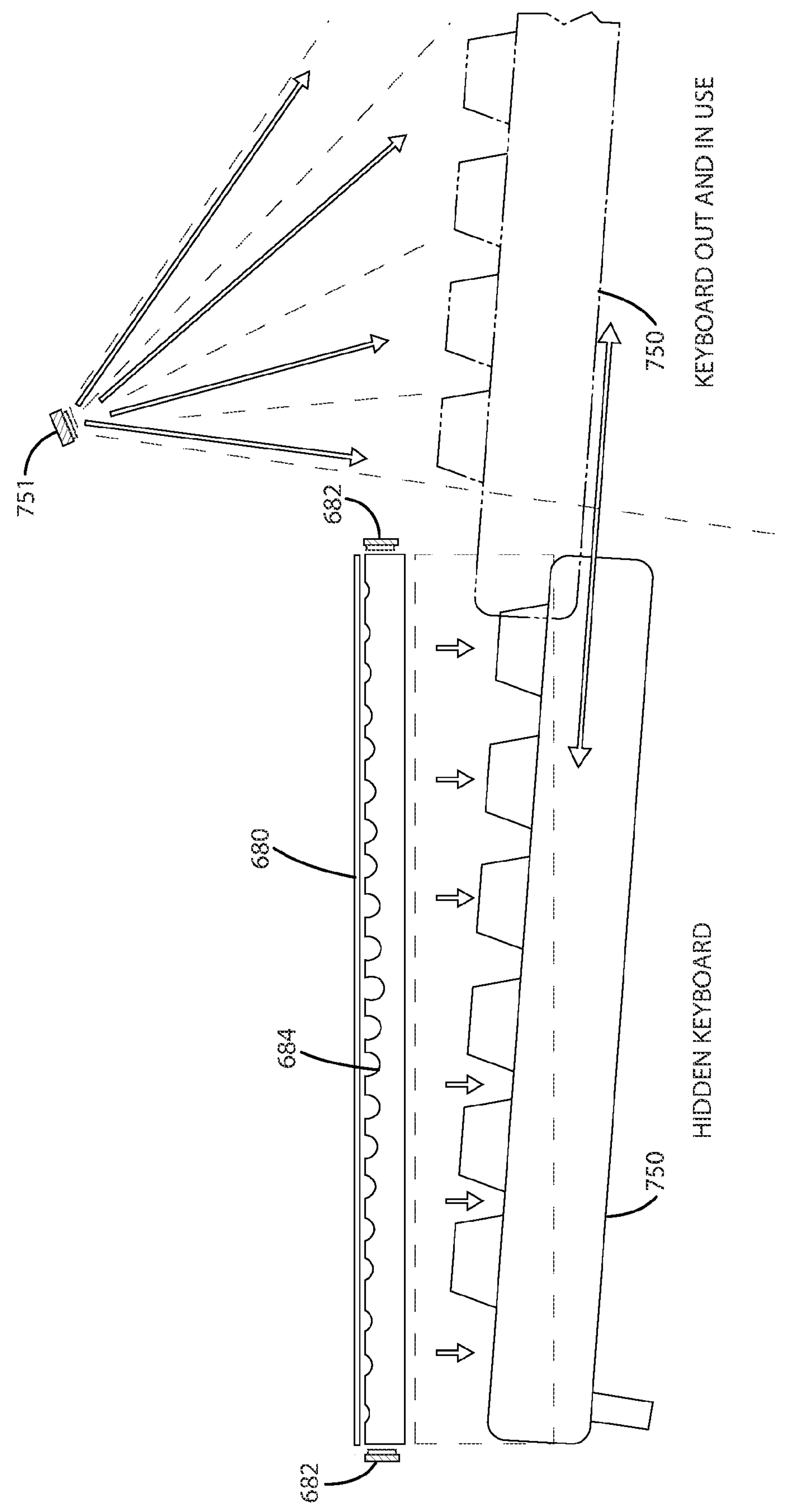
FIG. 32 depicts the light module of FIG. 31 being used as a low clearance light and disinfecting system.
Figure 33B:
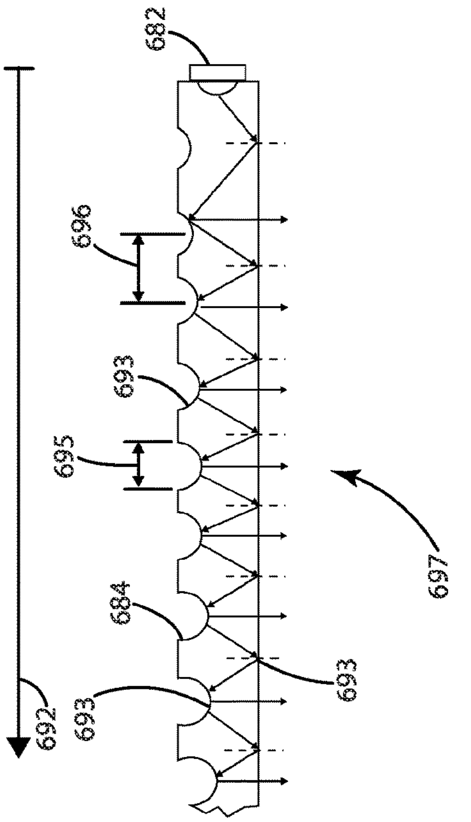
FIGS. 33A-B shows a lenticular lens of the light module of FIGS. 31A-B in accordance with one embodiment of the present disclosure.
Figure 33A:
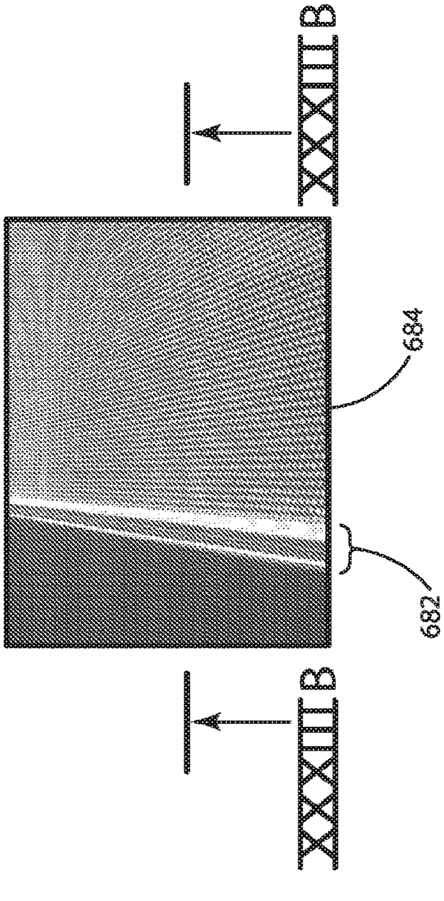

It is to be understood that, although the visible light module 680 is described in conjunction with an air treatment assembly, the present disclosure is not so limited. The visible light module 680 with the lenticular lens may be configured for a variety of uses, some of which may not include a visible light source and instead generate only UV light with the light source 682 including UV light sources. In the illustrated embodiment of FIG. 32, the lenticular lens configuration with a light source 682 configured for UV light (optionally also visible light) is shown for a low profile disinfection area associated with a keyboard 750 or another type of user interlace The lenticular lens may be provided in a low profile keyboard storage area. This area can be lighted with general visible lighting to see and also UV energy for UV disinfection. When the keyboard 750 is pulled out an open area disinfecting array 751 may be used to disinfect the keyboard 750. A sensor on a keyboard slide, such as a magnetic sensor, may be used to sense in vs. out, and as a basis for controlling operation of the light source 682 (e.g., to output visible and/or UV energy).

The frame assembly 651 may be formed by multiple extruded components that define the channel 653 and that can be joined by corner supports 659. In the illustrated embodiment, the frame assembly 651 is a rectangular component with four corner supports 659 and four extruded components disposed respectively between each corner support 659. The frame assembly 651 may include the channel 653 defined about the entire perimeter of the frame assembly 651. It is noted that the visible light source 682 may be disposed within the channel 653 along one or more sides of the frame assembly 651. For instance, the visible light source 682 may be disposed along one side of the frame assembly 651 within the channel 653.

Figure 23A:
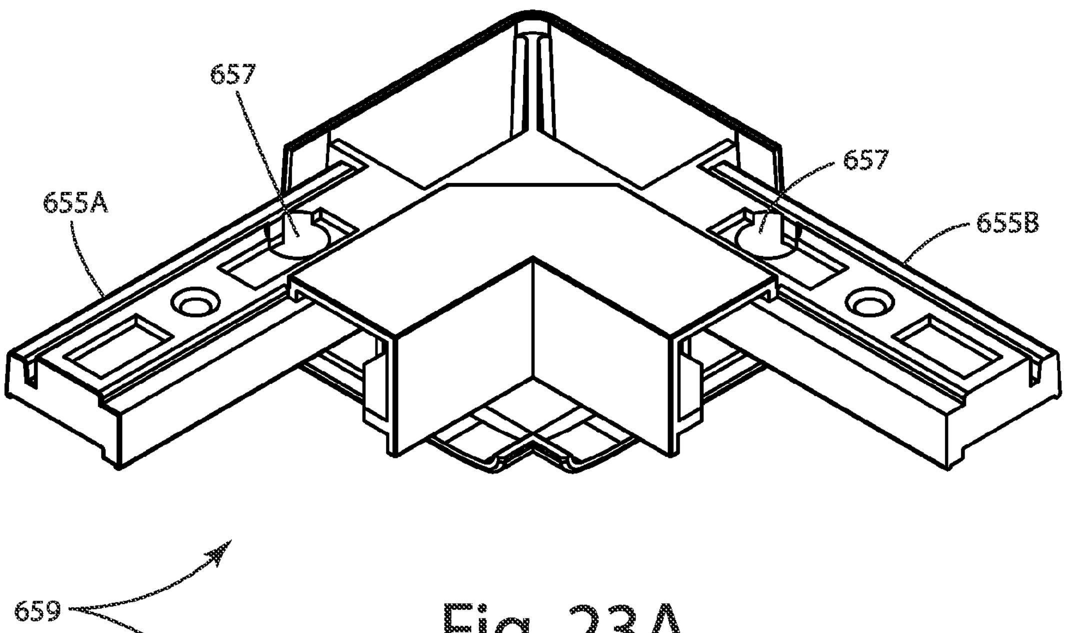
FIGS. 23A-B show multiple views of component of the light fixture in accordance with one embodiment.
Figure 23B:
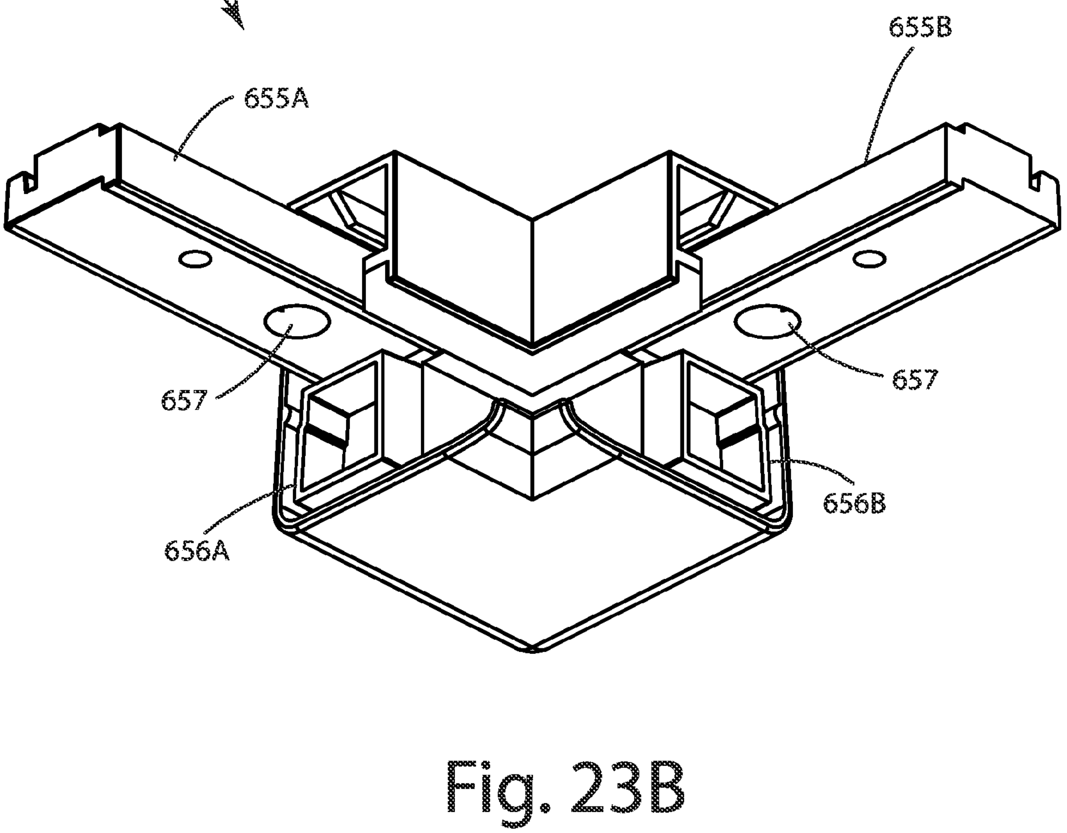

Two views of an exemplary embodiment of a corner support 259 are depicted in FIGS. 23A-B. The corner support 659 may include first and second support extensions 655A, 655B operable to fit within respective extruded components of the frame assembly 651. The corner support 659 may also include a first and second engagement portion 656A, 656B that are also operable to fit within a respective extruded component of the frame assembly 651. The corner support 659 may include apertures 657 to facilitate installation of a fastener (not shown) to connect extruded component to the corner support 659.

Figure 29:
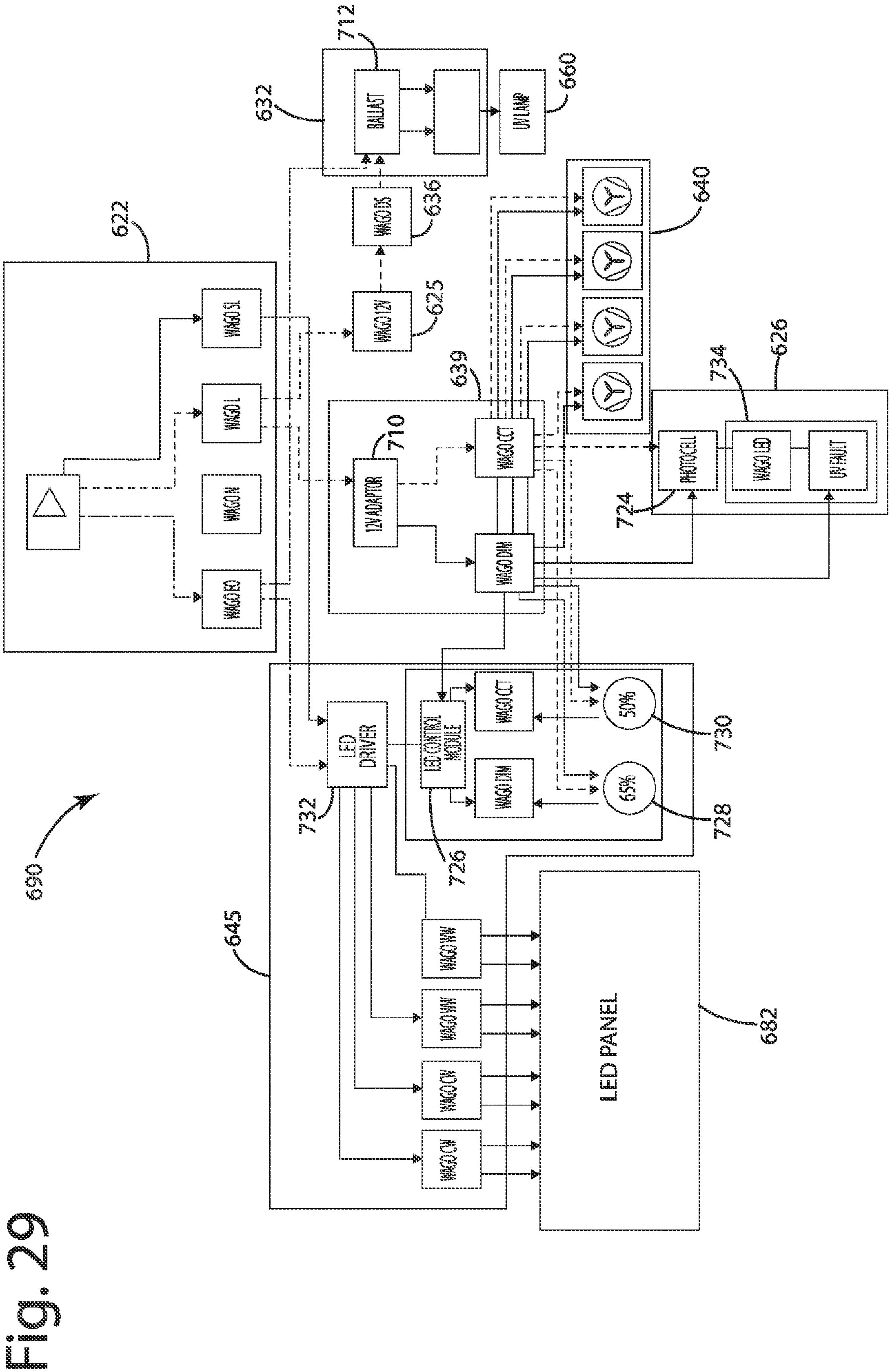
FIG. 29 shows a control system in accordance with one embodiment.
Figure 30:
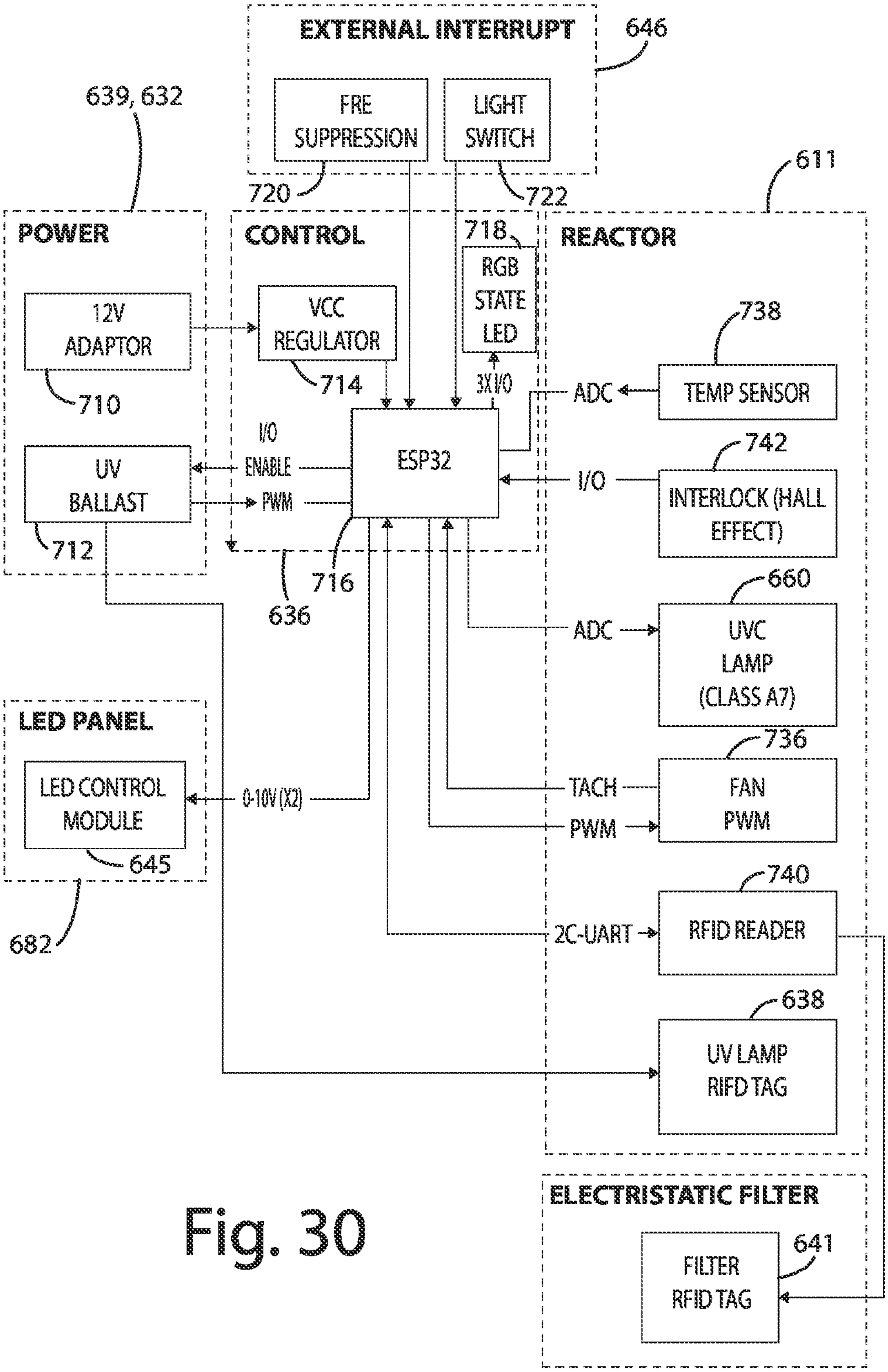
FIG. 30 depicts a control system in accordance with one embodiment.
Figure 31A:
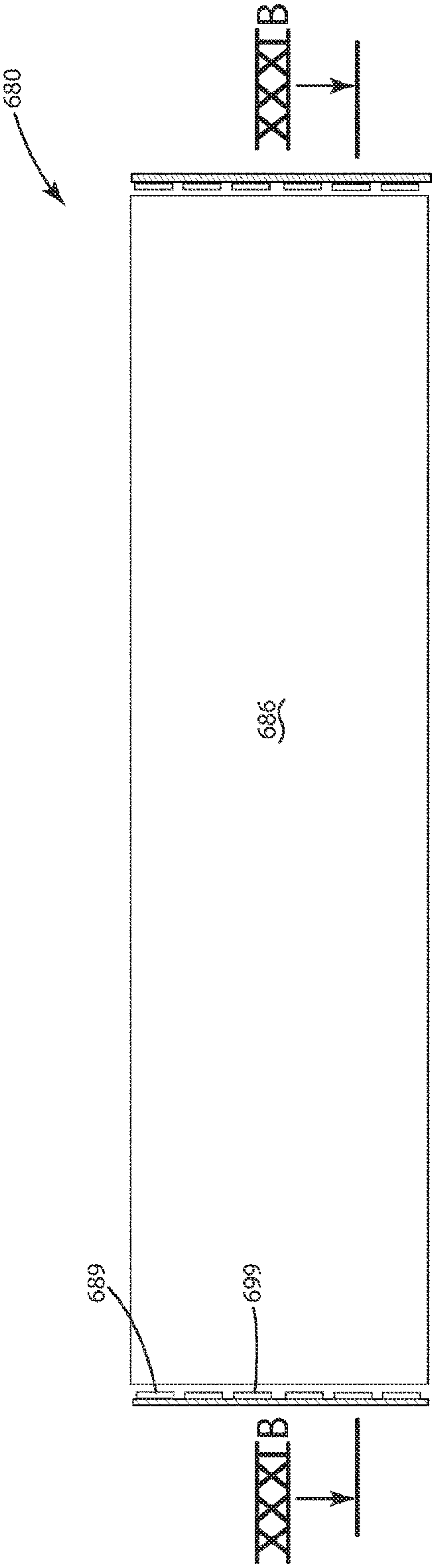
FIGS. 31A-B depict an light module directing light into a lens that is fashioned to direct the light downward and diffuse the light or create a pattern of light downward.
Figure 31B:
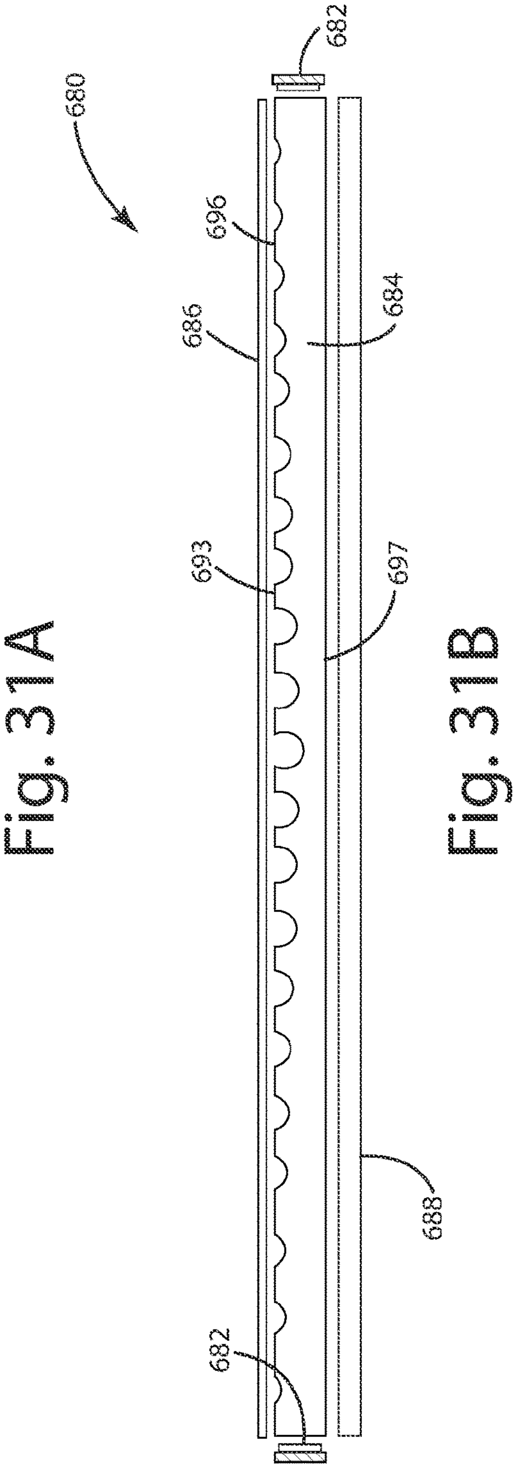

Turning to the illustrated embodiment of FIGS. 29 and 30, the light fixture 600 may include a control system 690 similar to the control system 200 described herein in many respects. It is noted that the control system 690 in the illustrated embodiment depicts connections between components in a variety of ways and groups components in different ways. It is understood that the groupings are not limited; instead the groupings are provided for purposes of disclosure to facilitate discussion and understanding of the operational aspects of components of the control system 690 and coordination of such operational aspects between various components of the control system 690.

In the illustrated embodiment, the control system 690 may include a power source 622, similar to the power source 152, and capable of delivering power from an external source and/or from a portable source such as a battery. In the illustrated embodiment, the power source 622 includes utility power in the form of an equipment ground, neutral, and line connections (e.g., for 120 VAC power). The power source 622 may also include a switched line connection operable to supply power to a visible light driver 645, which may be similar to the visible light driver 245 discussed herein. The switch line connection may be provided by a switch (not shown) similar to the switch 154 described in connection with the light fixture 100.

The control system 690 may also include power management circuitry 639 similar to the power management circuitry 239. The power management circuitry 639 may include a DC power source 710 operable to receive power from the power source 622 and convert the received power (such as 12 V DC). In the illustrated embodiment, the power management circuitry 639 includes ground and DC power connection or distribution of power to a variety of components of the control system 690, including one or more fans of the fan assembly 640 and control circuitry of the visible light driver 645. The power management circuitry 639 in the illustrated embodiment of FIG. 30 is associated with UV driver circuitry 712 or ballast circuitry capable of applying power in a controlled manner to the UV light source 660.

The control system 690 the illustrated embodiment may include a controller 636, similar to the controller 236 of the control system 200. The controller 636 may direct one or more components of the light fixture 600 for operation, including, for instance, directing output from the visible light source 682 and output from the UV light source 660. The controller 636 in the illustrated embodiment of FIG. 30 may include regulator circuitry 714 for receiving power from the DC power source 710 and converting to received power to a form usable by a microcontroller 716. The controller 636 may include status circuitry 718 operable to indicate one or more states of the controller 636, such as active state.

The controller 636 may be operable to provide one or more control signals to components of the control system 690, including pulse width modulated signals, discrete signals, analog signals (e.g. 0 to 10 V), and serial communications. The controller 636 may also be operable to receive one or more such control signals from other components of the control system 690. Based on these one or more control signals, the controller 636 may determine to change a state of an output control signal to another component or the same component from which a control signal was received.

The control system 690 may include a room sensor interlace 625 similar to the room sensor interlace 255 described in conjunction with the control system 200. For instance, the room sensor interlace 625 may include a door switch capable of generating an output indicative of whether the door of the room area 50 is closed or open. As discussed herein, the state of the door may be used as a basis to determine whether to direct UV light from the UV light source 660 into the room.

The control system 690 may support connections to external interfaces or external circuitry 646, such as fire suppression circuitry 720 or a light switch 722 (which may be similar to the switch 154 in one embodiment). The external circuitry 646 may provide inputs and/or receive outputs from the controller 636 to facilitate operation. For example, the light switch 722 may provide an output to the controller 636, which may direct operation of the visible light source 682 based on the state of the light switch 722. As another example, the controller 636 may control operation of the light fixture according to one or more predetermined states based on activation of fire suppression components as indicated by the fire suppression circuitry 720.

The control system 690 may include sensor and feedback circuitry 626, similar in some respects to the sensor circuitry 256 of the control system 200. The sensor and feedback circuitry 626, for example, may detect presence of UV light or intensity of UV light being generated by the UV light source 660, and provide a sensor output indicative of the detected characteristic to the controller 636. Based on the sensor feedback from the sensor and feedback circuitry 626, the controller 636 may adjust operation of the light fixture 600, such as by increasing or decreasing a power output of the UV light source 660. In one embodiment, the sensor and feedback circuitry 626 may include an error indicator 734, such as an LED indicator, that can be directed to indicate a fault. A fault state may be identified by the controller 636 based on sensor feedback being indicative of the UV light source 660 operating outside of target parameters. The sensor and feedback circuitry 626, additionally or alternatively, may include a photocell or light sensor 724 operable to sense at least one of UV light and visible light. The light sensor 724 may provide a sensor output indicative of an intensity of the sensed light.

The control system 690 in the illustrated embodiment, as discussed herein, may include a visible light driver 645 capable of controlling supply of power to the visible light source 682 in accordance with a target parameter. The visible light driver 645 in the illustrated embodiment includes a light control module 726 which may be incorporated into the controller 636 in one embodiment, but is shown separately in FIG. 29 for purposes of disclosure. The light control module 726 may receive commands from a user similar to the user interface described in conjunction with the visible light driver 245 of the control system 200. For instance, the light control module 726 may receive a brightness command from a dimmer control element 728, and may receive a color temperature command from a color control element 730. The dimmer control element 728 and the color control element 730 may be incorporated into a user interface provided on a smart phone or may be provided on an interface installed within the room area 50. In one embodiment, the electronics of the LED drivers, ballast drivers, fan drivers, and IOT control may all be provided in one electronics package to provide a large cost savings over separate configurations and to provide a competitive advantage. This combined electronics configuration can be adapted for AC or DC input voltages.

The visible light driver 645 may include an LED driver 732 operable to supply power in a controlled manner to the visible light source 682. In one embodiment, the LED driver 732, as discussed herein in conjunction with the control system 200, may include a controlled current source and/or a controlled voltage source to supply power to the visible light source 682. In one embodiment, the power supplied from the LED driver 732 may be pulsed width modulated.

In the illustrated embodiment of FIG. 30, the visible light driver 645 may receive an intensity directive from the controller 636 in the form of an analog signal that varies between upper and lower limit, with the upper limit corresponding to an upper intensity level and the lower limit corresponding to a lower intensity level. For example, the intensity directive may be in the range of 0-10 V, with 0 V corresponding to 10% intensity and 10 V corresponding to 100% intensity.

The controller 636 of the control system 690 and illustrated embodiments of FIGS. 29 and 30 is operable to direct operation of the fan assembly 640. As an example, the controller 636 may direct the power management circuitry 639 to supply power to fans of the fan assembly 640.

The control system 690 of the light fixture 600 may include reactor circuitry 611, including, for example, the UV light source 660. The reactor circuitry 611 in the illustrated embodiment of FIG. 30 includes fan control circuitry 736 operable to supply power in a controlled manner to the one or more fans of the fan assembly 640. The fan control circuitry 736 may provide feedback in the form of pulses (e.g., tachometer pulses) indicative of a rate of rotation of one or more fans of the fan assembly 640. This feedback may be provided to the controller 636, which may supply a fan speed control signal (e.g., a pulse width modulated signal) to the fan control circuitry 736. The fan control circuitry 736 may supply power to one or more fans of the fan assembly 640 in accordance with the fan speed control signal.

The reactor circuitry 611 in the illustrated embodiment includes a temperature sensor 738 (e.g., a thermistor) operable to provide a signal to the controller 636 indicative of an internal temperature of the reactor or air treatment chamber 610. In one embodiment, two thermistors may be utilized to monitor airflow. Alternatively, or additionally, a tachometer output from each fan may be provided for preventive maintenance, service tracking, and determining airflow. Conventional pressure sensors for low air velocities can be inaccurate and cost prohibitive. One embodiment according to the present disclosure includes thermistors to provide the a more accurate and/or more cost effective system for measuring low air velocity. The two sensors may be connected to a Wheatstone bridge to identify the difference in temperature. One of the sensors may be coated to allow less impact of the wind or airflow and measure the basic temperature. The resultant difference is air flow cooling the thermistor.

The reactor circuitry 611 may include an RFID reader 740 configured to detect or read information from a RFID tag 641 associated with the filter assembly 642. In one embodiment the RFID reader is configured for operation at about 125 kHz, The RFID information may be conveyed to the controller 636. Additionally, or alternatively, the controller 636 may transmit information for storage on the RFID tag 641 of the filter assembly 642. Information such as a time of use of the filter assembly 642 may be tracked by the controller 636 to allow the controller to determine whether one or more criteria associated with the filter assembly 642 are satisfied. For example, criteria such as being used beyond a specified amount of time may trigger a state recommending replacement of the filter assembly 642. The reactor circuitry 611 in the illustrated embodiment may include a RFID tag 638 associated with the UV lamp 660, which may be similar to the RFID tag 238 described in conjunction with the control system 200.

In the illustrated embodiment of FIG. 30, the reactor circuitry 611 includes an interlock 742 operable to provide feedback to the controller 636 indicative of a state of the reactor or treatment chamber 610. For example, the interlock 742 may be indicative of whether the visible light module 680 is in the closed or open position. In one embodiment, if the interlock 742 is indicative of the visible light module 680 being opened, the controller 636 may be prevented from activating the UV light source 660.

VII. Combination Lamp Air Disinfection System

One aspect of the present disclosure relates to a light assembly having an air disinfection system for pathogen reduction. For instance, the light assembly can include a visible light source, a lamp housing element having a cavity, and an air disinfection system installed within the cavity, wherein the air disinfection system includes a UV light source and the cavity forms a UV light disinfection chamber with an air intake for receiving untreated air and an air outlet for outputting air treated by the UV light source.

The lamp can be essentially type of lamp that can be adapted to include an air disinfection system. For example, the lamp can be a portable light assembly, such as a table or floor lamp that includes a lamp shade having a cavity capable of fitting air disinfection components and forming a suitable UV light disinfection chamber. For example, some portable lamps have a shade assembly that forms a cavity. Some portions of the shade assembly may be opaque to visible light (e.g. a steel surface) and other portions of the shade assembly may be transmissive to visible light (e.g. a light diffusion plate). The shade assembly may be entirely or partially opaque or reflective to UV light. Shade assembly surfaces (internal, external, or both) may be coated, in part or fully, with a coating that gives the shade assembly, or portions thereof, UV reflective properties. The UV reflective properties can assist in converting the shade assembly cavity into a UV air treatment chamber.

Figure 34A:
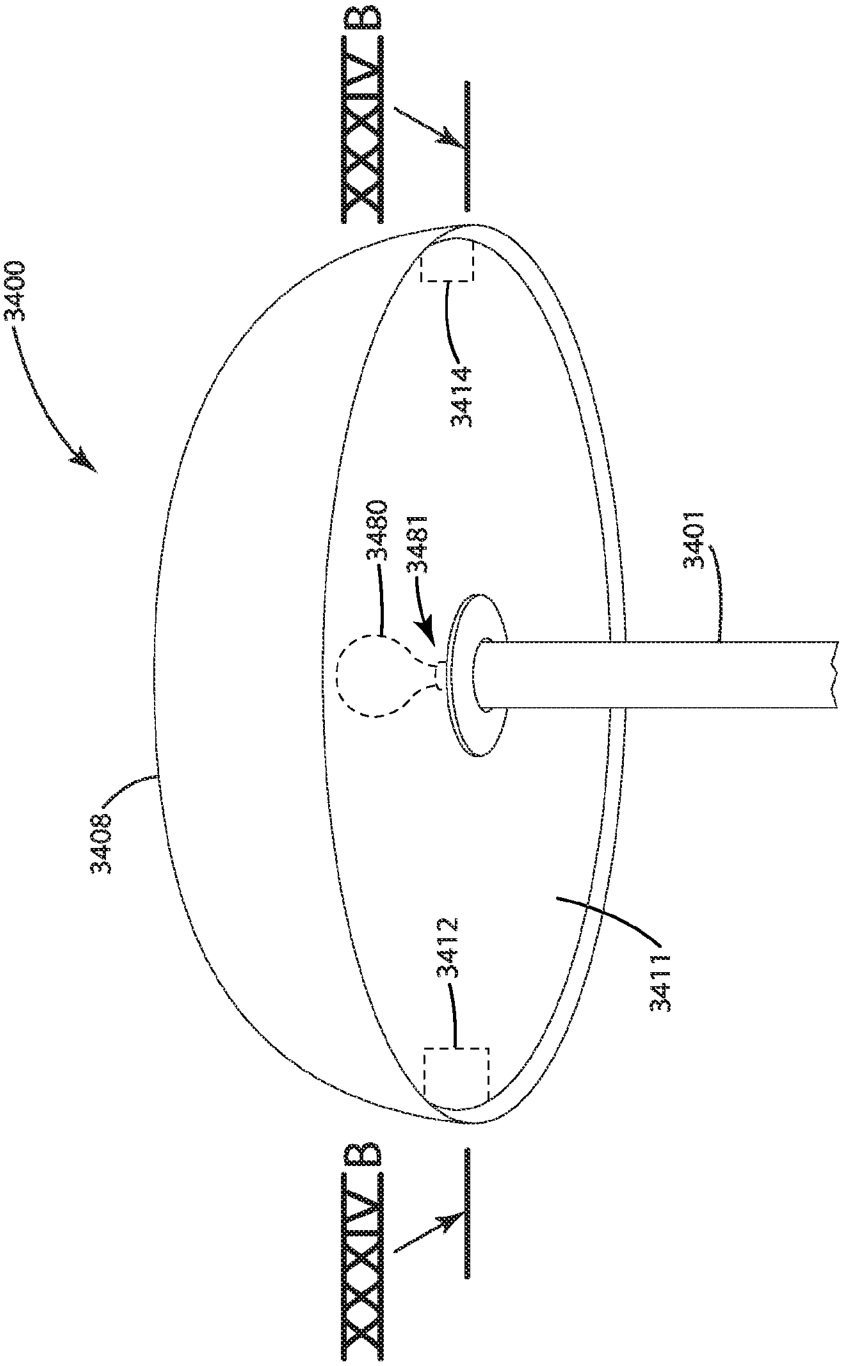
FIG. 34A shows a perspective view of a portable visible light air disinfection assembly in accordance with one embodiment of the present disclosure.
Figure 34B:
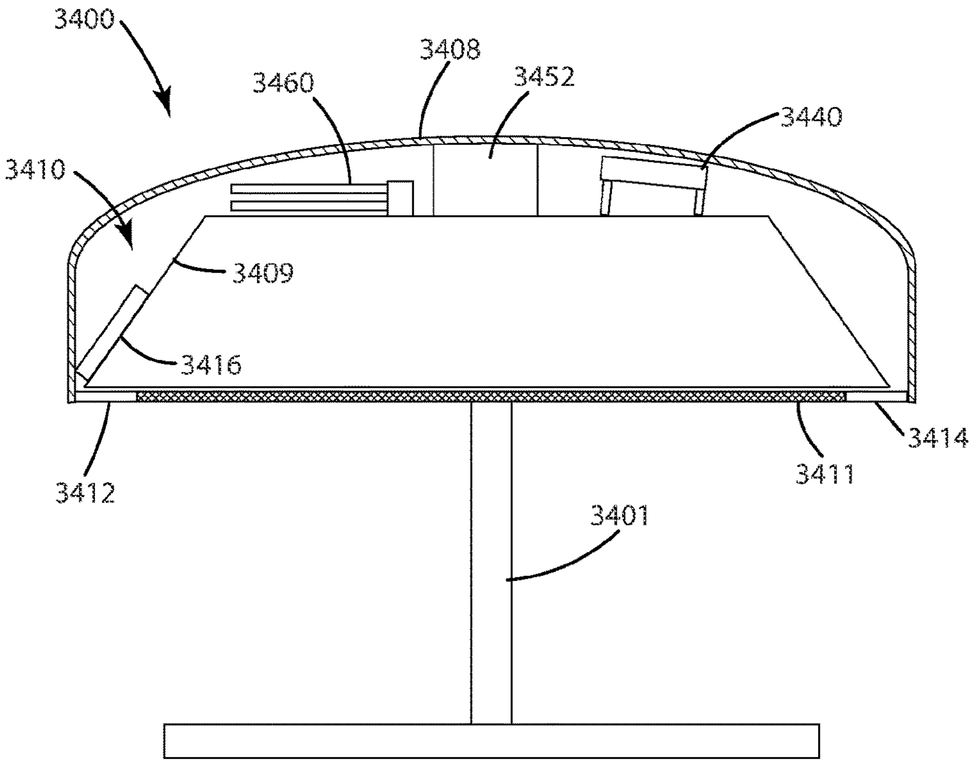
FIG. 34B shows a side sectional view of a the FIG. 34A embodiment.
Figure 34C:
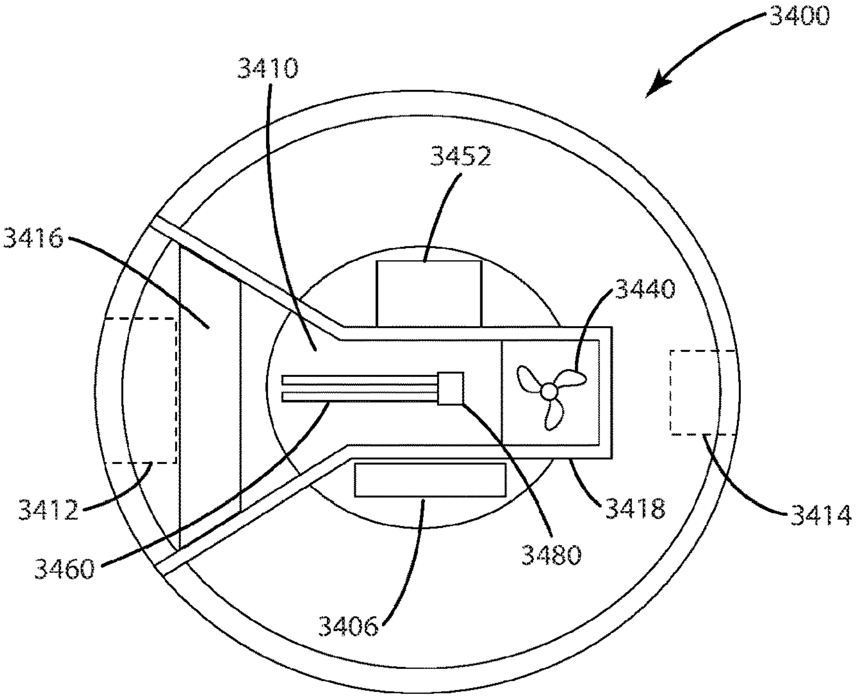
FIG. 34C shows a top sectional view of the FIG. 34A embodiment.

One example of a combination lamp air disinfection system is illustrated in the table lamp of in FIGS. 34A-C. FIG. 34A illustrates a side partial perspective view of the table lamp, while FIGS. 34B and 34C show representative sectional views. The air disinfection system is integrated within the cavity formed by the lamp shade assembly. In this instance, the top metallic surface 3408 of the lamp shade assembly and the lens 3411 cooperate to form an open air cavity capable of fitting the air disinfection components.

The body 3401 of the lamp can be used to conceal and route wires for power and control functions. The body 3401 of the lamp in some instances can be utilized to control lamp functionality (e.g. turn on and off the visible light, and turn on and off the UV light, or otherwise control lamp/air disinfection functionality). For example, the body 3401 can include capacitive sensors that control the desired functionality or physical buttons or other actuators can be integrated (or disposed on the lamp body 3401).

The lamp's visible light source 3480 can be mounted to a socket 3481 that is disposed within the lamp cavity formed by the lamp shade assembly. The socket can be coupled directly to the base, to a harp holder that is screwed to a threaded tube, or otherwise joined to the lamp shade assembly or base. In some embodiments, a lamp harp (not shown) may be included for supporting the interior structure 3409 or a portion thereof, e.g. where the interior structure 3409 is a distinct structure from the lamp shade assembly. In some embodiments, the interior structure 3409 cooperates with the metallic surface 3408 to form the cavity 3410. In other embodiments, the metallic surface 3408 cooperates with the diffusal plate 3416 to form the cavity 3410. For example, the metallic surface 3408 and lens 3411 can be coupled together and supported by the body 3401 to form a single open air chamber or two separate open air chambers separated by interior structure 3409.

The lamp's visible light source 3480 can be disposed within the lamp shade assembly cavity 3410 and because portions of the lamp shade assembly are metallic (e.g. steel), visible light is reflected and directed toward the lens 3411 onto a table in a user's vicinity. The visible light may be directed toward a lens 3411 of the lamp, which may diffuse light prior to being provided onto a table in a user's vicinity. A similar configuration can be provided in the form of a floor lamp where the body includes a pole that forms a pendant lamp configuration (See FIG. 35A-B) with the pole connecting to the top of the shade. The air disinfection system can be integrated with the lamp assembly during manufacture or retrofit into an existing lamp assembly.

The lens 3411 may be disposed proximal to the bottom of the interior surface 3409 and the wall 3408. The lens 3411 may be a sheet of light transmissive material capable of diffusing light from the lamp prior to being provided to a table or other surface.

FIG. 34B illustrates a side sectional view and FIG. 34C illustrates a top sectional view. The air disinfection system can include a germicidal light source 3460 that is operable to generate UV light. The air disinfection system can also include a UV treatment chamber 3410 having an untreated air inlet 3412 and a treated air outlet 3414, the UV treatment chamber having an air treatment region operable to receive air from the untreated air inlet and to direct air to the treated air outlet, wherein the UV light from the germicidal light source 3460 is directed to the air treatment region.

The UV treatment chamber 3410 can be defined at least in part by a wall 3408 of the portable light assembly. For instance, the portable light assembly 3400 may include a lamp shade having a shell configuration that can be adapted to form a UV chamber 3410. The wall 3408 is substantially opaque with respect to the UV light that is output from the germicidal light source 3460. In one embodiment, the wall 3408 is metal or metal-like and substantially opaque to all light. In alternative embodiments, the wall 3408 may be substantially opaque with respect to the UV light, but allow diffusal of visible light. The components of the UV air treatment system can be concealed within the UV chamber. If the lamp shade is not opaque to visible light, the UV treatment components can be positioned within the shade shell so as not to significantly interrupt the diffusal of visible light through the shade or to strategically interrupt visible light to allow for diffusal in an aesthetically pleasing manner.

The UV treatment chamber 3410 can be defined at least in part by a wall 3409 in particular the interior wall 3409 of the portable light assembly. For instance, the portable light assembly 3400 may include a lamp shade having a shell configuration that can be adapted to form a UV chamber 3410. The wall 3409 can be substantially opaque with respect to the UV light that is output from the germicidal light source 3460. In one embodiment, the wall 3409 is metal or metal-like and substantially opaque to all light. In alternative embodiments, the wall 3409 may be substantially opaque with respect to the UV light, but allow diffusal of visible light. The components of the UV air treatment system can be concealed within the UV chamber. If the lamp shade is not opaque to visible light, the UV treatment components can be positioned within the shade shell so as not to significantly interrupt the diffusal of visible light through the shade or to strategically interrupt visible light to allow for diffusal in an aesthetically pleasing manner. In one embodiment, the bottom surface of the interior wall 3409 of the portable light assembly can be a visible light reflector for the visible light source 3480 of the portable light assembly.

The portable lighting assembly 3400 may include a treatment chamber 3410 through which air may be directed and in which the air may be treated with UV light from a UV light source 3460. The UV light source 3460 may be a germicidal light source operable to generate the UV light in response to being supplied power from the power source 3452. For example, the UV light source 3460 may be a UV-C source, such as a cold cathode lamp, a low pressure mercury lamp, or UV-C light emitting diodes.

The UV treatment chamber 3410 can include a gasket interlace 3418. The gasket interlace 3418 can be disposed between an external wall 3408 and internal wall 3409 of the lamp shade. That is, the UV treatment chamber can include a gasket interlace coupled to a wall of the UV treatment chamber. The gasket interlace can be operable to contact a portion of the portable light assembly. The gasket can be configured to substantially prevent leakage of the UV light that is output from the germicidal light source 3460 to an external environment and to prevent leakage of air. The gasket interface can be a C-shaped gasket that receives a wall of the UV treatment chamber and seals against the wall of the portable light assembly. The C-shaped gasket can form a compression seal with the wall or walls of the portable light assembly. The UV chamber can be defined by a combination of the gasket interface 3418 and the lamp shade walls 3408, 3409.

The power applied to the UV light source 3460 may be a conditioned form of the power from the power source 3452. For instance, the power source 3452 may be operable to supply AC power. The portable light assembly 3400 may include circuitry to condition the AC power into DC power sufficient to operate the UV light source 3460. The DC power may be constant or pulsed depending on the operating specification and target parameters for the UV light source 3460. In DC pulsed configurations, the power may be variable such as by varying the DC pulse between 90% to 30% to supply power in accordance with a target operating parameter.

In one embodiment, untreated air may enter the treatment chamber 3410 via an air inlet 3412, and treated air may exit the treatment chamber 3410 via an air outlet 3414. The air inlet 3412 may be in fluid communication with a filter assembly 3416, which may be configured to filter particulates from the untreated air prior to being treated by UV light in the treatment chamber 3410. The filter assembly can include a filter having a minimum efficiency reporting value (MERV) selected in accordance with the application. For instance, in some embodiments the filter is a MERV6 filter. Removal and replacement of the filter assembly 3416 may be conducted on a periodic basis to prevent substantial clogging of the filter assembly 3416 or other maintenance benefits. The untreated air inlet 3416 and treated air outlet 3418 can be defined at least in part by a wall 3408, 3409 of the portable light assembly 3400. The cross-sectional area of the untreated air inlet 3416 can be greater than a cross-sectional area of the treated air outlet 3414 to facilitate air flow through the UV chamber.

In one embodiment, the filter assembly 3416 may be disposed such that one or both sides of the filter assembly 3416 are in a path of light from the UV light source 3460. This way, UV light may be directed to the filter assembly 3416 to decontaminate all or a portion of the filter assembly 3416. The UV light applied to the filter assembly 3416 may be selectively applied, or the filter assembly 3416 may be disposed to receive light from the UV light source 3460 while the UV light source 3460 is active. The filter assembly 3416 can be disposed within the air flow path between the air inlet 3412 and the UV treatment chamber 3410.

As discussed herein, treated air may exit the treatment chamber 3410 via an air outlet 3414. The air outlet 3414 may include a vent configured to allow airflow therethrough at a flow rate sufficiently greater than a flow rate of the treated air. In other words, the vent may be configured to substantially avoid restricting airflow through the treatment chamber 3410. The vent may include a plurality of openings each sized to substantially prevent entry of improper objects (e.g., hands and fingers) into the treatment chamber 3410.

The portable light assembly 3400 may include a fan assembly 3440 operable to direct air through the treatment chamber 3410 from the air inlet 3412 to the air outlet 3414. In the illustrated embodiment, the fan assembly 3440 is disposed proximal to the air outlet 3414; however, it is to be understood the present disclosure is not so limited. The fan assembly 3440 may be disposed or provided in a different position to direct air through the treatment chamber 3410. The fan assembly 3440 may include a fan operable to direct air through the treatment chamber 3410 at a target flow rate for disinfection or decontamination of the air via application of UV light within the treatment chamber 3410. As an example, the target flow rate may be 50 CFM. in one embodiment, the fan assembly 3440 may be variable such that a flow rate of air through the treatment chamber 3410 may be increased or decreased under direction of a control system 200 of the lamp assembly 3400. For instance, the portable light assembly 3400 including the air disinfection system may be controlled remotely, via a wired or wireless connection. Control may be provided over a power connection to the lamp assembly or via a separate control connection.

In one embodiment, the portable light assembly 3400 may include driver circuitry 3406 for the UV light source 3460 or the visible light module 3480, or both, under control of a local controller or a remote controller 200, located elsewhere at the location of the portable light assembly 3400 or at a remote server connected via the Internet. The driver circuitry 3406 may be a lamp driver driven by a PWM output of the controller 200. The UV light or the visible light, or both, may provide data signaling by producing pulses or gaps in the light that can be sensed by devices within proximity to the lamp assembly 3400. This communication technique can be utilized by the UVC lighting or general visible lighting. Signaling via the UVC light may be utilized to control or coordinate other disinfecting devices.

The control system can be disposed external to the UV treatment chamber 341, but locally within the lamp assembly. The disinfection control system can be concealed within a portion of the portable light assembly such that the disinfection control system is obscured from external view by an observer of the portable light assembly. For example, control circuitry may be positioned with the power supply circuitry 3452 and/or the driver circuitry 3406.

The disinfection system can be a retrofit system for a portable light assembly. For instance, a pre-existing lamp can be modified by installing an air inlet, air outlet, UV lamp, and fan into an internal cavity of the lamp shade or other compartment of the lamp. The driver of the visible light can be utilized to drive the UV source and the power supply for the visible light can be utilized to power the UV bulb and fan. In some embodiments, the air treatment system may not include a fan.

The disinfection control system can include a proximity sensor operable to detect proximity of a user. The proximity sensing can be provided by a variety of different types of sensors or combinations of sensors, such as infrared sensors, time of flight sensor, accelerometer, or essentially any other sensor capable of detecting human presence or proximity. The disinfection control system can be operable to change state based on proximity of a user to the portable light assembly.

Figure 35A:
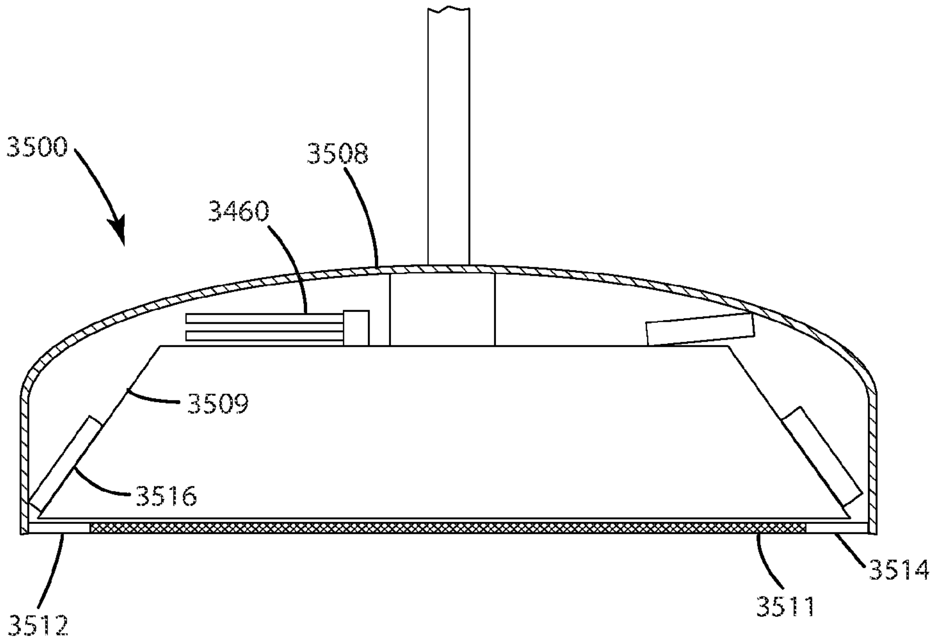
FIG. 35A shows a side sectional view of a portable visible light air disinfection assembly in accordance with another embodiment of the present disclosure.
Figure 35B:
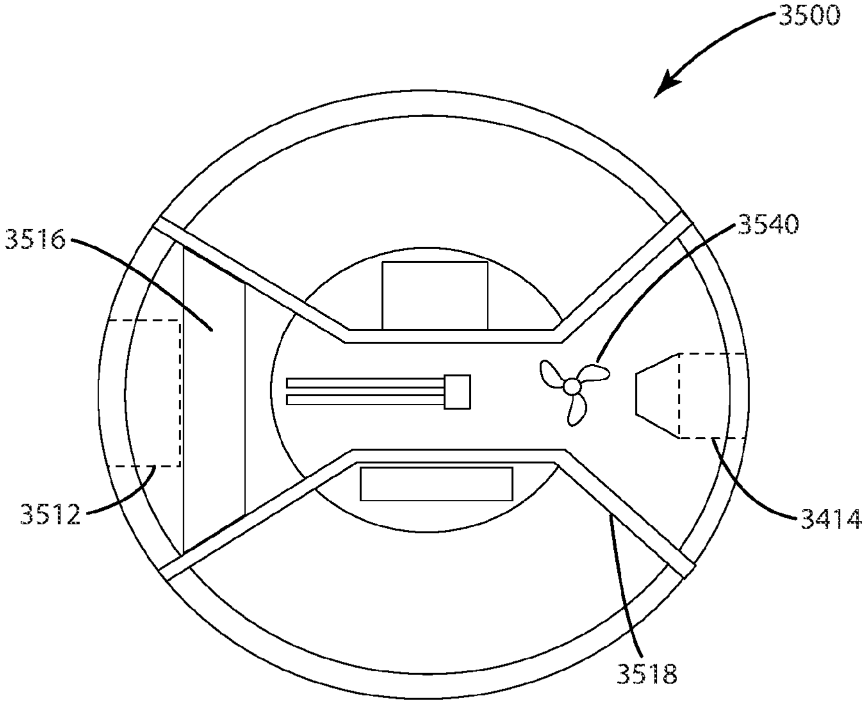
FIG. 35B shows a top sectional view of the FIG. 35A embodiment.

An alternative construction of a combination lamp air disinfection system in accordance with another embodiment of the present disclosure is illustrated in the side and top sectional views of FIGS. 35A-B. FIGS. In this embodiment, the light assembly 3500 can be a pendant light or floor light where the body 3501 is attached to the top wall of the lamp shell 3508. This construction can be similar to that of the table lamp of FIGS. 34A-C. One variation is that the gasket interface 3518 can be configured to provide an air inlet on one side of the lamp shade shell and an air outlet on the other side. Air can enter through the air inlet 3512 and flow through a filter 3516, just as in the FIG. 34A-V embodiment, but instead of having an air outlet in the top wall 3508 of the shell, a fan 3540 can be oriented to direct treated air through an outlet 3514 in the bottom wall 3509 of the lamp shade shell. In one embodiment, the air inlet 3512 or the air outlet 3514, or both, may be notched in a lens 3511 of the light assembly (e.g., a visible light lens and diffuser element). The air inlet 3512 or the air outlet 3514, or both, may be formed by a notch provided at a perimeter of the lens 3511. Alternatively, the air inlet 3512 or the air outlet 3514, or both, may be defined by an aperture in the bottom wall 3509. The air inlet 3512 and the air outlet 3514 may be configured to provide a target amount of airflow for the system to provide effective disinfection.

VIII. Power Management System

Figure 36:
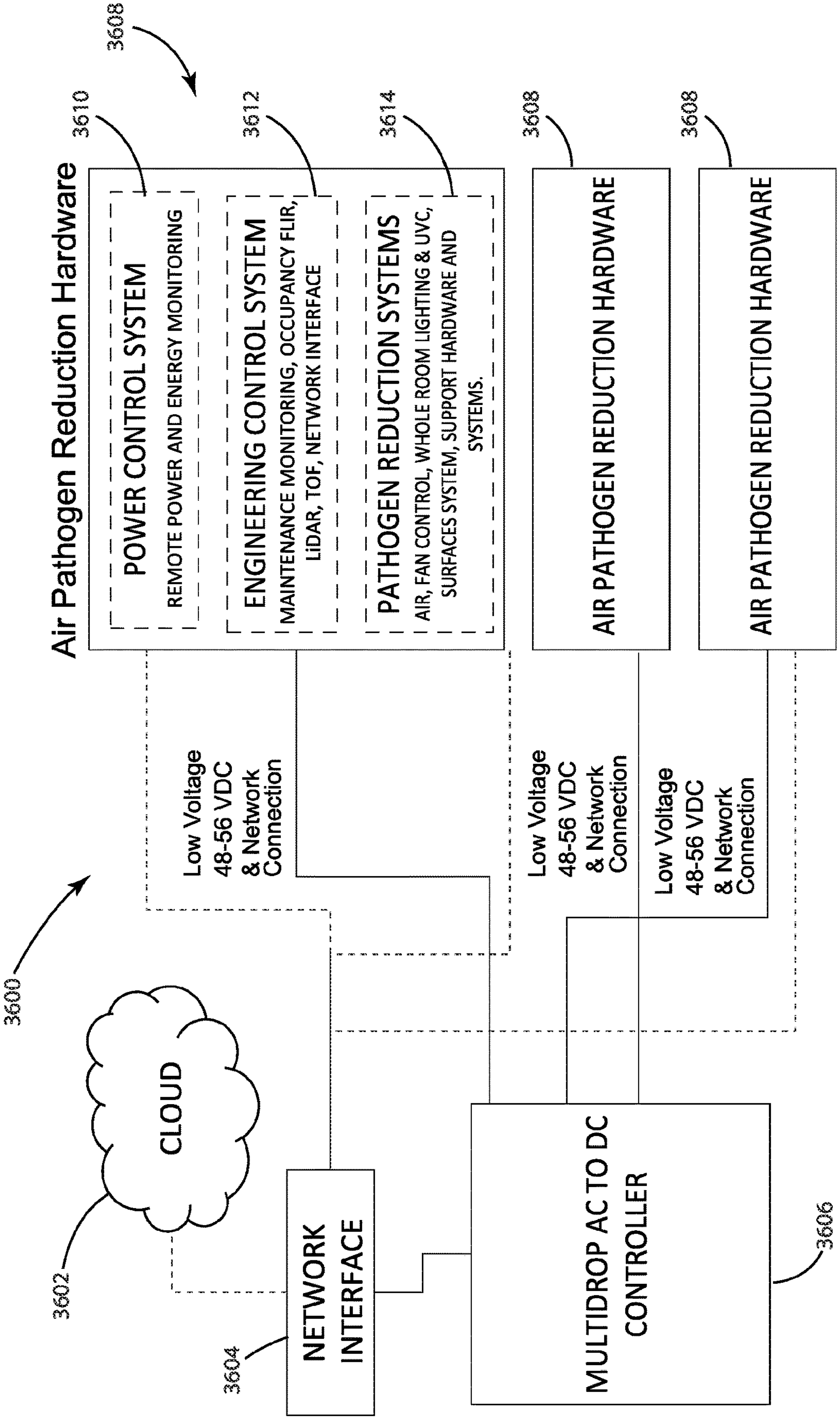
FIG. 36 shows a connected pathogen reduction system accordance with one embodiment.

A power management system 3600, illustrated in FIG. 36, is provided in accordance with the present disclosure for controlling and powering the air disinfection system. The air disinfection system can include multiple air pathogen reduction hardware devices. For example, separate air pathogen reduction hardware modules can be provided throughout a room. Each of these air pathogen reduction hardware modules can include one or more different systems therein, such as one or more power control systems 3610, one or more engineering control systems 3612, and one or more pathogen reduction systems 3614.

One example of a power control system 3610 that can be included in an air pathogen reduction hardware module is remote power and energy monitoring, The power control system can include one or more sensors, for example, current, voltage, power, or other type of sensor that can monitor the amount of power received, expended and report back to a control system, such as control system 200 described in connection with FIG. 2. Local or remote lighting modules can be connected to a master disinfection control system, such as the disinfection control system of FIG. 2. Separate power and control wires can be connected to the disinfection control system. For instance, one of the air pathogen reduction hardware modules can be the disinfection control system of FIG. 2 and be coupled to other air pathogen reduction hardware, such as the portable lamp assembly of FIGS. 34A-B and FIGS. 35A-B via a multidrop AC to DC controller and/or a network interface, such as network interlace 3702. As discussed herein, power over Ethernet can be utilized for communication and power connections, but in alternative embodiments, a wireless network connection among the air pathogen reduction hardware can be utilized or a wireless or wired network connection to a common server, such as a cloud-based server where control and data collection can be enacted as part of a cloud-based control system 3602.

Examples of engineering control systems 3612 include maintenance monitoring modules, occupancy forward-looking Infrared (FLIR) modules, light detection and ranging (LiDAR) modules, time of flight (TOF) modules, and network interlace modules. These various engineering control systems 3612 can be included at the air pathogen reduction hardware to provide engineered control functionality. These modules are exemplary and other types of engineering control system modules can be provided, alone or in combination with other engineering control modules depending on the desired functionality of the air pathogen reduction hardware.

Examples of pathogen reduction systems 3614 that can be utilized in the air pathogen reduction hardware include one or more of air control, fan control, whole room lighting and ultraviolet-C disinfection, surface disinfection systems, support hardware and other various pathogen reduction systems. The pathogen reduction systems can provide disinfection functionality.

The air pathogen reduction hardware can be powered from a multidrop AC to DC controller 3606 that is connected to mains. A multidrop AC to DC controller can provide low-voltage differential swing multidrop connections. That is, a multidrop controller can provide power to a plurality of different air pathogen reduction hardware systems. The power can provided through daisy chained connections of air pathogen reduction hardware or through parallel connections as depicted in FIG. 36.

In the current embodiment, the multidrop AC to DC controller converts AC power to 42-56 VDC power, or 48-56 VDC power, or another voltage level sufficient to power the air pathogen reduction hardware, and distributes the power to the air pathogen reduction hardware modules for operating power.

The multidrop controller can also provide network connections to the air pathogen reduction hardware over the low voltage network. That is, in some embodiments, the multidrop controller acts as a driver that can transmit and receive data to and from multiple air pathogen reduction modules simultaneously or in sequence. The multidrop controller can include a network interface or can be connected to an external network interface 3604 as depicted in FIG. 36. The network interface 3604 can connect to the cloud to provide Internet communication and Internet of Things functionality to the air pathogen reduction hardware. For example, data can be collected and managed in a cloud-based service. Further, the air pathogen reduction systems can be controlled and monitored from a remote device that communicates with a cloud-based server or that communicates with the multidrop controller 3606.

The multidrop controller can provide various functionality in connection with the air pathogen reduction hardware. For example, the multidrop controller can monitor current, control scheme, balance between various parameters, energy control and can manage communications. For example, the multidrop controller can connect to the air pathogen reduction hardware with DC copper or Ethernet power over Ethernet (POE) and manage those connections.

Figure 37:
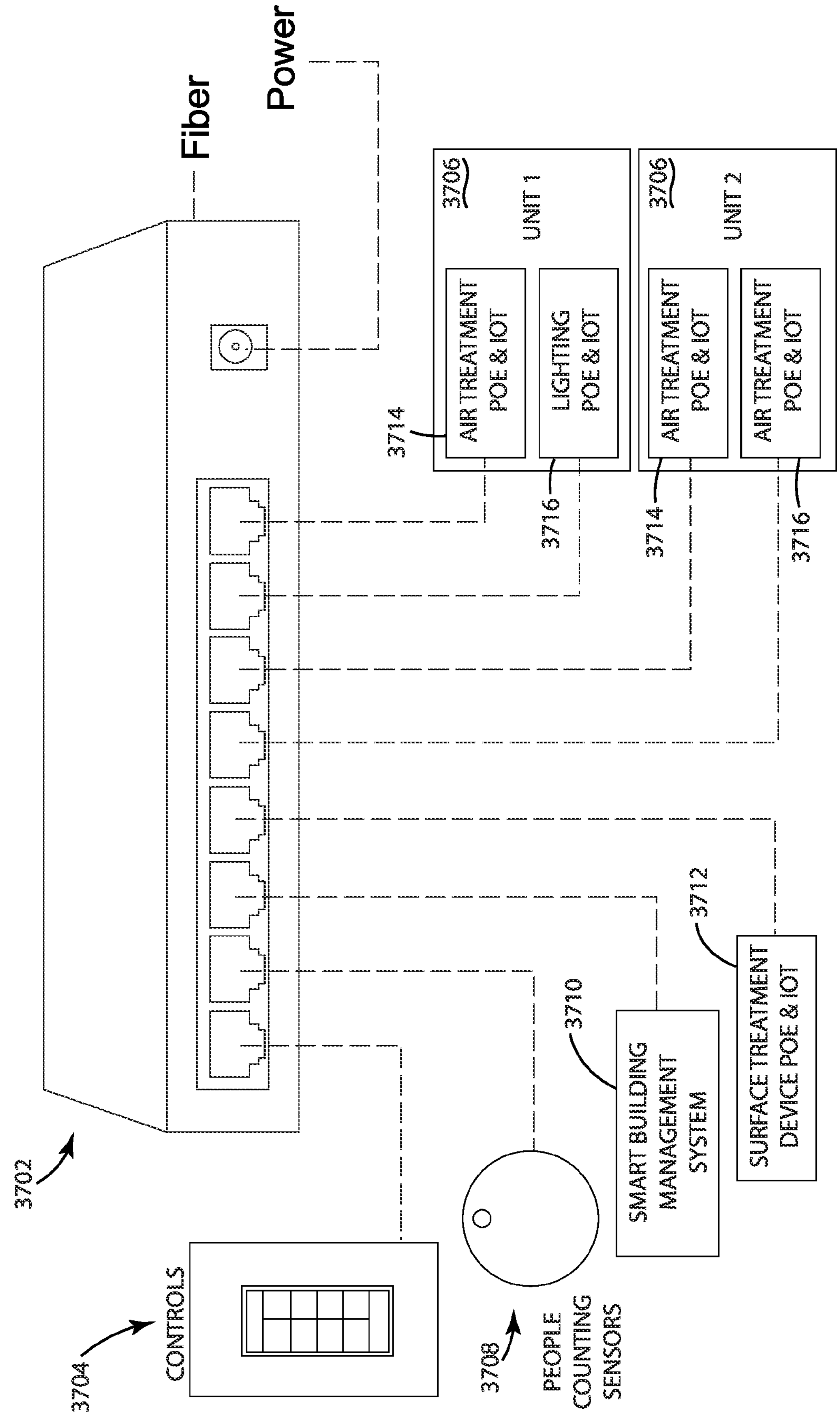
FIG. 37 shows a connected pathogen reduction system in accordance with one embodiment.

One example of a network interlace 3702 and associated topology that can be utilized in connection with a power management system of the present disclosure is illustrated in FIG. 37. Power over Ethernet generally describes any standard or ad choc system that passes electric power along with data on Ethernet cabling. The network interlace 3702 depicted in this embodiment has 8 ports, 5 POE ports and 3 communication ports that provide communication but do not provide power over Ethernet. In alternative embodiments, the network interface may have additional or fewer POE ports and communication ports. The network interface 3702 includes a power input that can be connected to mains power or another power source. The network interface 3702 also includes an inbound network connection, such as a fiber Internet connection that enables the network interface to communicate with cloud based services or with other remote servers or computers.

The POE network interface ports allow a single cable to provide both data connection and electric power to devices. In the depicted embodiment, power and communication can be provided to surface treatment devices 3712 and air pathogen reduction hardware units 3706, for example the depicted units that include an air treatment module 3714 and visible lighting module 3716 The POE connections can be provided as a supplement or instead of the multidrop controller connections. In some situations, certain devices may only receive power or may only receive communication. In other situations, all devices both receive power and are capable of communication over the network. The POE can be provided via IEEE 802.3 such as alternative A, alternative B, 4PPoE standards, or essentially any other POE type protocol.

Via this network interface 3702, network connections can be provided to the various local devices, for example various devices located around a room. For example, several different combination air treatment and visible lighting units 3706 as well as surface treatment modules 3712 can be installed throughout a room and connected via POE in order to make each module a separate, individually addressable Internet of Things device. The controls in the room 3704 can be programmed to control the certain designated devices in unison or to control conc one or more devices individually. The smart building management system can also be in communication with the system and can issue commands to the various devices via the network as well as receive reports regarding disinfection and other information available from the surface treatment devices 3712, combination units 3706, sensors, controls, or any other equipment connected to the POE network interface 3702.

The network interface can be connected to various sensors, such as a people counting sensor 3708 that can count the number of people in proximity of the sensor. The tracking information can be relayed through the network interlace to a cloud server. The data can be utilized to improve disinfection and disinfection cycle interruption recovery strategies.

Figure 42:
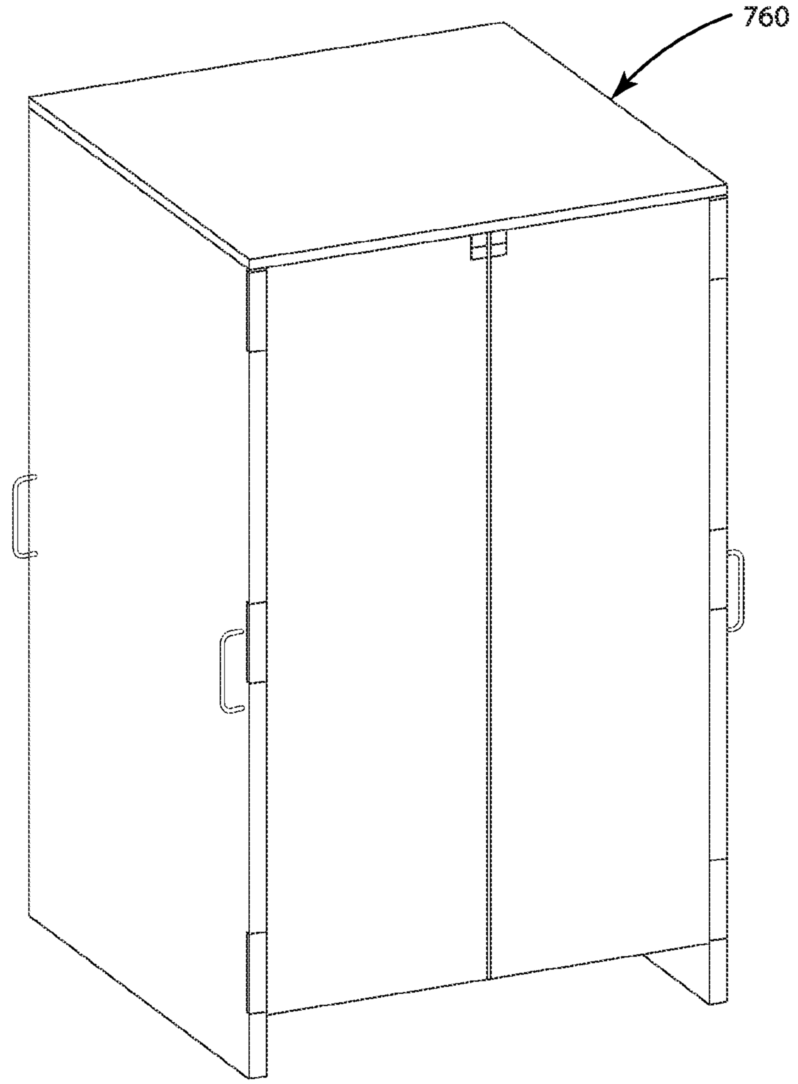
FIG. 42 shows a booth in accordance with one embodiment.

In one embodiment, the power management system 3600 may be incorporated into a booth (e.g., a telebooth) for providing one or more remote services, such as health services (sometimes referred to as a telehealth or telemedicine booth). An example of such a booth is depicted in FIG. 42 and generally designated 760. The booth 760 may include any one or more aspects of embodiments described herein, including an air treatment system. The booth 760 may include an integrated air treatment system and UV surface disinfection system. The air treatment system may take in internal air, circulate a portion back into the booth 760, and discharge a portion from the booth 760 via an outlet for cooling the booth 760. The treated exit air for cabins and private spaces can be configured with a return air vent (returning air into the cabin) and may include an exit vent (returning treated air to the exterior environment). This allows a portion of air to be treated internally and a portion treated and exited from the cabin contributing to cooling the cabin.

IX. Converter System

Figure 38:
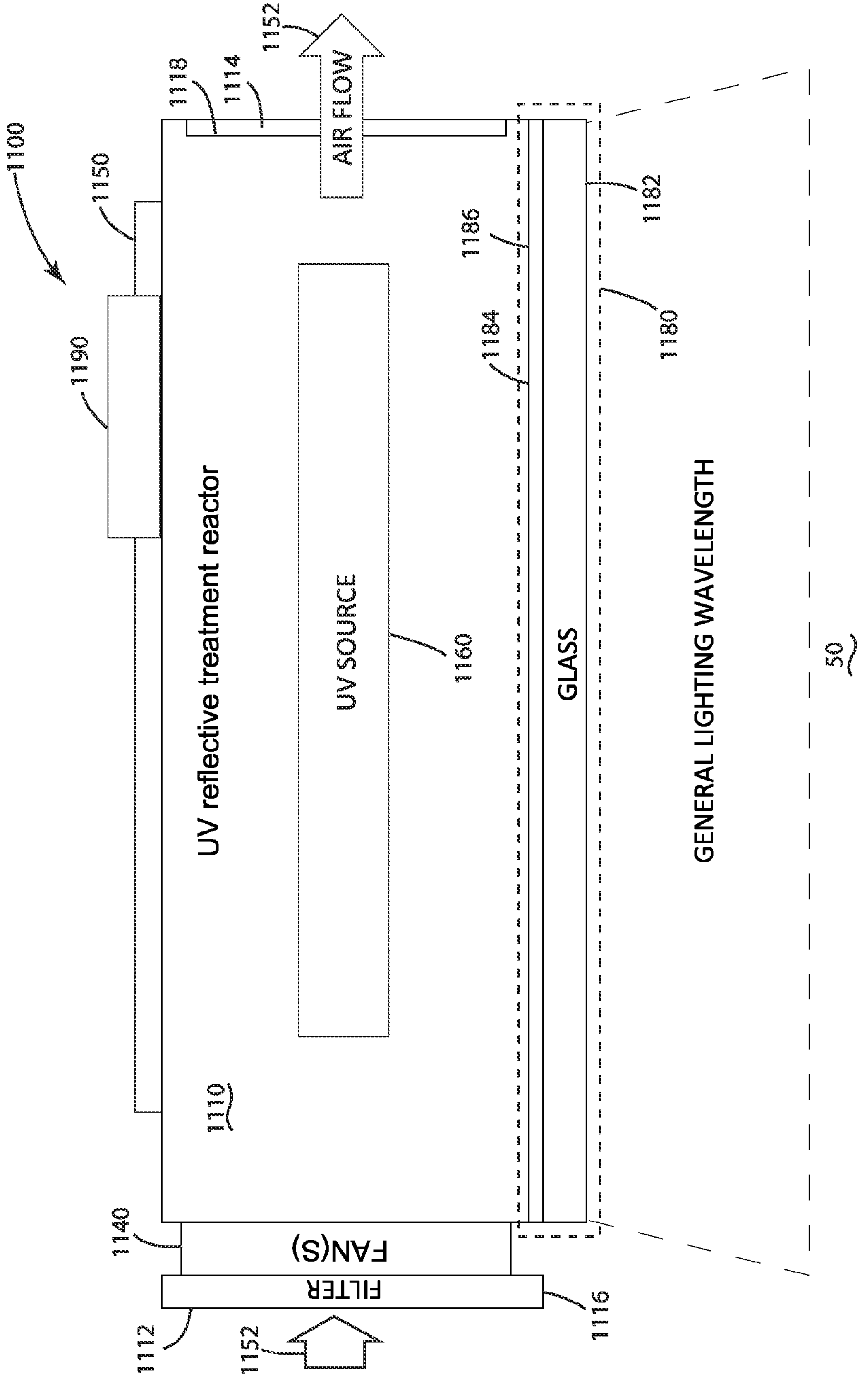
FIG. 38 shows a treatment system in accordance with one embodiment.

A light fixture in accordance with one embodiment of the present disclosure is shown in FIG. 38 and generally designated 1100. The light fixture 1100 may include any one or more aspects of embodiments described herein, including any one or more aspects of the light fixture 100. Likewise, the light fixture 100 may include any aspect of the light fixture 1100. It is to be noted that one or more aspects of the light fixture 1100 may be absent to yield one or more alternative embodiments.

The light fixture 1100 may be similar in some respects to the light fixture 100 described herein with several exceptions. For instance, the light fixture 1100 may include a support member 1150, similar to the support member 150, that is operable to facilitate mounting the light fixture 1100 to a surface. The surface may be the exposed surface of an interior wall of a room or a surface interior to the wall, such as a wall stud that is hidden from view. The light fixture 1100 may include a control system 1190, similar to the control system 200, operable to direct operation of the light fixture 1100 as described herein. The control system 200 may receive power from a power source, and direct such power to components of the light fixture 1100 (e.g., a UV light source 1160 and a fan 1140).

In one embodiment, the light fixture 1100 may be controlled by a switch (not shown), similar to the switch 154 of the light fixture 100, and which may be disposed remotely from the light fixture 1100. The switch may be operable to control supply of power to a subset of components of the light fixture 1100. Circuitry and components of the light fixture 100 may remain active or inactive regardless of the state of the switch.

The light fixture 1100 may include a treatment chamber 1110, similar to the treatment chamber 110, through which air may be directed and in which the air may be treated with UV light from a UV light source 1160. The UV light source 1160 may be a germicidal light source operable to generate the UV light in response to being supplied power from the power source. For example, the UV light source 1160 may be a UV-C source, such as a cold cathode lamp, a low pressure mercury lamp, or UV-C light emitting diodes.

The UV light source 1160 may be powered in a manner similar to the UV light source 160. For instance, power applied to the UV light source 160 may be a conditioned form of the power from a power source.

In the illustrated embodiment, untreated air 1152 may enter the treatment chamber 1110 via an air inlet 1112, and treated air 1154 may exit the treatment chamber 1110 via an air outlet 1114. The air inlet 1112 may be in fluid communication with a filter assembly 1116, which may be configured to filter particulates from the untreated air 1152 prior to being treated by UV light in the treatment chamber 1110. Removal and replacement of the filter assembly 1116 may be conducted on a periodic basis to prevent substantial clogging of the filter assembly 1116.

As discussed herein, treated air 1154 may exit the treatment chamber 1110 via an air outlet 1114. The air outlet 1114 may include a vent 1118 configured to allow airflow therethrough at a flow rate sufficiently greater than a flow rate of the treated air 1154.

The light fixture 1100 may include a fan assembly 1140 operable to direct air through the treatment chamber 1110 from the air inlet 1112 to the air outlet 1114. In the illustrated embodiment, the fan assembly 1140 is disposed proximal to the air inlet 1112; however, it is to be understood the present disclosure is not so limited. The fan assembly 1140 may be disposed or provided in a different position to direct air through the treatment chamber 1110. The fan assembly 1140 may include a fan operable to direct air through the treatment chamber 1110 at a target flow rate for disinfection or decontamination of the air via application of UV light within the treatment chamber 1110. The fan assembly 1140 may include one or more fans operable to direct air through the treatment chamber 1110.

The untreated air 1152, the air inlet 1112, the filter assembly 1116, fan 1140, the air outlet 1114, the vent 1118, and the treated air 1154 may be similar respectively to the untreated air 52, the air inlet 112, the filter assembly 116, fan 140, the air outlet 114, the vent 118, and the treated air 154.

In the illustrated embodiment, the light fixture 1100 is depicted without baffles; however, it is to be understood that the light fixture 1100 may include baffles, such as the baffle assemblies 130A, 1308 described herein in conjunction with the light fixture 100.

The light fixture 1100 in one embodiment may include a visible light module 1180 operable to supply visible light to a room area 50 of the room. The visible light module 1180 may be operable to convert UV light from the UV light source 1160 into visible light and to facilitate directing such light to the room area 50.

The visible light module 1180 may include a UV light converter 1184 operable to receive the UV light from the UV light source 160. The UV light converter 1184 may be configured to provide visible light that is based on the UV light received from the UV light source 160. This visible light may be provided to illuminate the room area.

In the illustrated embodiment, the UV light converter 1184 is a UV light downconverter operable to convert the UV light to the visible light. The UV light converter 1184 may include a substrate 1184 (e.g., glass) on which a film 1186 is disposed, where the film 1186 is operable to convert UV light to visible light. The film 1186 may be a down conversion layer, and the substrate 1184 may be light transmissive. The film 1186 may be disposed upstream of the substrate 1184 relative to the UV light source 1160 so that UV light from the UV light source 1160 may be converted to visible light before traveling through the substrate 1184 and into the room area 50.

The UV light converter 1184 may constructed in a variety of ways, including downconverting nanophosphors, which may be formed of $SiO_2$ co-doped with Ce and Tb, or nano-crystal with different band gaps to provide down conversion. These structures may be provided on or form the film 1186 to enable down conversion of the UV light output from the UV light source 1160 to visible light.

The UV light converter 1184 in accordance with one embodiment may provide a passive converter or passive conversion system for converting UV light to visible light. The light fixture 1100 may not utilize power 1) to convert the UV light or 2) to generate visible light separately from the UV light source 1160, or both.

The UV light converter 1184 may be configurable in a variety of ways, depending on the application. In one embodiment, the UV light converter 1184 may be configurable to customize the light fixture 1100 without substantial modification to the light fixture 1100. For instance, the UV light converter 1184 may be configurable for a target color temperature, based on user selection or parameters. The UV light converter 1184 may be configurable for such a target color temperature without affecting the overall build of the light fixture 1100, enabling the light fixture 1100 to be manufactured for applications regardless of the target color temperature. As an example, the UV light converter 1184 is replaceable with another UV light converter 1184 capable of providing visible light having a second color temperature different from a first color temperature of visible light that is output from the UV light converter 1184. One or more additional or alternative parameters may be affected by the UV light converter 1184, enabling the light fixture 1100 to be manufactured for applications regardless of the additional or alternative parameters.

The UV light converter 1184, in one embodiment, may be replaceable in the field after the light fixture 1100 has been installed to vary one or more characteristics of the light fixture 1100.

In one embodiment, the light fixture 1100 may include a visible light regulator, similar to the UV light regulator 120 described herein except operable to control emission of visible light in to the room. The visible light regulator may be operable to selectively control emission of visible light into the room area 50 based on directive from the control system 1190. As an example, the visible light regulator may include one or more apertures selectively transmissive with respect to visible light output from the UV light converter 1184.

In an alternative embodiment, the UV light converter 1184 may be an up converter that is configured to convert visible light to UV light. In one embodiment, the light fixture 1100 may include a visible light source (e.g., such as the visible light source 180) capable of generating visible light for illuminating the room area 50. The visible light from the visible light source may be directed toward the UV light converter 1184 and toward the treatment chamber 1110. The UV light converter 1184 may up convert the visible light to UV light for disinfection of air flowing through the treatment chamber 1110. Example configurations of an up conversion configuration may include lanthanide-doped upconversion phosphor (UCP) materials, such as lanthanide-doped upconversion luminescent nano- and microcrystalline $Y_2SiO_5$.

X. Filter Disposal System

Figure 39:
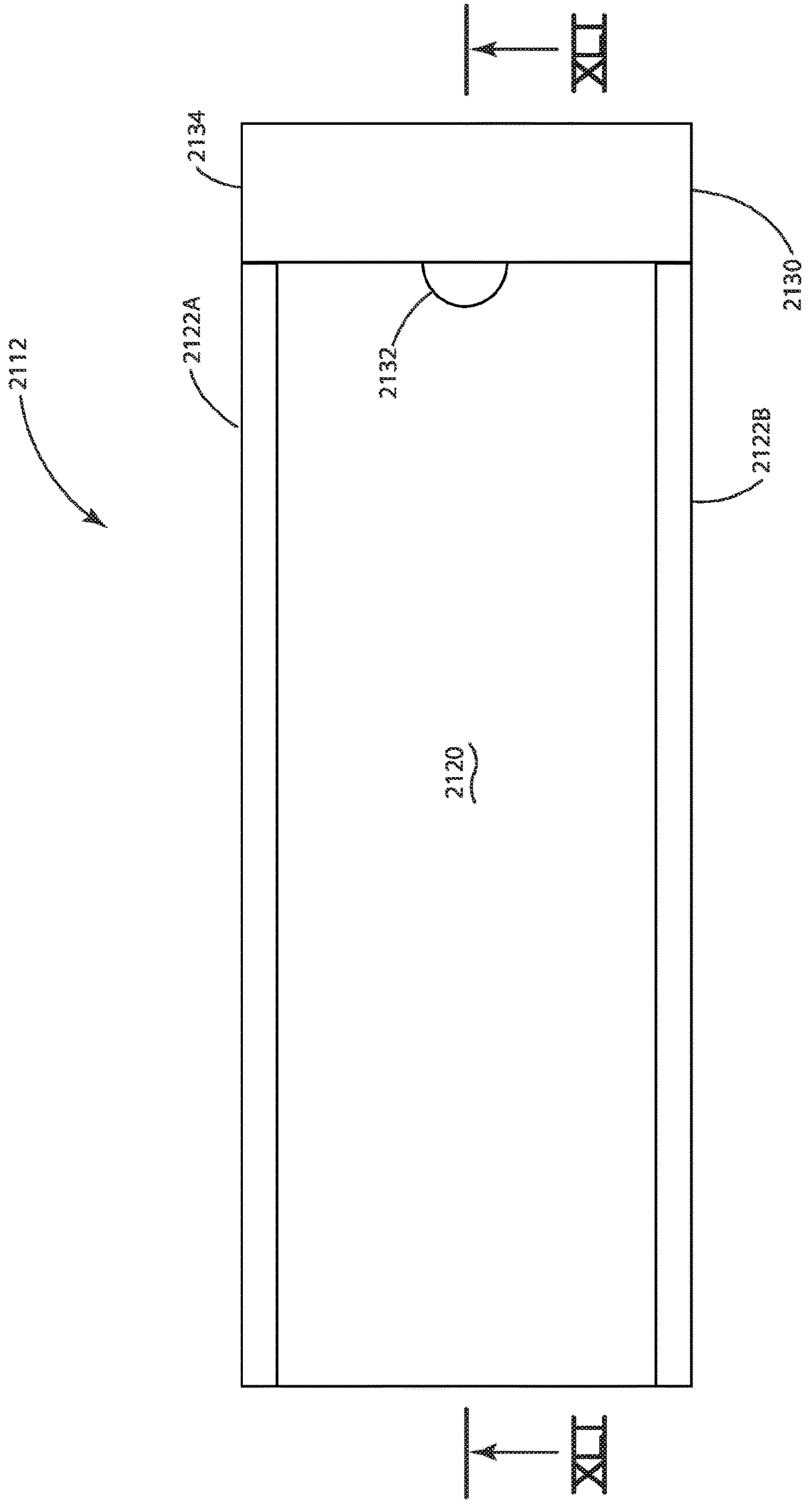
FIG. 39 shows a filter disposal system in accordance with one embodiment in a stowed mode.
Figure 40:
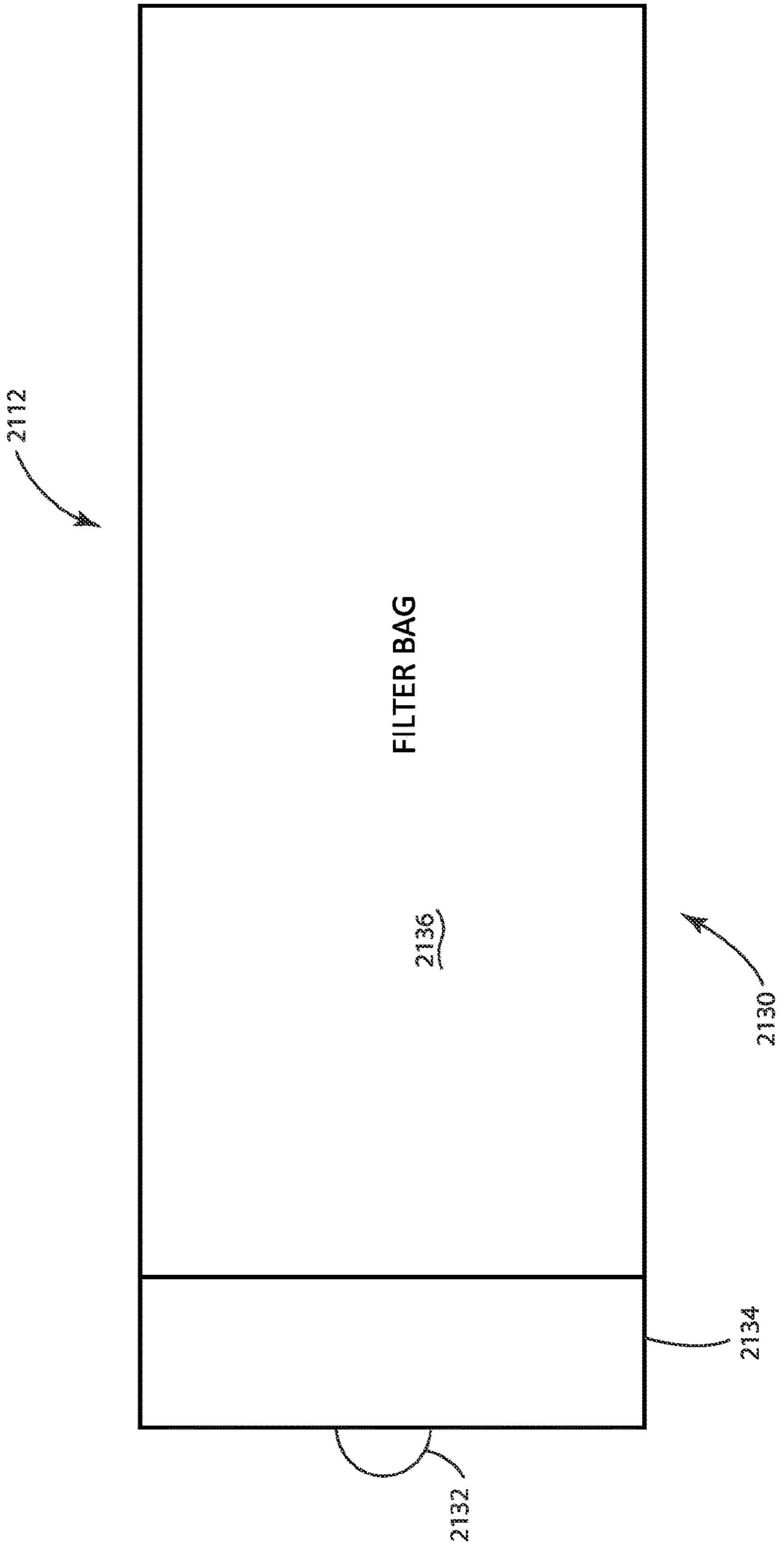
FIG. 40 shows the filter disposal system of FIG. 39 in a disposal mode.
Figure 41:
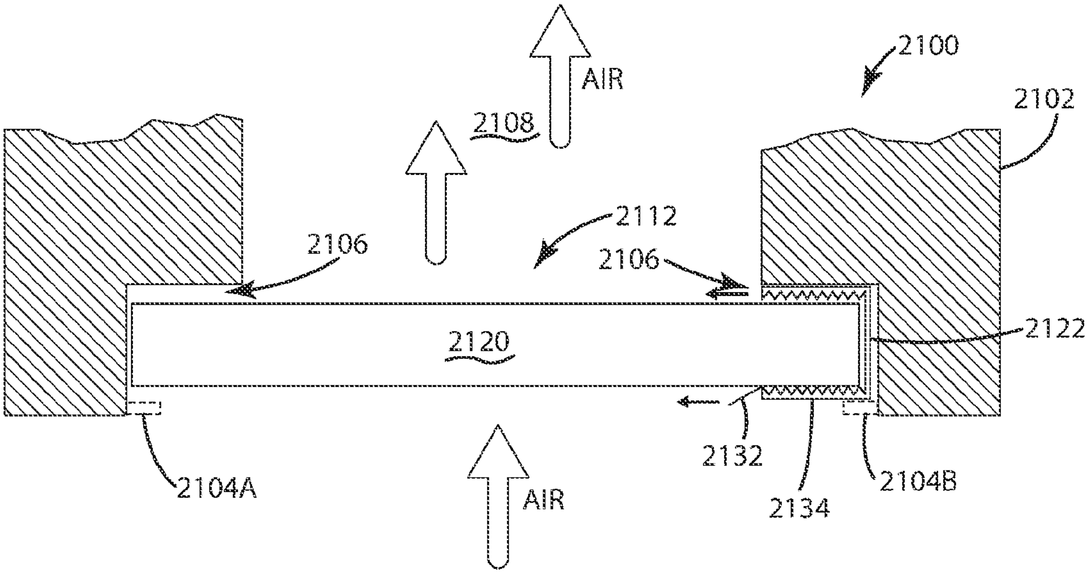
FIG. 41 shows a sectional view of FIG. 39 in conjunction with a sectional view of a treatment system.

A filter assembly in accordance with one embodiment is shown in FIGS. 39-41 and generally designated 2112. The filter assembly 2112 may be configured for use in conjunction with a light assembly 2100, which may be similar to any light fixture or light configuration described herein. The light assembly 2100 may include a filter support 2102 having a receiver 2106 that is configured to maintain a position of the filter assembly 2112 in place with respect to a treatment chamber 2108 and the air traverses through the filter assembly 2112 into or out of the treatment chamber 2108.

The filter assembly 2112 in the illustrated embodiment includes a filter storage element 2130 (e.g., a disposable bag) movable from a stowed position to a filter disposal position to facilitate disposal of the filter assembly 2112 in a manner that allows the user to substantially avoid contacting a filter media 2120 of the filter assembly 2112.

The filter assembly 2112 may include a filter media 2120, as discussed herein, that may remove particulates from air flowing into or out of a UV treatment chamber 2108 of a light assembly 2100. The filter media 2120, in one embodiment, may be a MERV6 type of filter media capable of removing such particulates. The filter media 2120 may be sufficiently flexible to allow deformation for installation of the filter assembly 2212 into a receiver 2106 of the light assembly 2100, while being sufficiently rigid to form an interference fit with the receiver 2106 to facilitate maintaining a position of the filter assembly 2112 in the receiver 2106 of the light assembly 2100. In an alternative embodiment, the receiver 2106 may be defined by first and second brackets that receive the filter assembly 2112 by sliding the filter assembly 2112 into the receiver 2106 along a longitudinal axis of the filter assembly 2112, where upper and lower portions of the filter assembly 2112 slide along the receiver 2106 until the filter assembly 2112 is disposed in a position to filter particulars, and where the receiver 2106 in this arrangement substantially prevents movement of the filter assembly 2112 along a direction aligned with the air flow direction (e.g., normal to a primary face of the filter assembly 2112).

In the illustrated embodiment, the filter assembly 2112 includes at least one filter support 2112A-B (e.g., first and second filter supports 2112A, 2112B) disposed respectively on one or more sides of the filter media 2120. The first and second filter supports 2112A-B may be paperboard coupled to the filter media 2120 (with or without adhesive) to maintain a shape of the filter media 2120 and one or more axes, such as the longitudinal or transverse axis of the filter media 2120. The first and second supports 2112A-B may deflect during installation of the filter assembly 2112 into the receiver 2106 of the light assembly 2100. The first and second supports 2112A-B may define slides over which a filter bag 2136 may slide as the filter bag 2136 is transitioned from a stowed position to a disposal position, as described herein.

As an example, the at least one filter support 2112A-B may be a paperboard frame disposed about at least a portion perimeter of the filter media 2120 (e.g., a part of or the entirety of the parameter-perimeter). The paperboard frame may substantially maintain a shape of the filter assembly 2112 to be consistent with a shape of the receiver 2106 of the light assembly 2100. Additionally, or alternatively, the light assembly 2100 may include a support grid (e.g., a metal screen) disposed on at least one face of the filter media 2120 that is normal to a direction of airflow through the filter media 2120.

Optionally, the light assembly 2100 may include at least one lip 2104A-B configured to facilitate maintaining a position of the filter assembly 2112 in the receiver 2106 of the light assembly 2100. The at least one lip 2104A-B may enable maintaining the position of the filter assembly 2112 with or without the interference fit described herein in conjunction with the receiver 2106 and the filter assembly 2112. For instance, the at least one lip 2104A-B may hold the filter assembly 2112 in place with respect to the receiver 2106 without reliance on an interference fit and without presence of an interference fit between the filter assembly 2112 and the receiver 2106.

The filter assembly 2112 in the illustrated embodiment includes a filter storage element 2130 that is integral to the filter assembly 2112. The filter assembly 2112 may be installed for use with the light assembly 2100 and with the filter storage element 2130 in the stowed position as in the illustrated embodiment of FIG. 39. The filter storage element 2130 includes a disposal interlace 2132 (e.g., a pull tab) capable of being pulled by a user to transition the filter storage element 2130 from the stowed position to a disposal position as depicted in the illustrated embodiment of FIG. 36X. The transition between the stowed position in the disposal position may be conducted with the filter assembly 2112 in situ or in place with respect to the receiver 2106. As a result, a user can transition the filter assembly 2112 to a disposal configuration before removing the filter assembly 2112 from the light assembly 2100, enabling the user to configure the filter assembly 2112 in a disposal mode and remove the filter assembly 2112 without touching the filter media 2136 and/or without substantially disturbing the filter media 2136 in an uncontained arrangement during removal of the filter assembly 2112. This way, particulates captured by the filter media 2136 can be maintained substantially within the filter storage element 2130 during removal of the filter assembly 2112 from the light assembly 2100.

The filter storage element 2130, in the illustrated embodiment, includes a filter bag 2136 secured to a side portion 2122 of the filter media 2120 and arranged in a stowed position, as depicted in the illustrated embodiment of FIGS. 39 and 41. The filter bag 2136 may be expandable from the stowed position to the disposal position depicted in the illustrated embodiment of FIG. 40. The user may grab the disposal interlace 2132 to expand the filter bag 2136 around the filter media 2120 to substantially contain the filter media 2120 within the filter bag 2136. As discussed herein, expansion of the filter bag 2136 around the filter media 2120 may be conducted by pulling the disposal interlace 2132 while the filter assembly 2112 is in place with respect to the receiver 2106 of the light assembly 2100.

In the illustrated embodiment, the filter storage element 2130 includes a disposal support element 2134 that may be secured to the filter bag 2136 and configured to substantially protect the filter bag 2136 in the stowed position. For instance, the disposal support element 2134, with the filter storage element 2130 in the stowed position, may substantially shield the filter bag 2136 from view when the filter assembly 2112 is disposed within the receiver 2106.

In the illustrated embodiment, the disposal interface 2132 may also facilitate removal of the filter assembly 2112 from the receiver 2106 of the light assembly 2100. For instance, a user may grab the disposal interface 2130 to transition the filter bag 2136 to a disposal position and further pull on the disposal interface 2130 to remove the filter assembly 2112 from the receiver 2106. In one embodiment, as described herein, the receiver 2106 may include a lip 2104A-B (which may operate as a catch) that can be overcome by the user pulling on the disposal interface 2130 in a direction parallel to the flow of air, such that the filter assembly 2112 is capable of deformation sufficient to overcome the lip 2104A-B for removal of the filter assembly 2112 from the receiver 2106.

Negative air pressure with UVA in room performance over time and alarms may be determined by a system in accordance with one embodiment. By tracking positive air pressure changes or negative air pressure changes, or both, the system may identify exits and entrances of potentially contaminated airflow. For example: if a room is kept at a negative air pressure, the room theoretically will not contaminate other rooms. However, large movements from that room externally may create momentary events where air from that room moves externally. Multiple people moving out of the room with the door open acts as a column of air being pulled from that room. These such events can be tracked and monitored based on pressure changes to determine a risk level and to identify opportunities to treat adjacent areas. As people are typically the source of contamination, tracking sensor information to understand movement and airflow may enable the system to determine a large portion of the transfer of contamination.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation (s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The invention claimed is:

1. A UV light fixture installable in a ceiling grid and that fits within a conventional ceiling opening for tiles for disinfecting air within a room, the UV light fixture comprising:

a support member operable to facilitate mounting the UV light fixture to the ceiling grid, whereby the UV light fixture retrofits in place of an existing conventional light fixture a surface;

a germicidal light source operable to generate UV light;

a UV treatment chamber having an untreated air inlet and a treated air outlet, the UV treatment chamber having an air treatment region operable to receive air from the untreated air inlet and to direct air to the treated air outlet, wherein the UV light from the germicidal light source is directed to the air treatment region; and a moveable visible light assembly that acts as a maintenance access panel to the UV treatment chamber, the moveable visible light assembly including a visible light source operable to generate visible light for illuminating the room, wherein the visible light assembly is movable between an accessible UV treatment chamber position and an inaccessible UV treatment chamber position relative to the UV treatment chamber, the moveable visible light assembly including a reflector operable to reflect visible light received from the visible light source toward the room, wherein the accessible UV treatment chamber position permits user access to the UV treatment chamber from the room while the fixture remains installed in the ceiling grid.

2. The fixture of claim 1 including a plurality of baffles cooperatively operable to substantially prevent leakage of the UV light from the UV treatment chamber into the room through the untreated air inlet, wherein the plurality of baffles are provided within the UV treatment chamber.

3. The fixture of claim 1 comprising a UV light regulator in light communication with the germicidal light source, the UV light regulator operable to selectively control an amount of the UV light directed into the room from the germicidal light source.

4. The fixture of claim 3 wherein the UV light regulator includes a stationary window that is transmissive to the UV light, wherein the UV light regulator includes a slidable window surrounded by an opaque structure, wherein the slidable window is capable of moving relative to the stationary window to selectively control a size of an effective aperture available for UV light transmission to the room from the germicidal light source.

5. The fixture of claim 3 wherein the UV light regulator is operable to obtain occupancy information pertaining to occupants present in the room, wherein the UV light regulator is operable to selectively provide the UV light into the room based on the occupancy information being indicative that no occupants are present in the room.

6. The fixture of claim 1 comprising a control system operable to control operation of the germicidal light source, the control system including a wireless communication controller configured to transmit information to and receive information from an external network device.

7. The fixture of claim 1 comprising a first reflector configured to direct the UV light from the germicidal light source to a target surface in the room within a UV light region, the UV light region being defined by the target surface and an opposing boundary line that is parallel to or converges with the target surface.

8. The fixture of claim 1 comprising a fan operable to direct air through the UV treatment chamber of the fixture, the fan operable to direct air to the UV treatment chamber from the air inlet and operable to direct air from the treatment chamber to the air outlet; and a controller configured to control speed of the fan.

9. The fixture of claim 8 wherein the controller is configured to track pressure changes in the room based on fan operating conditions.

10. The fixture of claim 1 comprising a controller and an audio sensor, wherein the controller is configured to receive audio sensor output from the audio sensor and recognize an occupancy event based on the audio sensor output.

* * * * *